United States Patent
Gao et al.

(10) Patent No.: US 11,103,171 B2
(45) Date of Patent: Aug. 31, 2021

(54) SYSTEMS AND METHODS FOR SCREENING, DIAGNOSING, AND STRATIFYING PATIENTS

(71) Applicant: BlackThorn Therapeutics, Inc., San Francisco, CA (US)

(72) Inventors: Qingzhu Gao, San Francisco, CA (US); Humberto Andres Gonzalez Cabezas, Santa Clara, CA (US); Parvez Ahammad, San Jose, CA (US); Yuelu Liu, South San Francisco, CA (US)

(73) Assignee: BlackThor Therapeutics, Ine., San Francisco, CA (US)

( * ) Notice: Subject to any disclaimer, the term of this patent is extended or adjusted under 35 U.S.C. 154(b) by 0 days.

(21) Appl. No.: 16/661,751

(22) Filed: Oct. 23, 2019

(65) Prior Publication Data

US 2020/0121236 A1  Apr. 23, 2020

Related U.S. Application Data

(60) Provisional application No. 62/749,473, filed on Oct. 23, 2018, provisional application No. 62/864,283, filed on Jun. 20, 2019.

(51) Int. Cl.
  G16H 10/20 (2018.01)
  G16H 50/20 (2018.01)
  (Continued)

(52) U.S. Cl.
  CPC ............. *A61B 5/165* (2013.01); *G16H 10/20* (2018.01); *G16H 10/60* (2018.01); *G16H 20/10* (2018.01); *G16H 20/70* (2018.01); *G16H 50/20* (2018.01)

(58) Field of Classification Search
  CPC .. G06Q 10/06375; G06Q 50/24; G16H 10/60; G16H 50/20; G16H 50/30;
  (Continued)

(56) References Cited

U.S. PATENT DOCUMENTS

| 6,071,236 A | 6/2000 | Iliff |
| 2008/0012855 A1 | 1/2008 | Bi |

(Continued)

FOREIGN PATENT DOCUMENTS

| AU | 2003204909 B2 | 1/2005 |
| CA | 2715825 A1 | 8/2009 |

(Continued)

OTHER PUBLICATIONS

Kessler, R. C. et al.; "Short screening scales to monitor population prevalences and trends in non-specific psychological distress"; Psychological Medicine, vol. 32, pp. 959-976; 2002, Cambridge University Press; DOI: 10.1017/S0033291702006074 (18 pages).

(Continued)

*Primary Examiner* — Maroun P Kanaan
(74) *Attorney, Agent, or Firm* — Nixon Peabody LLP

(57) ABSTRACT

A system includes a display device, a user interface, a memory, and a control system. The memory contains machine readable medium including machine executable code storing instructions for performing a method. The control system is coupled to the memory, and includes one or more processors. The control system is configured to execute the machine executable code to cause the control system to display, on the display device, a series of questions from mental health questionnaires. The series of questions includes text and answers for each question. From the user interface, a selection of answers of each of the displayed series of questions is received from a patient. Using a Bayesian Decision List, the received selection of answers is (Continued)

processed to output an indication of mental health of the patient. The indication of mental health identifies a kappa opioid receptor antagonist to which the patient would likely be a higher responder.

16 Claims, 44 Drawing Sheets

(51) Int. Cl.
  *A61B 5/16* (2006.01)
  *G16H 20/70* (2018.01)
  *G16H 10/60* (2018.01)
  *G16H 20/10* (2018.01)

(58) Field of Classification Search
  CPC ........ G16H 20/70; G16H 20/10; G16H 20/17; G16H 40/63; G16H 50/70; G16H 30/40; G16H 40/67; G16H 10/20; G16H 15/00; G16H 50/50; A61P 25/24; A61P 25/00; A61P 43/00; A61B 5/165; A61B 5/4088; A61B 5/0205; A61B 5/42; A61B 5/021; A61B 5/024; A61B 5/168; A61B 5/4803; A61B 5/02405
  See application file for complete search history.

(56) References Cited

U.S. PATENT DOCUMENTS

| | | | |
|---|---|---|---|
| 2009/0299645 A1* | 12/2009 | Colby | G16H 50/30 702/19 |
| 2014/0276549 A1* | 9/2014 | Osorio | A61M 5/1723 604/503 |
| 2016/0063205 A1* | 3/2016 | Moturu | G16H 10/60 705/3 |
| 2016/0110524 A1 | 4/2016 | Short | |
| 2016/0210442 A1* | 7/2016 | Ethington | G16H 40/20 |
| 2017/0018007 A1 | 1/2017 | Defrank | |
| 2017/0168070 A1 | 6/2017 | Oberoi | |
| 2017/0340261 A1 | 11/2017 | Torres | |
| 2018/0116574 A1 | 5/2018 | Short | |
| 2018/0182472 A1 | 6/2018 | Preston | |
| 2019/0102511 A1* | 4/2019 | Murray | G16B 20/00 |
| 2019/0272889 A1 | 9/2019 | Murray et al. | |
| 2019/0341152 A1 | 11/2019 | Mellem et al. | |
| 2019/0355439 A1 | 11/2019 | Murray | |
| 2019/0355474 A1 | 11/2019 | Mellem | |
| 2019/0385711 A1* | 12/2019 | Shriberg | G16H 10/20 |
| 2020/0143922 A1* | 5/2020 | Chekroud | G06K 9/6218 |

FOREIGN PATENT DOCUMENTS

| | | |
|---|---|---|
| WO | 2017106770 A1 | 6/2017 |
| WO | 2018029679 A1 | 2/2018 |
| WO | 2018074996 A1 | 4/2018 |
| WO | 2018170492 A1 | 9/2018 |
| WO | 2019070721 A1 | 4/2019 |
| WO | 2019070745 A1 | 4/2019 |
| WO | 2019213221 A1 | 11/2019 |
| WO | 2020047224 A1 | 3/2020 |
| WO | 2020047253 A1 | 3/2020 |

OTHER PUBLICATIONS

Kessler, R. C. et al.; "Screening for Serious Mental Illness in the General Population"; Arch. Gen. Psychiatry, vol. 60, pp. 184-189; Feb. 2003 (6 pages).

Kessler, R. C. et al.; "The WHO World Mental Health (WMH) Surveys"; Psychiatrie (Stuttg.), vol. 6, No. 1, pp. 5-9; Jan. 1, 2009 (6 pages).

White, P.D. et al.; "Time to end the distinction between mental and neurological illnesses"; BMJ, Jun. 16, 2012; vol. 344, pp. 26-28 (3 pages).

Letham, B. et al.; "Interpretable Classifiers Using Rules and Bayesian Analysis: Building a Better Stroke Prediction Model"; Annals of Applied Statistics, vol. 9, No. 3, pp. 1350-1371; Institute of Mathematical Statistics 2015 (23 pages).

Molnar, C., "Interpretable Machine Learning: A Guide for Making Black Box Models Explainable: Chapter 4, Interpretable Models"; publication date unknown (82 pages).

Webb, C. et al.; "Personalized prediction of antidepressant v. placebo response: evidence from the EMBARC study"; Psychological Medicine, 1-10; Jul. 2018; https://doi.org/10.1017/S0033291718001708 (11 pages).

Pampouchidou, A. et al.; "Depression Assessment by Fusing High and Low Level Features from Audio, Video, and Text"; Oct. 16, 2016; AVEC 2016; DOI: 10.1145/2988257.2988266 (8 pages).

Valstar, M. et al.; "AVEC 2016—Depression, Mood, and Emotional Recognition Workshop and Challenge"; Proceedings of the 6th International Conference on Multimedia (ACM MM), Oct. 2016, Amsterdam, Netherlands, pp. 3-10; DOI: 10.1145/2988257.2988258 (9 pages).

International Search Report and Written Opinion of International Searching Authority for Application No. PCT/US2018/054009, dated Feb. 4, 2019 (21 pages).

Komorowski, A. et al.; "Association of Protein Distribution and Gene Expression Revealed by PET and Post-Mortem Quantification in the Serotonergic System of the Human Brain"; Cerebral Cortex, vol. 27, No. 1, pp. 117-130; Nov. 30, 2016 (14 pages).

Yan, J. et al.; "Transcriptome-guided amyloid imaging genetic analysis via a novel structured sparse learning algorithm"; Bioinformatics, vol. 30, No. 17, pp. i564-i571; Sep. 1, 2014 (8 pages).

ntemational Search Report and Written Opinion of International Searching Authority for Application No. PCT/US2019/057677, dated Feb. 11, 2020 (28 pages).

* cited by examiner if sex is male and age is adult then $\theta = 0.21$ else if class is 3rd then $\theta = 0.44$ else if class is 1st then $\theta = 0.96$ else $\theta = 0.88$

FIG. 1

Require: Data set $X$ with labels $Y$. User parameters $r_{max}$, $s_{min}$, $\mu_{min}$, and $M$.

1: Compute literal scores $\rho_{i,k}$ for each literal $i$ in $X$ and label category $k$ in $Y$
2: $R = \phi$;
3: for label $k \in Y$ do
4:     $R_k = \phi$;
5:     for literal $l \in X$ do
6:         if $\rho_{l,k} \geq \mu_{min}$ and $\text{supp}_k(l) \geq tS_{min}$ then
7:             $R_k \leftarrow R_k \cup \{l\}$
8:     for rule length $\eta \in \{1; \ldots ; r_{max} - 1\}$ do
9:         for rule $r \in R_k$ with $|r| = \eta$ do
10:            $\mu_{min} \leftarrow M$-th top score in $R_k$
11:            if $\mu_k(r) < m_k(\eta)$ then
12:                continue
13:            for literal $l \in X$ do
14:                $\hat{r} \leftarrow r \cup l$
15:                if $\mu_k(\hat{r}) \geq \mu_{min}$ and
                    $\text{supp}_k(\hat{r}) \geq s_{min}$ then
16:                    $R_k \leftarrow R_k \cup \{\hat{r}\}$
17: $R \leftarrow R \cup \{\text{top } M \text{ rules in } R_k \text{ sorted by score}\}$
18: return $R$

FIG. 2A

1: if *Chapsoc#13* is *True* and *Hypomanic#8* is *True* then *Patient* ($p_{patient} = 0.92$)

2: else if *BipolarII#1* is *False* and *Eysenck#11* is *False*
     and *Golden#1* is *False* then *HC* ($p_{HC} = 0.80$)

3: else if *BipolarII#1* is *False* and *Hopkins#56* is 0 then *HC* ($p_{HC} = 0.50$)

4: else if *BipolarII#2* is *False* and *Dickman#28* is *False*
     and *Hopkins#39* is 0 then *HC* ($p_{HC} = 0.50$)

5: else *Patient* ($p_{patient} = 0.91$)

FIG. 6

1: if *Barratt#12* is 2 and *Dickman#29* is *True*
   and *TCI#231* is *False* then *ADHD* ($p_{ADHD} = 0.64$)

2: else if *Dickman#22* is *True* and *Hypomanic#1* is *True*
   then *SCHZ* ($p_{SCHZ} = 0.72$)

3: else if *BipolarII#1* is *False* and *Chapsoc#9* is *True*
   then *HC* ($p_{HC} = 0.70$)

4: else *BD* ($p_{BD} = 0.44$)

FIG. 8

PRT outcome measures per block

- Response Bias: $\log b = \frac{1}{2} \log (\text{Rich}_{\text{correct}} \cdot \text{Lean}_{\text{incorrect}})/(\text{Rich}_{\text{incorrect}} \cdot \text{Lean}_{\text{correct}})$

- Discriminability: $\log d = \frac{1}{2} \log (\text{Rich}_{\text{correct}} \cdot \text{Lean}_{\text{correct}})/(\text{Rich}_{\text{incorrect}} \cdot \text{Lean}_{\text{incorrect}})$

- Reaction Time: Time between stimulus onset and subject's response

- High Rate Rich: $\text{Rich}_{\text{correct}}/\text{Rich}_{\text{correct}} + \text{Rich}_{\text{incorrect}}$

- High Rate Lean: $\text{Lean}_{\text{correct}}/\text{Lean}_{\text{correct}} + \text{Lean}_{\text{incorrect}}$

- Each outcome is available per Block (1, 2, or 3)

FIG. 13

Explainable Enrichment-generates
rules for patient selection

IF FERT Response Bias - Angry smaller then 0.84
AND HADS-A larger then 12
THEN BTRX Ind ⟶ P=0.789, CI=(0.586,0.936)

ELSE IF HAMA smaller then 16
AND HADS-D larger then 10
AND PRT Hit rate lean - Block 3 smaller then 0.68
THEN Rest ⟶ P=0.969, CI=(0.888,0.999)

ELSE Rest ⟶ P=0.545, CI=(0.340,0.743)

FIG. 19A

Explainable Enrichment-generates
rules for patient selection

IF PRT Response Bias - Block3 smaller then 0.21
AND HADS-A larger then 7
THEN Rest ⟶ P=0.866, CI=(0.763,0.967)

ELSE IF HAMA smaller then 14
AND HADS-D larger then 10
THEN PLA Ind ⟶ P=0.824, CI=(0.653,0.964)

ELSE Rest ⟶ P=0.789, CI=(0.586,0.936)

FIG. 20A

BTRX Indicated vs Rest (Non+PLA Indicated)

IF Age larger than 29
AND Tumor Necrosis Factor larger than 1.77
AND HADS-A smaller than 12
THEN BTRX IND → P=0.909, CI=(0.692,0.997)

ELSE IF Baseline MADRS larger than 30
AND HAMA smaller than 18
AND PRT RT Rich - Block 1 smaller than 743
THEN Rest → P=0.923, CI=(0.823,0.983)

ELSE IF HADS-A larger than 7
AND Tumor Necrosis Factor larger than 2.29
THEN BTRX IND → P=0.900, CI=(0.664,0.997)

ELSE BTRX IND → P=0.692, CI=(0.428,0.901)

FIG. 25A

IF TEPS9 larger than 3
AND HAMA11 is 0
AND HAMA7 is smaller than 2
THEN Rest ⟶ P=0.704, CI=(0.522, 0.857)

ELSE IF HAMD16 is 0

AND HAMD7 larger than 2

THEN KORA Ind ⟶ P=0.964, CI=(0.872, 0.999)

ELSE IF HAMA2 smaller than 2

AND HAMD1 smaller than 2

THEN REST ⟶ P=0.889, CI=(0.631, 0.997)

ELSE KORA Ind ⟶ P=0.880, CI=(0.398, 0.994)

FIG. 26A

IF TEPS-Total smaller than 56
AND PRT Block2 Rich Reaction Time larger than 427
AND HAMA larger than 11
THEN KORA Ind→ P=0.862, CI=(0.718, 0.960)

ELSE IF PRT Rich Hit Rate smaller than 0.76
THEN Rest→P=0.720, CI=(0.533, 0.874)

ELSE KORA Ind→ P=0.636, CI=(0.348, 0.878)

FIG. 27A

IF TEPS-TOTAL smaller than 56
AND PRT Block2 Rich RT larger than 427
AND HAMA larger than 11
THEN KORA Ind → P=0.862, CI=(0.718, 0.960)

ELSE IF PRT Rich Hit Rate smaller than 0.76
THEN Rest → P=0.720, CI=(0.533, 0.874)

ELSE KORA Ind → P=0.636, CI=(0.348, 0.878)

FIG. 28

SYSTEMS AND METHODS FOR SCREENING, DIAGNOSING, AND STRATIFYING PATIENTS

CROSS REFERENCE TO RELATED APPLICATIONS

This application claims priority to and the benefit of U.S. Provisional Patent Application No. 62/749,473, filed Oct. 23, 2018, entitled, "MCA-Based Rule Mining Enables Interpretable Inference in Clinical Psychiatry," and of U.S. Provisional Patent Application No. 62/864,283, filed Jun. 20, 2019, entitled, "Systems and Methods for Screening, Diagnosing and Stratifying Patients," the content of both of which are herein incorporated by reference in their entireties.

FIELD

The present disclosure is directed to system and methods for screening, diagnosing, and stratifying patients relating to neuropsychiatric diseases, including for recommending treatments.

BACKGROUND

The following description includes information that may be useful in understanding the present disclosure. It is not an admission that any of the information provided herein is prior art or relevant to the presently claimed disclosure, or that any publication specifically or implicitly referenced is prior art.

The use of machine learning tools for artificial intelligence (AI) applied to clinical psychiatry data sets have consistently increased in recent years, mostly due to the prevalence of algorithms that can ingest heterogeneous data sets and at the same time produce highly predictive models.

SUMMARY

While high predictability is indeed a desirable result, the healthcare community also requires that the abstractions generated by machine learning models are also interpretable, so experts can potentially incorporate new machine learning insights to currently classical tools, or even better, so experts can improve the performance of the abstraction by tuning the data-driven models. The present disclosure takes a practical approach towards solving this problem, both by developing a new algorithm capable of mining association rules from wide categorical datasets, and by applying a rule list generating algorithm to the mined rules to output predictable and interpretable models. These models then serve as transdiagnostic screening tools for psychiatric disorders.

According to some implementations of the present disclosure, interpretable machine learning methods are developed, which can provide accessible and explicit explanations to the artificial intelligence research community. Popular machine learning methods such as artificial neural networks and ensemble models are known for their elusive readout. For example, while artificial neural network applications exist for tumor detection in CT scans, it is virtually impossible for a person to understand the rationale behind such a mathematical abstraction.

Interpretability can be defined as not only understanding what a model emitted, but also why it did. In this context, straightforward linguistic explanations are frequently considered as the better option for interpretability when compared to examining coefficients of a linear model or evaluating the importance of perceptrons in artificial neural networks. Examples of interpretable machine learning models in healthcare include the development of a boosting method to create decision trees as the combination of single decision nodes. Bayesian Rule List ("BRL") models mix the interpretability of sequenced logical rules for categorical datasets, together with the inference power of Bayesian statistics. BRL algorithms output Bayesian Decision Lists that are a series of rules that can be used to classify data. Compared to decision trees, Bayesian Decision Lists take the form of a hierarchical series of if-then-else statements where model emissions correspond to the successful association to a given rule. BRL results in models that are inspired, and therefore similar, to standard human-built decision-making algorithms.

A plurality of models can be used to generate rules from which the actual rule lists are built. In some implementations, the plurality of models can include associative classification methods. In some implementations, a BRL model alone may be used. In some implementations, one or more of the plurality of models can incorporate frequent pattern mining as a tool to build such an initial set of rules. In some implementations, Apriori and/or FPGrowth can be used to extract rules from categorical datasets that the BRL model may then be applied to in order to generate rule lists. In some implementations, for wide datasets (e.g., datasets where the total number of categorical features is much larger than the number of samples, denoted as $p \gg n$), which can include clinical healthcare datasets, non-traditional mining methods are required to enable the power of BRL in this research area.

Accordingly, one of the models disclosed includes a rule mining technique that is not based on the frequency in which certain categories simultaneously appear. Instead, implementations described herein provide a new Multiple Correspondence Analysis (MCA), a particular application of correspondence analysis to categorical datasets, to establish a similarity score between different associative rules. Results show that this new MCA-miner method is significantly faster than commonly used frequent pattern mining methods, and that it scales well to wide datasets. Moreover, results have shown that new MCA-miner performs equally well than other miners when used together with BRL. Finally, the new MCA-miner and BRL are used to analyze a transdiagnostic dataset for psychiatric disorders, building both interpretable and accurate predictors to support clinician screening tasks.

Thus, disclosed herein are systems and methods for screening, diagnosing, and stratifying patients into treatment groups based on the disclosed rule lists. The models disclosed herein for stratifying patients include Bayesian Decision Lists that are identified by BRL Models. The BRL models may be applied to a set of rules identified by rule mining methods disclosed herein, including the newly developed MCA based rule miner. Furthermore, rule mining methods may be applied to a feature set identified using forward selection or other techniques.

In some examples, various models are able to classify patients utilizing various modalities combined together in relatively short rule lists, and these include features output from clinical scales questionnaires, task based psychological assessments, MRI data, and or others. In some examples, the scales and tasks are administered in tablets, computing devises, or mobile devices and the input from the user interface is translated into features that may be utilized by the models.

According to some implementations of the present disclosure, the disclosed models demonstrated surprising results. For example, many of the models are able to accurately screen, diagnose, or stratify patients using rule lists. For instance, models disclosed herein using only scales, and a few questions from various known scales assessments can be utilized to screen patients using the methods and systems disclosed herein.

In some cases, some model and modality combinations stratify patients based on multiple modalities—rather than a single modality. Furthermore, the results indicate that in some circumstances, models that take input from multiple modalities may be more accurate—for instance combinations of scales and task based modalities to stratify patients—than models that utilized a single modality.

According to some implementations of the present disclosure, a system for evaluating a patient for mental health issues includes a display device, a user interface, a memory, and a control system. The memory contains machine readable medium. The machine readable medium includes machine executable code storing instructions for performing a method. The control system is coupled to the memory, and includes one or more processors. The control system is configured to execute the machine executable code to cause the control system to display, on the display device, a series of questions from mental health questionnaires. The series of questions includes text and answers for each question. From the user interface, a selection of answers of each of the displayed series of questions is received from a patient. Using a Bayesian Decision List, the received selection of answers is processed to output an indication of mental health of the patient.

In some implementations, the indication of mental health includes whether the patient has bi-polar disorder, ADHD, schizophrenia, or any combination thereof. In some implementations, the indication of mental health includes determining whether the patient has a mental disorder. In some implementations, the indication of mental health includes identifying at least two mental health conditions based at least in part on determining that the patient exceeds a threshold probability of having each of the at least two health conditions. In some implementations, the indication of mental health includes whether the patient has OCD, PTSD, autism, or any combination thereof. In some implementations, the indication of mental health identifies a drug to which the patient would likely be a higher responder.

In some implementations, the Bayesian Decision List is generated by receiving labeled training data comprising data for a plurality of individuals. The labeled training data includes category labels indicative of whether each of the plurality of individuals has one or more mental health disorders. The labeled training data further includes a plurality of attributes. Based at least in part on the received labeled training data, a plurality of rules is generated. The plurality of rules predicts a category label associated with a set of attributes. A score is calculated for each of the generated plurality of rules. The score is representative of a capacity to predict the category label. One or more rules of the generated plurality of rules are eliminated based at in part on a threshold capacity to predict the category label. A Bayesian Decision List designed to predict the category label is generated using the rules that are not eliminated from the plurality of rules.

According to some implementations of the present disclosure, a system for evaluating a patient for mental health issues includes a display device, a user interface, a memory, and a control system. The memory contains machine readable medium. The machine readable medium includes machine executable code storing instructions for performing a method. The control system is coupled to the memory, and includes one or more processors. The control system is configured to execute the machine executable code to cause the control system to display, on the display device, a series of questions from mental health questionnaires. The series of questions includes text and answers for each question. From the user interface, a selection of answers of each of the displayed series of questions is received from a patient. A set of MRI data associated with a brain of the patient is received from a magnetic resonance imaging (MRI) device. Using a Bayesian Decision List, the received selection of answers and the set of MRI features are processed to output an indication of mental health of the patient. In some implementations, the received MRI data is resting-state functional MRI data, structural MRI data, or both.

According to some implementations of the present disclosure, a system for evaluating a patient for mental health issues includes a display device, a user interface, a memory, and a control system. The memory contains machine readable medium. The machine readable medium includes machine executable code storing instructions for performing a method. The control system is coupled to the memory, and includes one or more processors. The control system is configured to execute the machine executable code to cause the control system to display, on the display device, a series of questions from mental health questionnaires. The series of questions includes text and answers for each question. From the user interface, a selection of answers of each of the displayed series of questions is received from a patient. A series of images is displayed on the display device. A selected response from the patient is received from the user interface for each of the displayed series of images. A set of selected responses is outputted. Using a model, the received selection of answers and the set of selected responses processed to output an indication of mental health of the patient.

In some implementations, the model is a Bayesian Decision List. In some implementations, the Bayesian Decision List is generated based at least in part on features identified using forward selection. In some implementations, the model is a linear regression model. In some implementations, the model is a logistical regression model. In some implementations, the model is a machine learning model. In some implementations, the model includes a machine learning model and a set of features. The set of features is determined using forward selection.

In some implementations, each of the displayed series of images includes a face with a predetermined emotional expression. The selected response for each of the displayed series of images corresponds to an emotion selected by the patient. In some implementations, the emotion is anger.

In some implementations, the selected response for each of the displayed series of images includes a patient identification of the image. In some implementations, the selected response for each of the displayed series of images further includes whether the selected image illustrates a long or short mouth.

In some implementations, the indication of mental health identifies a drug to which the patient would likely be a higher responder. In some examples, the drug is BTRX-246040. In some examples, the drug is a nociceptin receptor antagonist (NOPA). In some examples, the drug is CERC-501. In some examples, the drug is a kappa opioid receptor antagonist (KORA). In some implementations, the indication of mental health includes whether the patient will respond to a placebo.

According to some implementations of the present disclosure, a system for evaluating a patient for mental health issues includes a display device, a user interface, a memory, and a control system. The memory contains machine readable medium. The machine readable medium includes machine executable code storing instructions for performing a method. The control system is coupled to the memory, and includes one or more processors. The control system is configured to execute the machine executable code to cause the control system to display, on the display device, a series of questions from mental health questionnaires. The series of questions includes text and answers for each question. From the user interface, a selection of answers of each of the displayed series of questions is received from a patient. Instructions are displayed on the display device for the patient to perform a goal series of user interface inputs. An actual series of user interface inputs is received from the user interface. Using a model, the received selection of answers and the received actual series of user interface inputs are processed to output an indication of mental health of the patient.

In some implementations, the model includes a machine learning model and a set of features. The set of features is determined using forward selection with a logistical regression model using elastic net regularization. In some implementations, the goal series of user interface inputs includes a series of mouse clicks within a time frame. In some implementations, the goal series of user interface inputs includes touching a position on a screen of the user interface where a graphic icon is previously displayed.

In some implementations, the machine learning model is generated by receiving labeled training data comprising data for a plurality of individuals. A plurality of features is generated based at least in part on the received labeled training data. An initial machine learning model is trained in a supervised manner, based at least in part on the generated plurality of features. Importance measures are extracted for each of the generated plurality features, based at least in part on the training of the initial machine learning model. A plurality of subset machine learning models is generated, based at least in part on the extracted importance measures for each of the plurality of features. A classification performance of the generated plurality of subset machine learning models is evaluated. At least one of the subset machine learning models is selected as the linear regression model.

The present disclosure further includes a method of building a rule list for data sets with a large total number of categories among many attributes for machine learning models. A data set is obtained by a computer. The data set includes a plurality of attribute statements for a plurality of label categories. A data table of attribute statements and label categories is generated. Each element of the data table is representative of a corresponding combination of an attribute statement of the obtained plurality of attribute statements and a label category of the obtained plurality of label categories. A score is calculated, by the computer, for each element of the generated data table.

For each subset of the generated data table associated with a first target label category, whether a first calculated score for a first element of the subset exceeds a first user-defined threshold is determined. Whether support for a corresponding attribute statement associated with the first element exceeds a second user-defined threshold is determined. Responsive to determining that (i) the first calculated score for the first element exceeds the first user-defined threshold and that (ii) support for the attribute statement associated with the first element exceeds the second user-defined threshold, a rule set is updated for the target label category. The first user-defined threshold is updated to a maximum score in the rule set for the target label category. A new rule is set by the computer as a target rule associated with a next element of the subset. Responsive to a determination that (i) a second calculated score between the new rule and the target label category exceeds the updated first user-defined threshold and that (ii) support for the new rule is greater than the second user-defined threshold new rule is set as a target rule associated with a next element of the subset, the rule set for the target label category is updated, by the computer, to include the new rule. The rule set associated with the data set is updated, by the computer, for a top threshold number of rules sorted by score.

A computing system includes one or more databases, a memory, and a processor. The one or more databases store clinical scale data. The memory store computer instructions. The processor is configured to execute the stored computer instructions to obtain a data set. The data set includes a plurality of attribute statements for a plurality of label categories. A data table of attribute statements and label categories is generated. Each element of the data table is representative of a corresponding combination of an attribute statement of the obtained plurality of attribute statements and a label category of the obtained plurality of label categories. A score is calculated for each element of the generated data table.

For each target label category in the plurality of categories, a rule set for the target category to include the target attribute statement is updated for each target attribute statement of the plurality of attribute statements. The rule set for the target category is updated responsive to a determination that (i) the calculated score for the element associated with the target attribute statement is greater than a first user-defined threshold and (ii) support for the target attribute statement is greater than a second user-defined threshold. The rule set for the target category includes a plurality of rules.

For each target rule of the plurality of rules in the rule set, the first user-defined threshold updated to a maximum score in the rule set for the target category. For each target attribute statement of the plurality of attribute statements, a new rule is set as the target rule with the target attribute statement. The rule set for the target category is updated to include the new rule responsive to a determination that (i) a new score between the new rule and the target category is above the updated first user-defined threshold and (ii) support for the new rule is greater than the second user-defined threshold. The rule set associated with the data set is updated for a top threshold number of rules sorted by score.

A system for evaluating a patient for mental health issues includes a display device, a user interface, a memory, and a control system. The user interface includes a speaker and a microphone. The memory includes machine readable medium comprising machine executable code storing instructions for performing a method. The control system is coupled to the memory, and includes one or more processors. The control system is configured to execute the machine executable code to cause the control system to output, through the speaker, a series of questions from mental health questionnaires comprising in an audio format. An audio recording of a patient's selection of answers of each of the series of questions is received. The patient's selection of answers is processed, using a Bayesian Decision List, to output an indication of mental health of the patient.

A system for screening the mental health of patients includes a display, a microphone, a camera, a user interface, a memory, and a control system. The camera is positioned to capture an image in front of the display. The camera is further configured to output video data. The memory contains machine readable medium comprising machine executable code. The machine executable code stores instructions for performing a method of evaluating the mental health of a user. The control system is coupled to the memory, and includes one or more processors. The control system is configured to execute the machine executable code to cause the control system to execute a test application.

The test application is executed by the control system upon receiving, from the user interface, an indication to initiate a test. The test application is terminated upon receiving, by the control system, an indication to stop the test. The test application includes displaying, on the display, a series of questions from mental health questionnaires. The mental health questionnaires include text and answers for each question. Live video data recorded by the camera is displayed on the display. A set of test video data is recorded by the camera. A set of test audio data is recorded by the microphone. An answer for each of the series of questions is received, through the user interface, to yield a selection of answers. The selection of answers, the set of test video data, and the set of audio data are processed, using a Bayesian Decision List, to output a mental health indication of the user.

A system for screening the mental health of patients includes a microphone, a speaker, a memory, and a control system. The memory contains machine readable medium comprising machine executable code storing instructions for performing a method of evaluating the mental health of a user. The control system is coupled to the memory, and includes one or more processors. The control system is configured to execute the machine executable code to cause the control system to execute a test application. The test application is executed by the control system upon receiving, from the user interface, an indication to initiate a test. The test application is terminated upon receiving, by the control system, an indication to stop the test. The test application includes outputting, through the speaker, a series of questions comprising audio data. A set of test audio data is recorded by the microphone. The set of audio data is processed, using a Bayesian Decision List, to output a mental health indication of the user.

In some implementations, the set of test audio data includes an audio recording of the patient reciting a statement provided to the patient. In some implementations, the set of test audio data includes answers to a set of questions from mental health questionnaires. In some implementations, the series of questions includes a request for the patient to recite a statement. In some implementations, the series of questions comprises open ended questions.

In some implementations, processing the set of audio data includes identifying at least one of the following audio features: local features, global waveform level features, phoneme rate, demographics, duration, speaking ratio, voice ratio, prosodic features, glottal and spectral features. In some implementations, processing the set of audio data includes identifying features from the patient's voice extracted from the set of audio data or identifying text features from the words extracted from the set of audio data.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The accompanying drawings, which are incorporated in and constitute a part of this specification, exemplify the implementations of the present disclosure and, together with the description, serve to explain and illustrate principles of the disclosure. The drawings are intended to illustrate major features of the example implementations in a diagrammatic manner. The drawings are not intended to depict every feature of actual implementations nor relative dimensions of the depicted elements, and are not drawn to scale.

FIG. 1 depicts a Bayesian Decision List output from a BRL model on a Titanic survival data set, wherein $\theta$ denotes a probability of survival, according to some implementations of the present disclosure;

FIG. 2A depicts a pseudocode of a MCA-based rule mining algorithm, according to some implementations of the present disclosure;

FIG. 6 depicts a rule list for a transdiagnostic screening of psychiatric disorders, classifying between Healthy Controls vs. Patients, according to some implementations of the present disclosure;

FIG. 8 depicts a concise rule list as a psychiatric transdiagnostic tool, according to some implementations of the present disclosure;

FIG. 13 depicts equations utilized to measure the outcomes in a PRT task, according to some implementations of the present disclosure;

FIG. 19A depicts a pseudocode for a BRL output using a disclosed rule mining technique and a BRL model, according to some implementations of the present disclosure;

FIG. 20A depicts another pseudocode for a BRL output using a disclosed rule mining technique and a BRL model, according to some implementations of the present disclosure;

FIG. 25A depicts a further pseudocode for a BRL output incorporating Tumor Necrosis Factor into the rule list, according to some implementations of the present disclosure;

FIG. 26A depicts yet another pseudocode for a BRL output using a disclosed rule mining technique and a BRL model, according to some implementations of the present disclosure;

FIG. 27A depicts yet a further pseudocode for a BRL output using a disclosed rule mining technique and a BRL model, according to some implementations of the present disclosure;

FIG. 28 depicts an additional pseudocode for a BRL output using a disclosed rule mining technique and a BRL model, according to some implementations of the present disclosure;

Figure 2B:
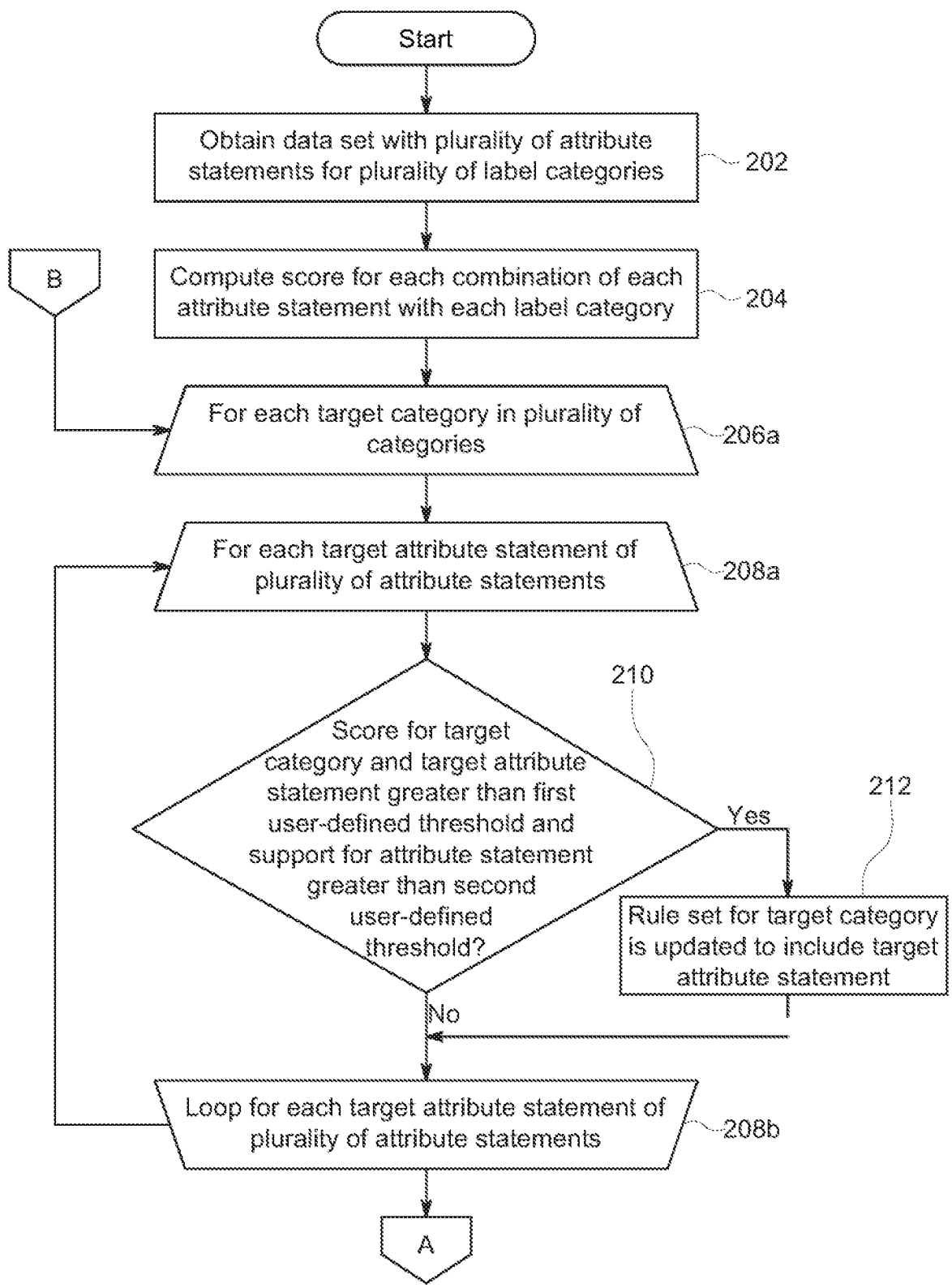
FIG. 2B depicts a flow chart illustrating a portion of the MCA-based rule mining algorithm of FIG. 2A, according to some implementations of the present disclosure.

In the drawings, the same reference numbers and any acronyms identify elements or acts with the same or similar structure or functionality for ease of understanding and convenience. To easily identify the discussion of any particular element or act, the most significant digit or digits in a reference number refer to the figure number in which that element is first introduced.

DETAILED DESCRIPTION

The present disclosure is described with reference to the attached figures, where like reference numerals are used throughout the figures to designate similar or equivalent elements. The figures are not drawn to scale, and are provided merely to illustrate the instant disclosure. Several aspects of the disclosure are described below with reference to example applications for illustration. It should be understood that numerous specific details, relationships, and methods are set forth to provide a full understanding of the disclosure. One having ordinary skill in the relevant art, however, will readily recognize that the disclosure can be practiced without one or more of the specific details, or with other methods. In other instances, well-known structures or operations are not shown in detail to avoid obscuring the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

Aspects of the present disclosure can be implemented using one or more suitable processing device, such as general-purpose computer systems, microprocessors, digital signal processors, micro-controllers, application-specific integrated circuits (ASIC), programmable logic devices (PLD), field-programmable logic devices (FPLD), field-programmable gate arrays (FPGA), mobile devices such as a mobile telephone or personal digital assistants (PDA), a local server, a remote server, wearable computers, tablet computers, or the like.

Memory storage devices of the one or more processing devices can include a machine-readable medium on which is stored one or more sets of instructions (e.g., software) embodying any one or more of the methodologies or functions described herein. The instructions can further be transmitted or received over a network via a network transmitter receiver. While the machine-readable medium can be a single medium, the term "machine-readable medium" should be taken to include a single medium or multiple media (e.g., a centralized or distributed database, and/or associated caches and servers) that store the one or more sets of instructions.

The term "machine-readable medium" can also be taken to include any medium that is capable of storing, encoding, or carrying a set of instructions for execution by the machine and that cause the machine to perform any one or more of the methodologies of the various embodiments, or that is capable of storing, encoding, or carrying data structures utilized by or associated with such a set of instructions. The term "machine-readable medium" can accordingly be taken to include, but not be limited to, solid-state memories, optical media, and magnetic media. A variety of different types of memory storage devices, such as a random access memory (RAM) or a read-only memory (ROM) in the system or a floppy disk, hard disk, CD ROM, DVD ROM, flash, or other computer-readable medium that is read from and/or written to by a magnetic, optical, or other reading and/or writing system that is coupled to the processing device, can be used for the memory or memories.

Overview

While many black box algorithms exist that are able to stratify patients and identify appropriate treatments, clinicians cannot determine the basis for the decisions made by the algorithm and therefore validate the choices. This is particularly difficult, because certain regulations require doctors to validate the decision of clinical support systems in order to pass regulatory scrutiny, and generally validate that the approach is clinically sound. With a black box machine learning algorithm, clinicians would understand little more than what features (in some cases) were the input, but not which features were the most important. For deep learning algorithms, the features identified may not even be apparent, and therefore the only knowledge a clinician may have about the decision is what types of data were input into the algorithm and/or were used to train it.

While some interpretable and/or explainable algorithms exist, they may only be limited to one type of data (e.g. one modality, such as clinical scales) and/or may be overly complex, and therefore not useful. Furthermore, they generally are types of algorithms such as decision trees that may not be as accurate, and/or only have the ability to take into account a fraction of the features and/or attributes that could be useful. Additionally, developing interpretable classification algorithms in the neurobehavioral space is challenging given the large number of biotypes within certain neurobehavioral classifications (e.g., depression, schizophrenia, and/or other indications). Thus, it can be extraordinarily difficult to develop an explainable algorithm that would be understandable by a human, taking into account multiple modalities and/or sources of data, yet still accurate enough to be useful.

Accordingly, systems and methods disclosed herein provide for stratifying patients in the neurobehavioral space using, for example, multiple modalities and/or short interpretable algorithms. These algorithms are able to process an extraordinary amount of features and/or attributes, but only output a relatively short rule list that is easily interpretable, yet still classifies patients with accuracy.

According to some implementations of the present disclosure, some of these rule lists also take into account multiple modalities including clinical scales questions, tasks, wet biomarkers, or the like, or any combination thereof. This is very advantageous and unexpected, because balancing multiple modalities and/or the number of different features is extraordinarily difficult to understand how they interact, and the disclosed models are able to incorporate them into the rule lists.

Furthermore, these rule lists are able to identify higher responders to certain neurobehavioral drugs that would otherwise be applied broadly to patients generally diagnosed according to the Diagnostic and Statistical Manual of Mental Disorders ("DSM") categories (e.g. depression, schizophrenia, etc.). In some cases, the neurobehavioral drugs did not show an improved response over the placebo when applied to patients classified broadly in the DSM categories, but they did when classified using the disclosed rule lists. This is very advantageous, as these rule lists allow these drugs to be given to the right patients, they are interpretable, and the rule list are short enough to be efficient and practical when applied. Thus, this represents an entirely new paradigm in the stratification of patients in the neurobehavioral space.

Accordingly, the disclosed systems and methods are able to analyze categorical datasets with a large number of attributes—a property that is prevalent in the clinical psychiatry community. Particularly, the disclosed systems and methods may utilize a rule mining method that outputs a set of rules, and/or a Bayesian Rule List model that processes the set of rules and generates Bayesian Decision Lists or rule lists that may be utilized to classify patients. Furthermore, in some examples, a feature selection method may first identify the most important features before a rule mining method is applied to the features.

Decision List Generation

According to some implementations of the present disclosure, decision lists are generated that stratify patients into different categories. One or more "if → then" statements are applied to specific input features. These decision lists are easily understandable by clinicians and thus may be easily validated. Disclosed herein are examples of how these decision lists may be generated.

In some examples, the disclosed systems and methods utilize one or more of the following models to generate decision lists: (i) feature selection models, (ii) rule mining models, and (iii) Bayesian Rule List models. In some examples, only rule mining models and Bayesian Rule list models may be utilized. In other examples, only Bayesian Rule list models may be utilized to generate a rule list to stratify patients.

Bayesian Rule Lists Models

Bayesian Rule List models ("BRL model" and/or "BRL algorithm") are a framework proposed by Letham et al. in "Interpretable Classifiers Using Rules and Bayesian Analysis: Building a Better Stroke Prediction Model," Annals of Applied Statistics, Vol. 9, No. 3 2015, the content of which is incorporated herein by reference in its entirety. The BRL model may be utilized to build lists of rules for data sample classification. An example of a BRL model output trained on a commonly used Titanic survival data set, is depicted in FIG. 1. As shown, FIG. 1 illustrates a pseudo-code showing a Bayesian Decision List output from a BRL model on a Titanic survival data set, wherein θ denotes a probability of survival.

An additional example of BRL models is described in a book by Christoph Molnar "Interpretable Machine Learning, *A Guide for Making Black Box Models Explainable*," Chapter 4, Interpretable Models, the content of which is incorporated herein by reference in its entirety. As described by Molnar, BRL models generate a decision list using a selection of pre-mined rules, and in many cases prioritizing few rules and short conditions for each rule. This may be performed by defining a distribution of decision lists with prior distributions for the length of conditions and the number of rules. The posteriori probability distribution of lists allows the model to evaluate potential decision lists for their probability. In some examples, the model identifies a decision list that maximizes the posterior probability.

In some examples, the BRL model will: (i) generate an initial decision list randomly drawn from a priori distribution list; (ii) iteratively modify the initial decision list by adding, removing, or moving rules in the list, as long as the new list follows the posterior distribution of lists; and (iii) select the modified list with the highest probability according to the posteriori distribution.

In some examples, and specifically, the BRL model may be applied to a set of rules that were pre-mined using an FP-Growth algorithm, a MCA rule miner disclosed herein, and/or other rule mining techniques. The BRL model may rely on assumptions about the distribution of the output label, and/or the distribution of the parameters that define the distribution of the output label.

Thus, the Bayesian approach combines existing knowledge or requirements (so-called priori distributions) while also fitting to the data. In the case of decision lists, the Bayesian model favors decision lists to be short with short rules. In some examples, the goal is to sample decision lists from the posteriori distribution:

$$\underbrace{p(d \mid x, y, A, \alpha, \lambda, \eta)}_{posteriori} \propto \underbrace{p(y \mid x, d, \alpha)}_{likelihood} \cdot \underbrace{p(d \mid A, \lambda, \eta)}_{priori}$$

where d is a decision list, x is the features, y is the output, A is the set of pre-mined conditions, λ is the prior expected length of the decision lists, η is the prior expected number of conditions in a rule, a is the prior pseudo-count for the positive and negative classes which is best fixed at (1,1).

In some examples, the following equation represents the probability of a decision list, given the data and priori assumptions:

$$p(d \mid x, y, A, a, \lambda, \eta)$$

This is proportional to the likelihood of the outcome y given the decision list and the data, times the probability of the list given prior assumptions and the pre-mined conditions.

In some examples, the following equation represents the likelihood of the outcome y, given the decision list and data:

$$p(y \mid x, d, a)$$

BRL may assume that y is generated by a Dirichlet-Multinomial distribution. The better the decision list "d" explains the data, the higher the likelihood.

In some examples, the following equation represents the prior distribution of the decision lists.

$$P(d \mid A, \lambda, \eta)$$

The equation may combine a truncated Poisson distribution (parameter λ) for the number of rules in the list and a truncated Poisson distribution (parameter η) for the number of feature values in the conditions of the rules. A decision list has a high posterior probability if it explains the outcome y well, and is also likely according to the prior assumptions.

According to some implementations of the present disclosure, estimations in Bayesian statistics may be performed by first drawing candidates, evaluating them, and updating posteriori estimates using a Markov chain Monte Carlo method. For decision lists, one or more lists from the distribution of decision lists are drawn. The BRL model may first draw an initial decision list, and iteratively modify it to generate samples of decision lists from the posterior distribution of the lists (e.g., a Markov chain of decision lists). The results are potentially dependent on the initial decision list, so it is advisable to repeat this procedure to ensure a great variety of lists. For example, a default number of iterations in a software implementation is ten times.

In some examples, one or more of the following steps may be utilized to identify an initial decision list:
1) Pre-mine patterns or a set of rules;
2) Sample the list length parameter m from a truncated Poisson distribution;
3) For the default rule: Sample the Dirichlet-Multinomial distribution parameter of the outcome value (e.g. the rule that applies when nothing else applies);
4) For decision list rule j=1, . . . , m:
   a. Sample the rule length parameter l (number of conditions) for rule j;
   b. Sample a condition of length $l_j l_j$ from the pre-mined conditions;
   c. Sample the Dirichlet-Multinomial distribution parameter for the THEN-part (e.g. for the distribution of the target outcome given the rule);
5) For each observation in the dataset:
   a. Find the rule from the decision list that applies first (top to bottom);

b. Draw the predicted outcome from the probability distribution (Binomial) suggested by the rule that applies.

Once the initial decision list is identified, the BRL model may generate many new lists starting from the identified initial list (e.g., an initial sample) to obtain many samples from the posterior distribution of decision lists.

Markov Chain Monte Carlo Sampling ("MCMC")

According to some implementations of the present disclosure, Metropolis-Hastings sampling of d may be performed. Particularly, the new decision lists may be sampled by starting from the initial list and then randomly making one or more modifications. The one or more modifications include (i) moving a rule to a different position in the list, (ii) adding a rule to the current decision list from the pre-mined conditions, (iii) removing a rule from the decision list, or (iv) any combination thereof. In some implementations, which of the rules is switched, added, or deleted is chosen at random. In some implementations, the algorithm evaluates the posteriori probability of the decision list (e.g., accuracy, shortness, or both) at each step.

In some examples, the BRL model may utilize various algorithms to ensure that the sampled decision lists have a high posterior probability. This procedure provides many samples from the distribution of decision lists. The BRL algorithm may select the decision list of the samples with the highest posterior probability.

Rule Mining Models

According to some implementations of the present disclosure, a set of rules is first mined from a data set. For instance, as disclosed in Letham et al. (2015) and referenced herein, an FP growth miner is used for first mining a set of rules from a data set. The BRL model searches over a configuration space of combinations of the prescribed set of rules using an MCMC algorithm or other suitable algorithms as disclosed herein. In some implementations, rule mining methods may be utilized to generate a set of rules that a BRL model may process to generate and output a decision list. In some such implementations, the rule mining methods include an MCA based rule mining method.

The MCA-based rule mining method can include one or more scaling properties against a plurality of categorical attributes, and may utilize a new implementation of the BRL algorithm using multi-core parallel execution. This new implementation using multi-core parallel execution was applied to the CNP dataset for psychiatric disorders and resulted n rule-based interpretable classifiers capable of screening patients using self-reported questionnaire data (e.g. scales data). The results not only show the viability of building interpretable models for state-of-the-art clinical psychiatry datasets, but also that these models can be scaled to larger datasets to understand the interactions and differences between these disorders.

Relevant notations and definitions used throughout this disclosure is introduced. An attribute, denoted a, is a categorical property of each data sample, which can take a discrete and finite number of values, denoted $|a|$. A literal is a Boolean statement checking if an attribute takes a given value, e.g., given an attribute a with categorical values $\{c1, c2\}$, the following literals can be defined: a is c1, and a is c2. Given a collection of attributes $\{a_1\}_{i=1}^{P}$, a data sample is a list of categorical values, one per attribute. A rule, denoted r, is a collection of literals, with length $|r|$, which is used to produce Boolean evaluations of data samples as follows: a rule evaluates to True whenever all the literals are also True, and evaluates to False otherwise.

This disclosure considers the problem of efficiently building rule lists for data sets with a large total number of categories among all attributes (e.g., $\Sigma_{i=1}^{P}|a_i|$), a common situation among data sets related to health care or pharmacology including neurobehavioral health disorders.

In one example, given n data samples, a data set can be represented as a matrix X with dimensions $n \times p$, where $X_{i,j}$ is the category assigned to the i-th sample for the j-th attribute. A categorical label for each data sample is also considered, collectively represented as a vector Y with length n. The number of label categories is denoted by l, where $l \geq 2$. If $l=2$ then a standard binary classification problem is present. If, instead, $l>2$ then a multi-class classification problem is solved.

Conventional rule mining methods often fail to execute on data sets with a large total number of categories, due to either unacceptably long computation time or prohibitively high memory usage. This present disclosure includes a novel rule mining model based on Multiple Correspondence Analysis ("MCA") that is both computational and memory efficient, enabling the application of a BRL model on datasets with a large total number of categories.

Figure 4:
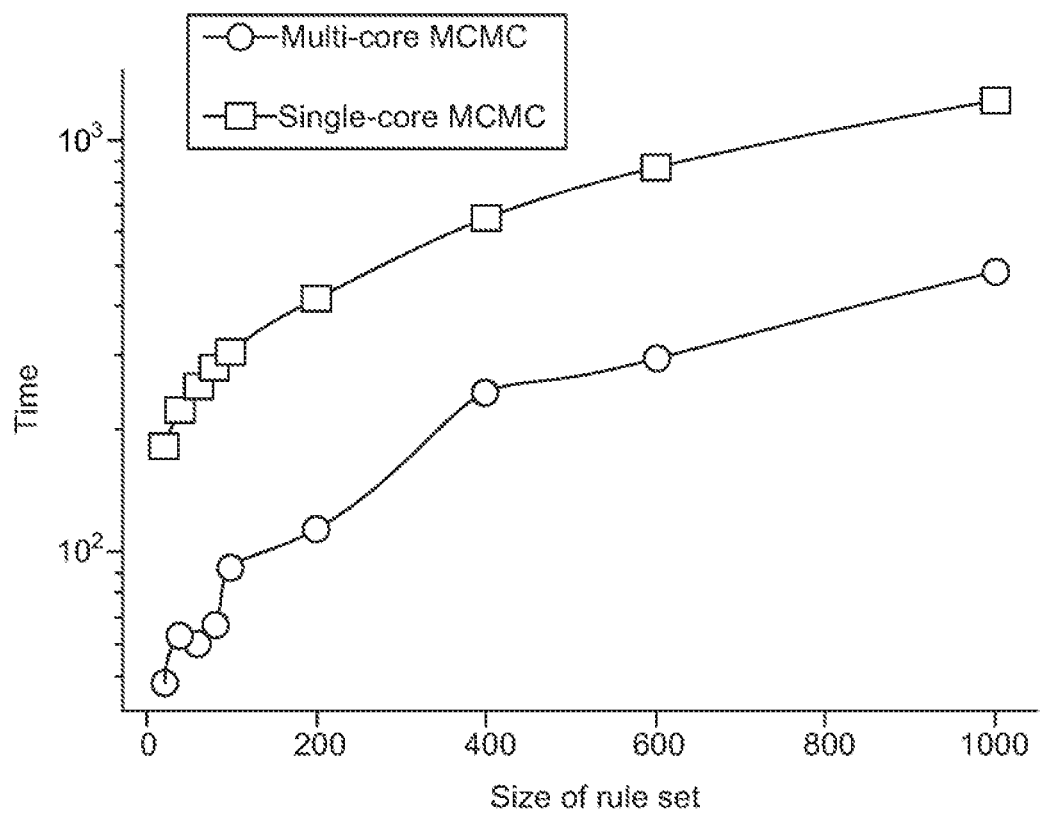
FIG. 4 depicts a graph of a MCMC convergence wall execution time comparison between single- and multi-core implementations, as a function of rule set size, according to some implementations of the present disclosure.

According to some implementations of the present disclosure, an MCMC search method in the BRL model may be parallelized by executing individual Markov chains in separate CPU cores of a computer. In some implementations, the convergence of multiple chains may be periodically checked using a generalized Gelman & Rubin convergence criteria, thereby stopping the execution once the convergence criteria is met. As shown in FIG. 4, for example, this implementation is faster than the original single-core version, enabling the study of more data sets with longer rules and/or a large number of features.

MCA is a method that applies the power of Correspondence Analysis ("CA") to categorical data sets. According to some implementations of the present disclosure, MCA is an application of CA to an indicator matrix of all categories in a set of attributes, thereby generating principal vectors projecting each of those categories into a Euclidean space. The generated principal vectors are used to build a heuristic merit function over the set of all available rules given the categories in a data set. Moreover, the structure of the merit function allows for efficient mining of the best rules.

Rule Score Calculation

In some implementations, a methodology is disclosed for determining a score related to a usefulness of a rule and/or any number of rules. However, any other suitable methodologies may be utilized.

An extended data matrix may be defined as concatenating X and Y, denoted $Z=[X\ Y]$ with dimensions $n \times (p+1)$. The MCA principal vectors are computed for each category present of Z. The MCA principal vectors associated with corresponding categorical values are called categorical vectors, denoted by $\{v_j\}_{j=1}^{\Sigma_i |a_i|}$, where $\{a_i\}_{i=1}^{P}$ is a set of attributes in a data set X. The MCA principal vectors associated with corresponding label categories are called label vectors, denoted by $\{w_k\}_{k=1}^{l}$.

Each category can be mapped to a literal statement. The principal vectors serve as a heuristic to evaluate a quality of a given literal to predict a label. Therefore, a score between each categorical vector $v_j$ and each label vector $\omega_k$ is calculated as a cosine of their angle:

$$p_{j,k} = \cos \angle(V_j, \omega_k) = \frac{\langle V_j, \omega_k \rangle}{\|v_j\|_2 \|\omega_k\|_2} \qquad (1)$$

In the context of random variables, $p_{j,k}$ is equivalent to the correlation between the two principal vectors.

The score between a rule r and label category k is calculated, and denoted $\mu_k(r)$, as the average among the scores between the literals in r and the same label category, e.g.:

$$\mu_k(r) = \frac{1}{|r|} \sum_{l \in r} \rho l, k. \quad (2)$$

The configuration space of rules r built using the combinations of all available literals in a data set is searched such that $|r| \le r_{max}$, and those with highest scores for each label category are identified. These top rules are the output of disclosed miner, and are passed over to the BRL method as the set of rules from which rule lists will be built.

Rule Pruning

In some implementations, the number of rules generated by all combinations of all available literals up to length $r_{max}$ can be large even for modest values of $r_{max}$, the disclosed technology may include different methods of pruning and/or eliminating a portion of the generated rules. In some such implementations, for example, the present disclosure includes two conditions under which rules are efficiently eliminated from consideration.

First, rules whose support over each label category is smaller than a user-defined threshold $s_{min}$ can be eliminated. The support of a rule r for label category k, denoted suppk(r), is the fraction of data samples that the rule evaluates to True among the total number of data samples associated to a given label. Given a rule r, note that the support of every other rule r̂ containing the collection of literals in r satisfies suppk(r̂)≤suppk(r). Hence, once a rule r fails to pass the minimum support test, all rules longer than r that also contain the all the literals in r may be stopped from being considered.

Second, rules whose score is smaller than a user-defined threshold $u_{min}$ can be eliminated. Now, suppose that a new rule r̂ is to be built by taking a rule r and adding a literal 1. In that case, given a category k, the score of this rule is to satisfy:

$$\mu_k(\hat{r}) = \frac{|r|\mu_k(r) + \rho_{l,k}}{|r|+1} \ge \mu_{min} \quad (3)$$

Let $$\overline{\rho}_k = \max_l \rho_{l,k}$$

be the largest score for label category k among all available literals, then an extension of r can be predicted to have a score greater than $\mu_{min}$ if:

$$\mu_k(r) \ge \frac{(|r|+1)\mu_{min} - \overline{\rho}_k}{|r|} = m_k(|r|) \quad (4)$$

Given the maximum number of rules to be mined per label M, $\mu_{min}$ is recomputed as the system iterates through combining literals to build new rules. Indeed, the scores for the temporary list of candidate rules is periodically sorted and set $\mu_{min}$ equal to the score of the M-th rule in the sorted list. As $\mu_{min}$ increases due to better candidate rules becoming available, the condition in Equation (4) becomes more restrictive, resulting in less rules being considered and therefore in a faster overall mining.

Figure 2C:
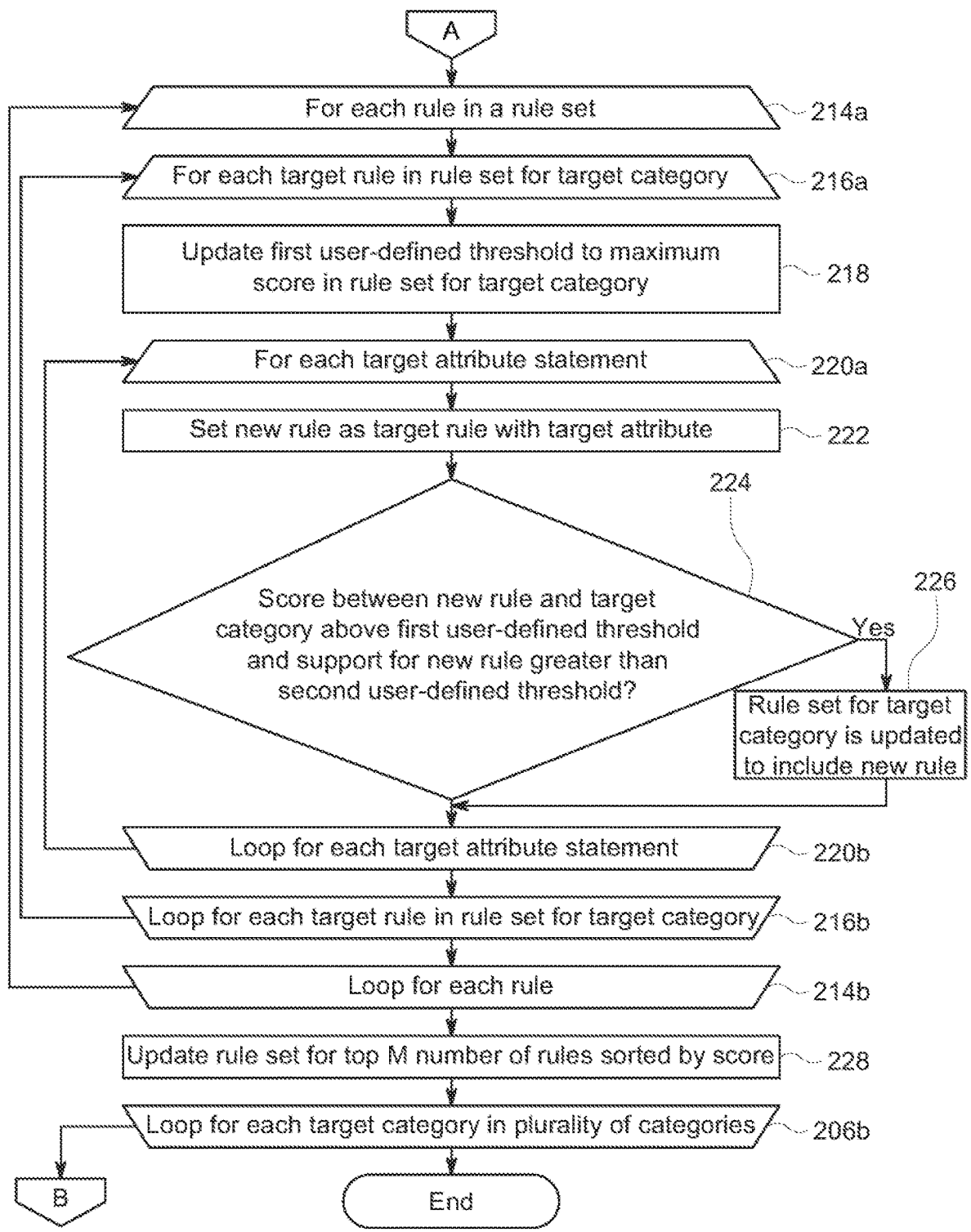
FIG. 2C depicts a flow chart illustrating a portion of the MCA-based rule mining algorithm of FIG. 2A, according to some implementations of the present disclosure.
Figure 3:
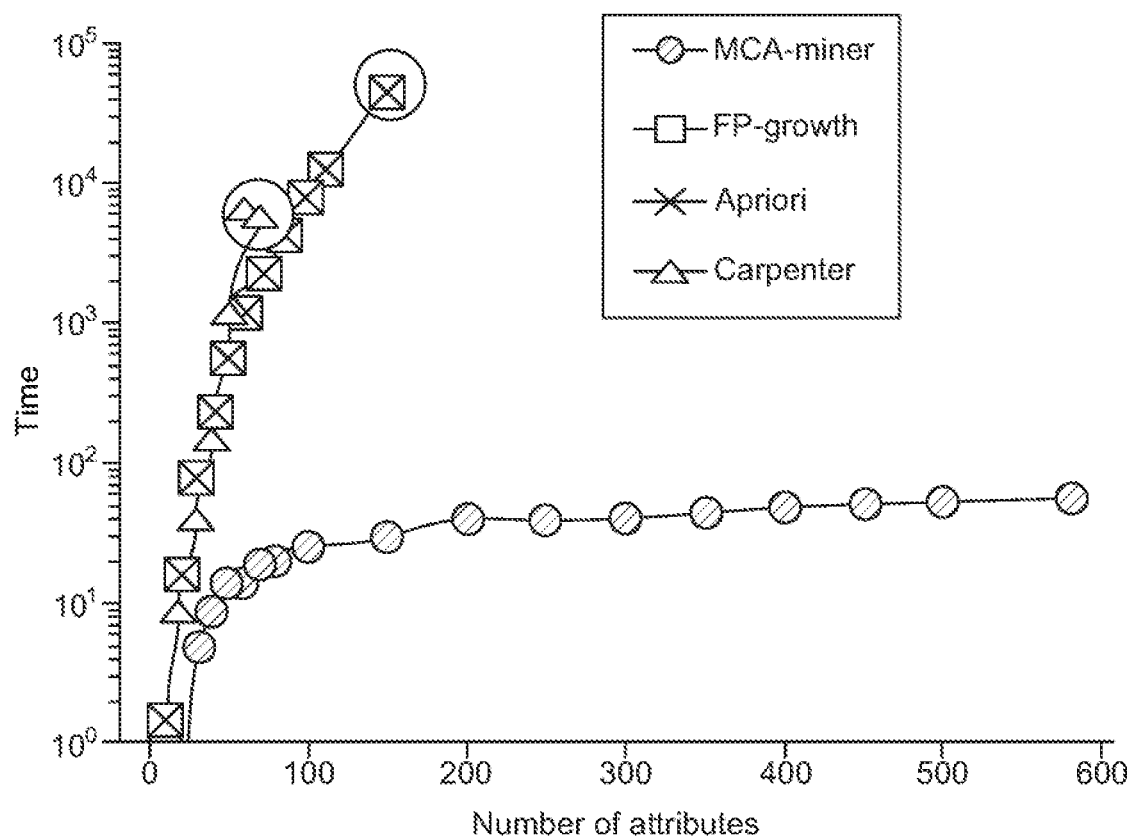
FIG. 3 depicts a graph of a rule mining wall execution time comparison between MCA-miner, FP-Growth, Apriori, and Carpenter, according to some implementations of the present disclosure.

FIGS. 2A-2C depict a pseudocode and flowcharts of a MCA-based rule mining algorithm disclosed herein. The loop iterating over label categories in line three (3) may be easily parallelized as a multi-core computation, significantly reducing the mining time as shown in FIG. 3. The flowchart illustrated in FIGS. 2B and 2C represents the pseudocode presented in FIG. 2A. The process may be performed by a computer that includes a memory that stores computer instructions, and a processor that executes the computer instructions to perform actions. The actions performed by the computer include those computer operations that result in the computer executing the illustrated process.

FIGS. 2B-2C illustrate a process for the MCA based rule mining model as disclosed herein. The process begins, at block 202 in FIG. 2B, where a data set is obtained. The data set includes a plurality of attribute statements for a plurality of label categories. The process proceeds to block 204, where a score for each combination of each attribute statement with each label category is then determined, such as described above with respect to Equation 1. The process continues at loop block 206a where each target category in the plurality of categories of the data set is processed as described below until loop block 206b. The process proceeds next to loop block 208a where each target attribute statement of the plurality of attribute statements of the data set is processed as described below until loop block 208b.

The process continues next at decision block 210, where a determination is made whether two parameters are true: (i) the score for the target category and the target attribute statement is greater than a first user-defined threshold, and (ii) support for the attribute statement is greater than a second user-defined threshold. If both parameters are true, the process proceeds to block 212; otherwise, the process proceeds to loop block 208b. At block 212, the rule set for the target category is updated to include the target attribute statement, after which the process flows to loop block 208b.

At loop block 208b, the process loops to loop block 208a until each attribute statement of the plurality of attribute statements is processed. The process then proceeds to loop block 214a in FIG. 2B. At loop block 214a, each rule of a plurality of rules in a rule set associated with the data set is processed as described below until loop block 214b. The process continues at loop block 216a where each target rule in the rule set for the target category is processed as described below until loop block 216b. The process proceeds to block 218, where the first user-defined threshold is updated to the maximum score in the rule set for the target category.

The process continues at loop block 220a where each target attribute statement of the plurality of attribute statements is processed as described below until loop block 220b. The process proceeds to block 222, where a new rule is set as the target rule with the target attribute. The process continues next at decision block 224, where a determination is made whether two additional parameters are true: (i) a score between the new rule and the target category is above the current first user-defined threshold, and (ii) the support for the new rule is greater than the second user-defined threshold. If both parameters are true, the process proceeds to block 226; otherwise, the process proceeds to loop block 220b. At block 226, the rule set for the target category is updated to include the new rule, after which the process flows to loop block 220b.

At loop block 220b, the process loops to loop block 220a until each attribute statement of the plurality of attribute statements is processed, and the process then proceeds to loop block 216b. At loop block 216b, the process loops to loop block 216a until each target rule in the rule set for the target category is processed, and the process then proceeds to loop block 214b. At loop block 214b, the process loops to loop block 214a until each rule is processed, and the process then proceeds to block 228. At block 228, the rule set is updated for the top M number of rules sorted by score.

The process then continues at loop block 206b, where the process loops to loop block 206a in FIG. 2B until each category of the plurality of categories is processed, and the process then terminates or otherwise returns to a calling process to perform other actions.

Feature Selection

Prior to application of the rule mining techniques disclosed herein, in some examples, various methods are disclosed to identify features from which the rules may be mined. This allows for identification of the most important features, to make the rule mining process more efficient and have less literals or rules that contribute noise to the rule lists.

In some examples, forward selection techniques are implemented for identifying relevant features from the datasets, and for stratifying patients. For instance, logistic regression models with elastic net regularization are utilized in some cases to identify the most important features from the data. Then, either logistic or linear regression models can be utilized to stratify patients from these features, and/or the rule mining techniques can be applied to the features identified (and in combination with linear regression in one example). The data (including the features) are processed by a Bayesian Rule List algorithm, which in turn outputs a Bayesian Decision List that can stratify patients.

According to some implementations of the present disclosure, these decision lists or rule lists may be applied for (i) screening healthy groups from patients, (ii) separating patients into diagnostic categories, (iii) identifying patients that are higher responders to certain drugs, and/or (iv) any combination thereof.

Model Fitting and Feature Importance Weighting

The goals of machine learning analyses may include (i) to establish robust classifiers, (ii) to identify important features that can be used to stratify patients, or (iii) both (i) and (ii). To achieve the first goal of establishing robust classifiers, a logistic regression model can be utilized. Separate logistic regression models may be independently trained using each or various combinations of the above extracted feature modalities as inputs. In some implementations, the performances of each model can be evaluated.

If the number of features is relatively large, an elastic net regularization term can be added in all of the logistic regression models to prevent overfitting. The elastic net regularization is a linear combination of the L1 and L2 regularization terms and has been shown to have advantages over L1 and L2 regularization when dealing with high-dimensional data with small sample size and correlated features. The use of elastic net regularization in these models also enabled feature selection as the regularization induces sparse models via the grouping effect where all the important features will be retained and the unimportant ones set to zero. This allows for the identification of predictive features.

The elastic net regularized logistic regression implemented in the scikit-learn toolbox contains two hyperparameters: the overall regularization strength and the mixing ratio between the L1 and L2 terms. The following procedure can be utilized to determine the best regularization parameters. First, the input data can be randomly partitioned into a development set and an evaluation set. The development set can contain 80% of the data upon which a grid search with 3-fold cross validation procedure can be implemented to determine the best hyperparameters. Then the model can be trained on the entire development set using the best hyperparameters and can be further tested on the remaining 20% of evaluation set which the model had never seen before to obtain testing performance.

All features can be standardized to have zero mean and unit variance within the training data (the training folds in the 3-fold cross validation or the development set) and the mean and variance from the training data can be used to standardize the corresponding test data (the testing fold or the evaluation set) to avoid information spill-over from test data to training data. The entire process can be implemented ten (10) times on ten (10) different random partitions of the development and evaluation sets or other various combinations of times. The following metrics can be used to quantify the model performances: area under the receiver operating characteristics curve (AUC), accuracy, sensitivity, and specificity.

From the above trained models, one can assess how predictive each feature is since the weights of the logistic regression model in the transdiagnostic classifiers represent the relationship between a given feature and the logarithm of the odds ratio of an observation being a patient. For each feature, its corresponding mean model weight can be calculated and divided by the standard deviation across the ten (10) model implementations as the proxy for feature importance. Such a feature importance measure is analogous to the Cohen's d effect size measure and thus favored features with large weights and small standard deviations across the ten (10) model implementations. Features with large importance values from the transdiagnostic classifiers are potentially symptoms, traits, and neuropathological mechanisms shared across patient groups but are distinct from healthy controls or other relevant traits related to responding to certain medications.

Feature Importance-Guided Sequential Model Selection

If the feature dimension of the input data is high compared to the sample size in the dataset, the transdiagnostic classifiers using the full feature sets are likely to be subjected to a substantial amount of noise as well as features that are not predictive. The presence of those noisy features, especially when the sample size is small, might impede the ability of the models to achieve their best performances.

To investigate whether improved classification performances can be achieved from a reduced set of most predictive features, the following feature importance-guided sequential model selection procedure can be utilized. Specifically, first the features in the classifiers may be rank ordered according to their feature importance measures. Next, a series of truncated models may be built such that each model would only take the top k most predictive features as inputs to perform the same transdiagnostic classification problems. Let k range from the top 1 most predictive feature to all available features in steps of 1 for clinical phenotype features, MRI features, task based features, or other combinations of features. For any feature or feature combinations involving fMRI correlations, because of the significantly increased feature dimension, the k's were chosen from a geometric sequence with a common ratio of two (e.g., 1, 2, 4, 8, 16, . . . ).

Model performances can be obtained for each truncated model and can be evaluated as a function of the number of top features (k) included in each truncated model. To statistically test whether a model's performances is significantly above chance level, a random permutation test can be performed where labels in the data can be shuffled 100 times, or any other suitable numbers of times. The model can be trained on these label-shuffled data using exactly the same approach as described herein. The performances from the 100 models can be used to construct the empirical null distribution against which the model performance from the actual data was then compared.

Generating Rule Lists from Identified Features

According to some implementations of the present disclosure, once the top features are identified to separate a set of groups using forward selection, a rule miner and BRL algorithm can be utilized to developed rules to separate those groups. For instance, the output labels for the data used by a rule miner can be derived from the groups separated by, for instance, a linear regression model used in forward selection. The rule miner can then output a set of rules derived from the features. Lastly, a Bayesian Rule List model can be applied to the set of rules to develop decision lists that would separate the patients into the same groups.

Methods of Generating Decision Lists

According to some implementations of the present disclosure, the system, the methods, and the models may be utilized in various combinations to generate rule lists or Bayesian Decision Lists that are capable of stratifying patients. For instance, the Bayesian Decision Lists may be capable of screening patients for mental health disorders, for diagnosing patients, or for matching patients to the right neurobehavioral treatments (e.g. certain drugs or other treatments).

Figure 21:
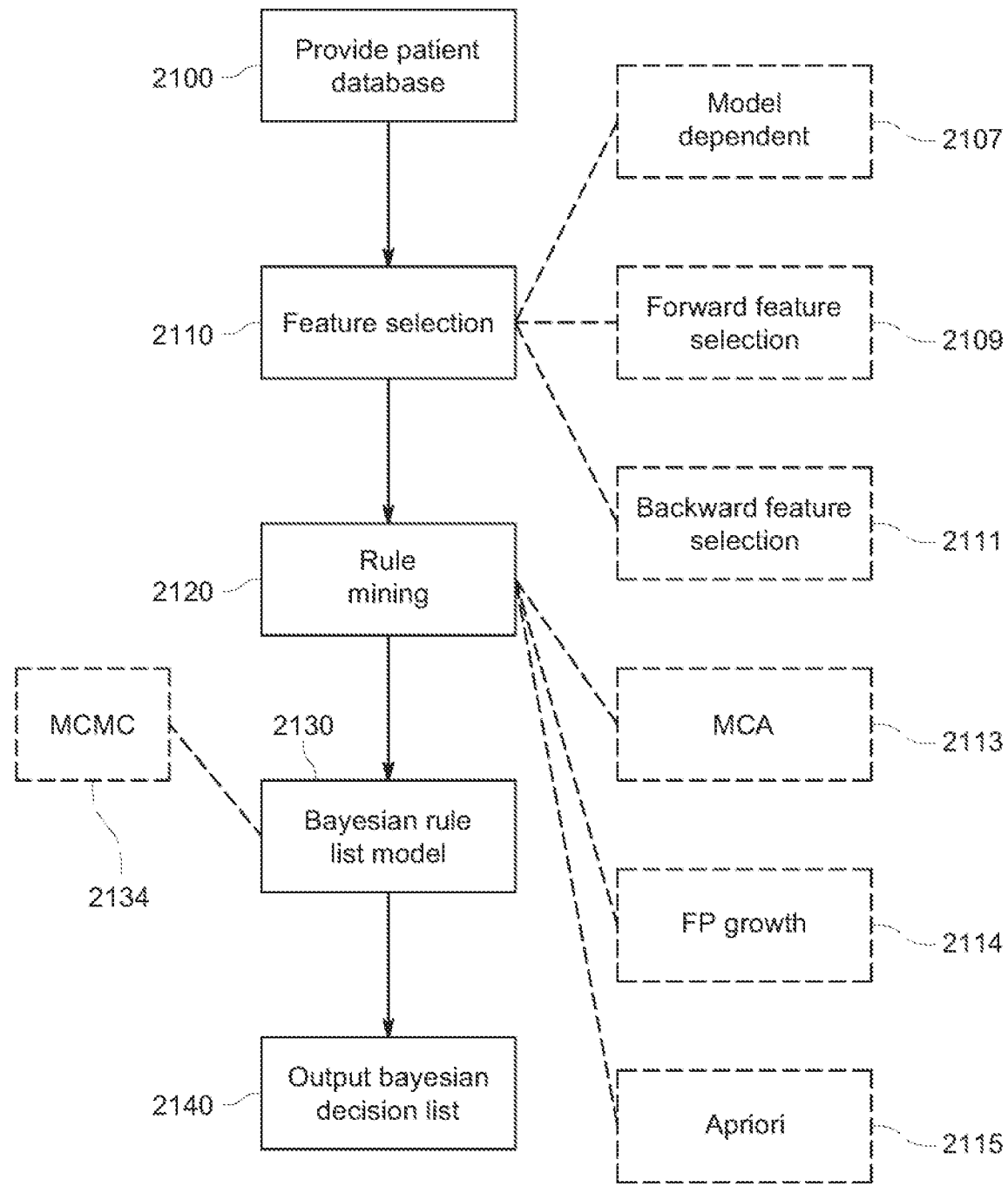
FIG. 21 depicts a flow chart showing a process for classifying patients using the disclosed models, according to some implementations of the present disclosure.

FIG. 21 is a flow chart illustrating a process for generating a Bayesian Decision List as disclosed herein. First, a patient database may be provided 2100 that includes labelled data with different attributes associated with certain outcomes. The patient database may include a variety of different modalities of data including MRI data of a patient's brain, responses to clinical scales questionnaires, data relating to levels of biochemical markers tested from a patient's body ("wet biomarkers"), demographic data (e.g., age, sex, etc.), task data (e.g. output from various tasks disclosed herein), and audio/facial expression data.

Then, in some examples, the data may be first processed with a features selection model 2110 as disclosed herein. In some examples, this may include model dependent feature selection 2107 (e.g. elastic net, LASSO), forward feature selection 2109 as disclosed herein, backward feature selection 2111, or other suitable features selection models. In other examples, the data may not be processed with a features selection model 2109 to first narrow down the features that a rule miner would be applied to.

Next, in some examples, a rule mining model may be applied to the data 2120 or the selected features and associated outcomes from step 2110. Various suitable rule mining models may be utilized including the novel MCA rule mining model 2113 disclosed herein. In other examples, FP growth 2114, Apriori 2115, or other rule mining methods may be utilized. This may output a set of rules for further processing.

Next, a Bayesian Rule List model may be applied 2130 to the set of rules output by the rule miner 2120. In other examples, a Bayesian Rule List model could be applied 2130 to all possible rules or be applied to a set of rules identified using a method other than a rule miner 2120. The Bayesian Rule List model may be applied based on the examples disclosed herein or other suitable application of the model and/or framework generally. In some examples, it may include the MCMC algorithm 2134 described herein.

Next, the process will output a Bayesian Decision List 2140 capable of classifying the data. In the disclosed examples, these will primarily relate to classifying individuals or patients into neurobehavioral categories including screening healthy from patients, diagnosing patients with mental disorders, and identifying a specific treatment for a specific patient. This decision list may be saved in a memory of a computer, displayed on a display or both.

Systems and Data Acquisition

Figure 22:
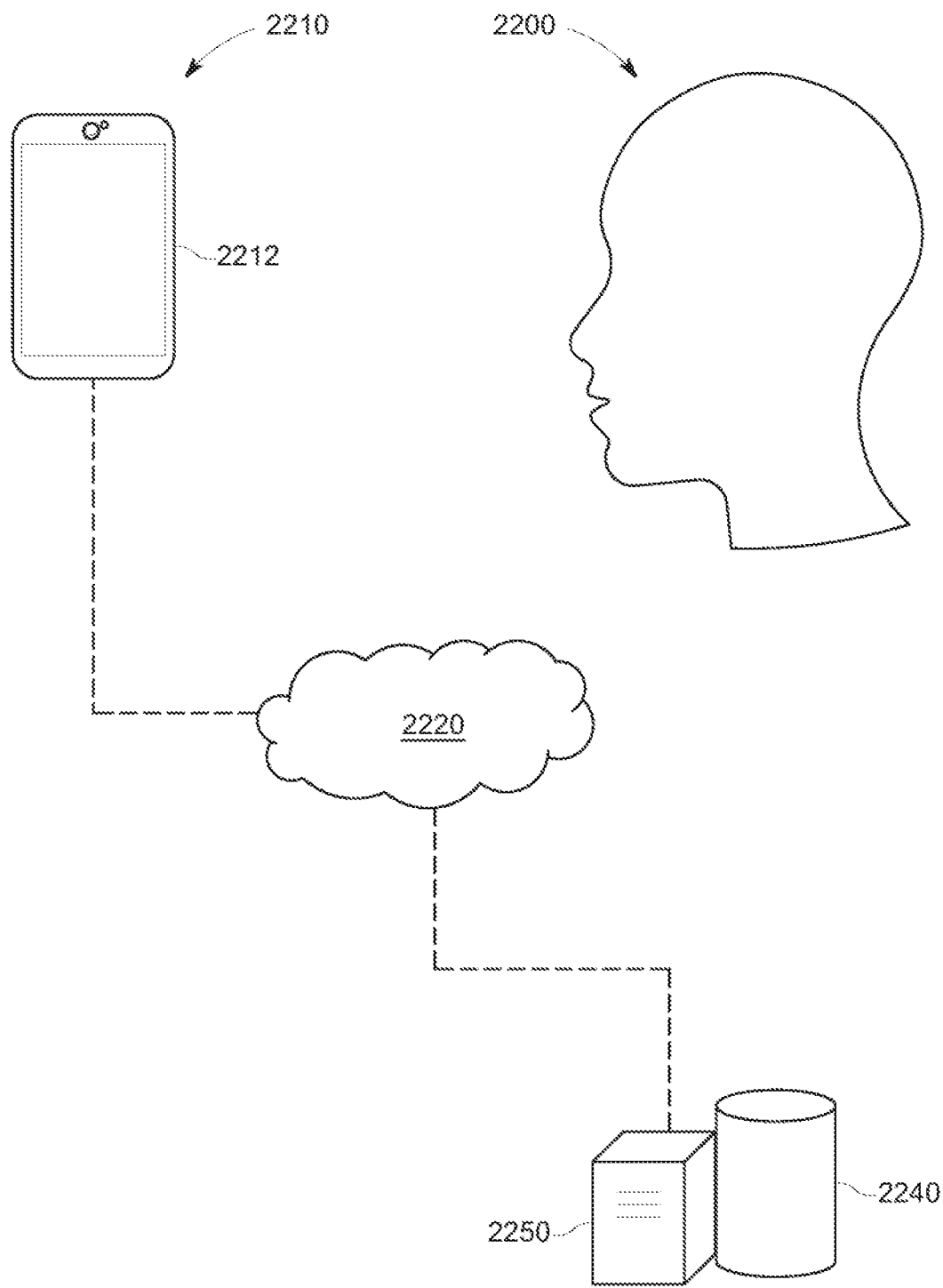
FIG. 22 depicts an overview of a system for classifying patients using the disclosed models, according to some implementations of the present disclosure.

FIG. 22 illustrates various example systems that may be utilized to implement the disclosed technology. For instance, the system may include a computing device 2210 with a display and/or interface 2212, a network 2220, a patient 2200, a server 2250 and database 2240. In some examples, the interface may include a microphone and speaker. In some examples, the speaker may provide instructions, questions or other information to patient, and the microphone may capture the patient's answer, responses, and vocal features. The computing device 2210 may be any suitable computing device, including a computer, laptop, mobile phone, tablet, etc. The network 2220 may be wired, wireless, or various combinations of wired and wireless. The server 2250 and database may be local, remote, and may be combinations of servers 2250 and database 2240, or could be local processors and memory. The computing device 2210 and server 2250 may include a control system with one or more processors. In some examples, all of the processing may performed on a computing device 2210 or portions of the processing may be performed on the computing device 2210 and other portions of the processes may be performed on the server 2250.

The display and/or interface 2212 may be a touchscreen interface and display, or may be a keyboard and display or any other suitable interface to implement the technology disclosed herein, including a microphone and speaker. For instance, certain tasks disclosed herein or utilized in the art may include certain interface features.

Additionally, certain biochemical tests and instruments (not pictured) may be utilized to test certain biochemical markers of the patient 2200. This include various blood tests known in the art for testing for tumor necrosis factor. For instance, ELISA tests may be utilized with various plate readers to quantify the levels of certain molecules or biochemical moieties in a patient 2200.

Furthermore, magnetic resonance or other machines may be utilized scan patients and output MRI data or brain functional data that is utilized by the disclosed models to stratify patients. MRI data may correspond to a set of MRI images of a biological structure. In some examples, the MRI data corresponds to MRI data for a patient's brain. The MRI data can include task-based fMRI data, rs-fMRI data, and/or sMRI data and others.

The MRI data may be acquired using a variety of methods, including for instance, using 3T Siemens Trio scanners. In one example, sMRI data may be T1-weighted and acquired using a magnetization-prepared rapid gradient-echo (MPRAGE) sequence with the following acquisition parameters: TR=1.9 s, TE=2.26 ms, FOV=250 mm, matrix=256×256, 176 1-mm thick slices oriented along the sagittal plane. As an example, the resting-state fMRI scan may be a single run lasting 304 s. However, these are example only, and a variety of other acquisition methods could be utilized.

Methods of Applying Decision Lists to Stratify Patients

Figure 23:
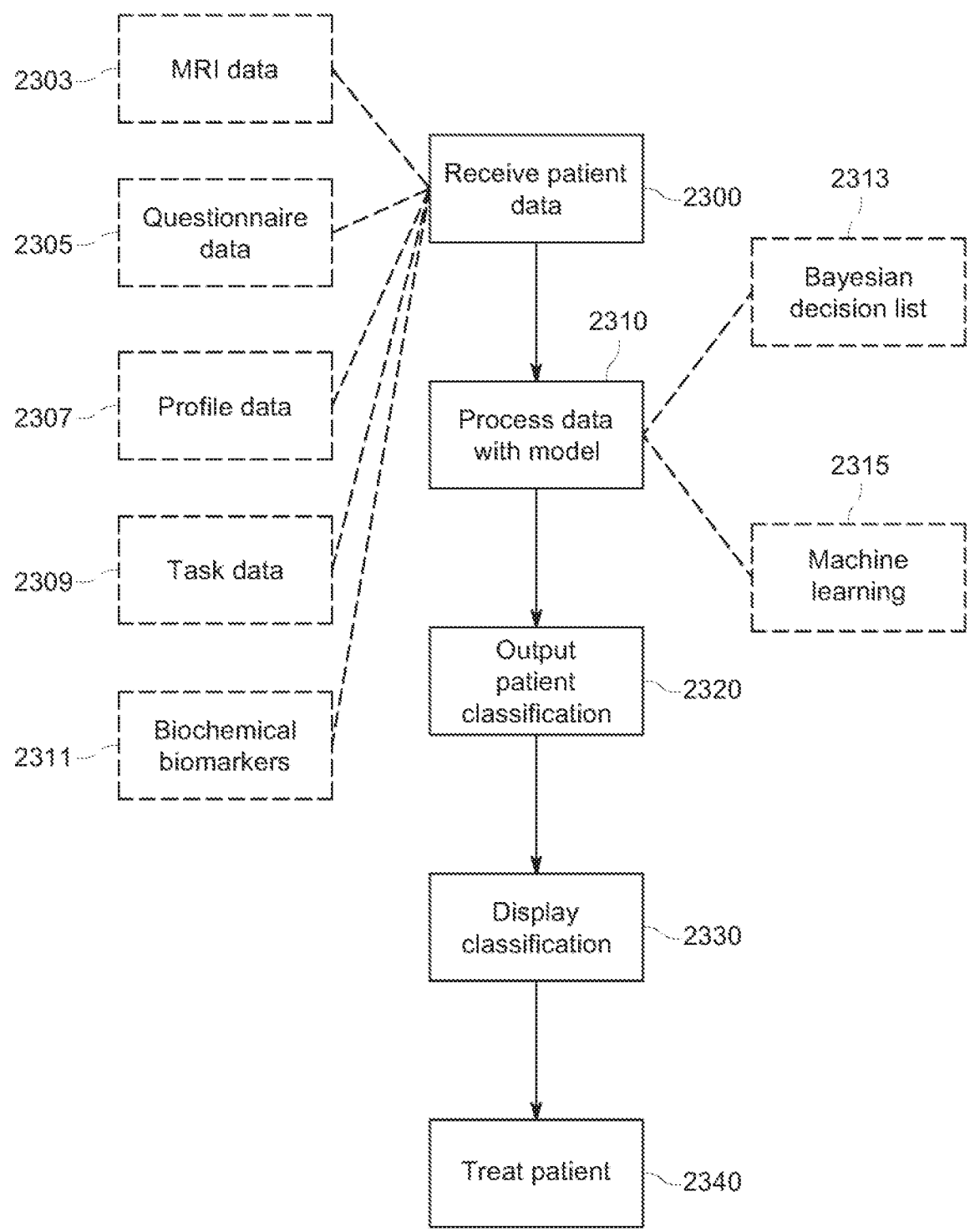
FIG. 23 depicts a flow chart showing a process for classifying patients using the disclosed models, according to some implementations of the present disclosure.
Figure 24:
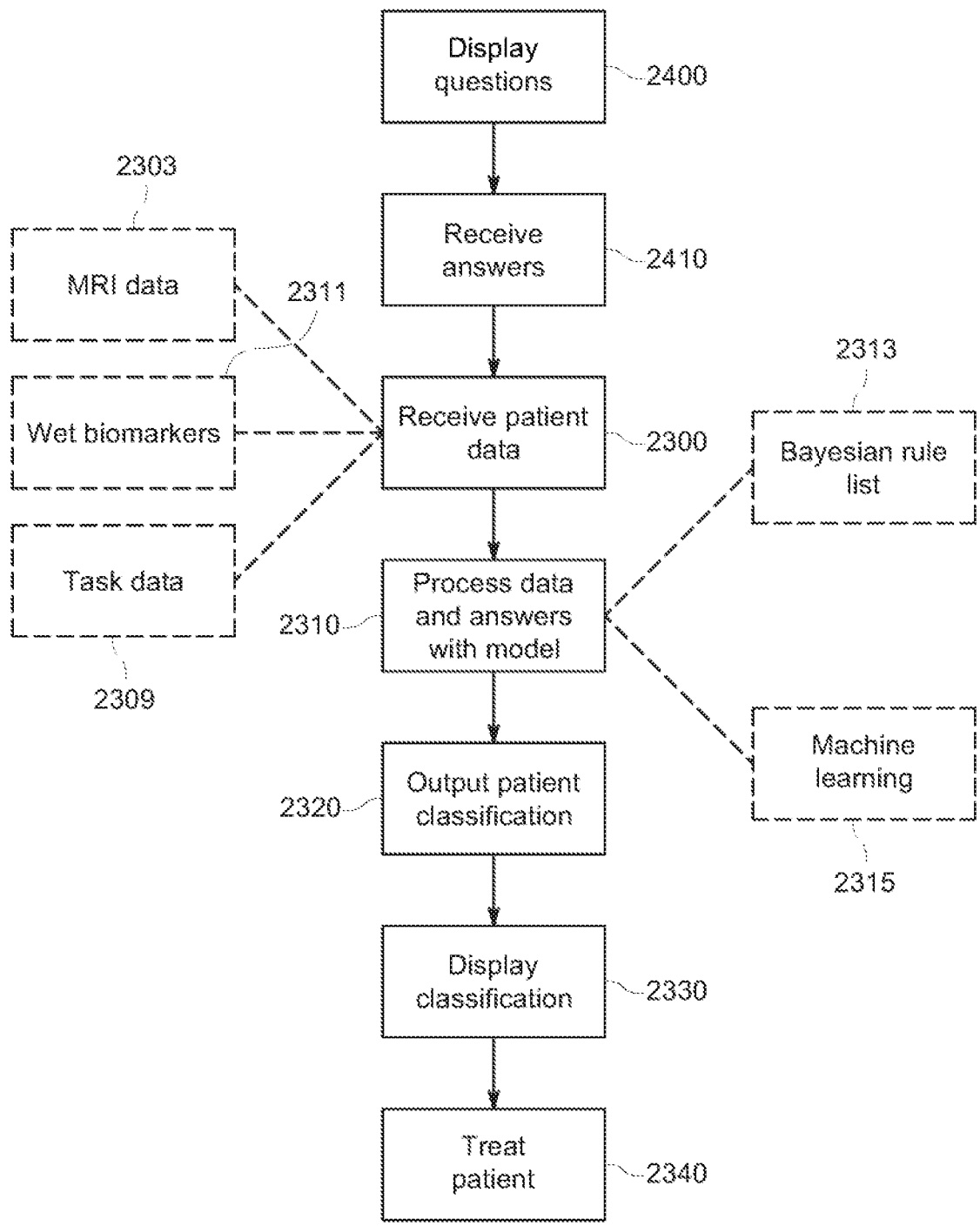
FIG. 24 depicts a flow chart showing a process for classifying patients using the disclosed models, according to some implementations of the present disclosure.

FIGS. 23 and 24 illustrate flow charts showing example methods of stratifying individual patients using the disclosed Bayesian Decision Lists. For instance, FIG. 23 illustrates a method of stratifying a patient using received patient data 2300. For instance, the patient data may include MRI data 2303, questionnaire data 2305 (e.g. clinical scales), profile and/or demographic data 2307 that may include for instance age, sex, weight, ethnicity or others, task data 2309 that may include a variety of tasks such as the those disclosed herein, or biochemical biomarker levels in a patient 2311 such as tumor necrosis factor or others.

Next, the patient data may be processed with a model 2310. In many examples, a Bayesian Decision List 2313 may be utilized to process the data. This provides an interpretable result that a clinician may validate. In other examples, other machine learning models 2315, decision lists or similar models may be utilized to stratify patients in the neurobehavioral space. In some examples, the disclosed rule miner may be utilized to stratify patients outside the neural behavioral space, especially given its potential for multi-model (or data type) utilization.

Next, the system may output a patient classification 2320 which may then be displayed 2330 in a display, interface, and/or stored in a memory reference to the patient (or an identifier for the patient). Accordingly, the rule list utilized may also be displayed including how the patient was classified according to the rule list—including which rules the patient fell under to reach the classification. This would provide an interpretable classification of the patient.

The classification may be used: (i) as a screening tool to determine whether the patient is healthy or has a mental disorder, (ii) to diagnose a mental health disorder, (iii) to determine a probability a patient has a certain mental health disorder, and/or (iv) to recommend a treatment. The treatment may include pharmaceutical drugs, cognitive behavioral therapy including software based versions of the therapy or other suitable therapies.

In some examples, a clinician may also treat the patient 2340. This may include prescribing a pharmaceutical that may be administered to the patient or the patient may be instructed to take. In other examples, this could be a recommended software program, including software based versions of cognitive behavioral therapy.

FIG. 24 illustrates a similar process but additional includes further details on acquiring scales related data from the patient using a computing device 2210 such as a tablet or mobile phone. For instance, the scales or questionnaire data 2305 may be acquired by displaying a series of text based questions on a display 2400 and receiving a patient selection of answers 2410 through an interface 2212 which may include multiple choice answers or other inputs. In other examples, the patient may fill out a paper based questionnaire and the data may be entered into the disclosed systems and methods.

EXAMPLES

The following examples are provided to better illustrate the claimed disclosure and are not intended to be interpreted as limiting the scope of the disclosure. To the extent that specific materials or steps are mentioned, it is merely for purposes of illustration and is not intended to limit the disclosure. One skilled in the art may develop equivalent means or reactants without the exercise of inventive capacity and without departing from the scope of the disclosure.

Example 1

Benchmark Datasets

The MCA-miner method disclosed herein in FIGS. 2A-2C, when used together with BRL, offers the power of rule list interpretability while maintaining the predictive capabilities of already established machine learning methods.

The performance and computational efficiency of the new MCA-miner is benchmarked against the "Titanic" dataset, as well as the following five (5) datasets available in the UCI Machine Learning Repository: "Adult," "Autism Screening Adult," "Breast Cancer Wisconsin (Diagnostic)," "Heart Disease," and "HIV-1 protease cleavage," which are designated as Adult, ASD, Cancer, Heart, and HIV, respectively. These datasets represent a wide variety of real-world experiments and observations, thus enabling the improvements described herein to be compared against the original BRL implementation using the FP-Growth miner.

All six benchmark datasets correspond to binary classification tasks. The experiments were conducted using the same set up in each of the benchmarks. First, the dataset is transformed into a format that is compatible with the disclosed BRL implementation. Second, all continuous attributes are quantized into either two (2) or three (3) categories, while keeping the original categories of all other variables. It is worth noting that depending on the dataset and how its data was originally collected, the existing taxonomy and expert domain knowledge are prioritized in some instances to generate the continuous variable quantization. A balanced quantization is generated when no other information was available. Third, a model is trained and tested using 5-fold cross-validations, reporting the average accuracy and Area Under the ROC Curve (AUC) as model performance measurements.

Table 1 presents the empirical result of comparing both implementations. The notation in the table follows the definitions above. To strive for a fair comparison between both implementations, the parameters rmax=2 and smin=0:3 are fixed for both methods, and in particular for MCA-miner $\mu_{min}$=0:5 and M=70 are also set. The multi-core implementations for both the new MCA-miner and BRL were executed on six parallel processes, and stopped when the Gelman & Rubin parameter satisfied $\hat{R} \leq 1.05$. All the experiments were run using a single AWS EC2 c5.18xlarge instance with 72 cores.

TABLE 1

Performance evaluation of FP-Growth against MCA-miner when used with
BRL on benchmark datasets. $t_{train}$ is the full training wall time.

| DATASET | n | p | $\Sigma_{i=1}^{P}|a_i|$ | FP-GROWTH + BRL | | | MCA-MINER + BRL | | |
|---|---|---|---|---|---|---|---|---|---|
| | | | | ACCURACY | AUC | $t_{train}$ [s] | ACCURACY | AUC | $t_{train}$ [s] |
| Adult | 45,222 | 14 | 111 | 0.81 | 0.85 | 512 | 0.81 | 0.85 | 115 |
| ASD | 248 | 21 | 89 | 0.87 | 0.90 | 198 | 0.87 | 0.90 | 16 |
| Cancer | 569 | 32 | 150 | 0.92 | 0.97 | 168 | 0.92 | 0.94 | 22 |
| Heart | 303 | 13 | 49 | 0.82 | 0.86 | 117 | 0.82 | 0.86 | 15 |
| HIV | 5,840 | 8 | 160 | 0.87 | 0.88 | 449 | 0.87 | 0.88 | 36 |
| Titanic | 2,201 | 3 | 8 | 0.79 | 0.76 | 118 | 0.79 | 0.75 | 10 |

It is clear from the experiments in Table 1 that the new MCA-miner matches the performance of FP-Growth in each case, while significantly reducing the computation time required to mine rules and train a BRL model.

Example 2

Transdiagnostic Screener for Mental Health

The disclosed systems and methods for stratifying patients was applied to a data set from the Consortium for Neuropsychiatric Phenomics ("CNP"). CNP is a research project aimed at understanding shared and distinct neurobiological characteristics among multiple diagnostically distinct patient populations. Four groups of subjects are included in the study: healthy controls (HC, n=130), Schizophrenia patients (SCHZ, n=50), Bipolar Disorder patients (BD, n=49), and Attention Deficit and Hyperactivity Disorder patients (ADHD, n=43). The total number of subjects in the dataset is n=272. The goal in analyzing the CNP dataset was to develop interpretable and effective screening tools to identify the diagnosis of these three psychiatric disorders in patients.

CNP Self-Reported Instruments Dataset

Among other data modalities, the CNP study includes responses to p=578 individual questions, belonging to 13 self-report clinical questionnaires, per subject. The total number of categories generated by the 578 questions is $\Sigma_{i=1}^{P}|a_i|=1350$. The 13 questionnaires are the following (in alphabetical order):

Adult ADHD Self-Report Screener (ASRS),
Barratt Impulsiveness Scale (Barratt),
Chapman Perceptual Aberration Scale (ChapPer),
Chapman Physical Anhedonia Scale (ChapPhy),
Chapman Social Anhedonia Scale (ChapSoc),
Dickman Function and Dysfunctional Impulsivity Inventory (Dickman),
Eysenck's Impulsivity Inventory (Eysenck),
Golden & Meehl's 7 MMPI Items Selected by Taxonomic Method (Golden),
Hopkins Symptom Check List (Hopkins),
Hypomanic Personality Scale (Hypomanic),
Multidimensional Personality Questionnaire—Control Subscale (MPQ),
Temperament and Character Inventory (TCI), and
Scale for Traits that Increase Risk for Bipolar II Disorder (BipolarII).

The individual questions are abbreviated using the name in parenthesis in the list above together with the question number. For example, Hopkins #57 denotes the 57-th question in the "Hopkins Symptom Check List" questionnaire.

Depending on the particular clinical questionnaire, each question has results in a binary answer (e.g., True or False) or a rating integer (e.g., from 1 to 5). Each question is used as a literal attribute, resulting in a range from two (2) to five (5) categories per attribute.

TABLE 1

Performance evaluation of FP-Growth against MCA-miner when used with
BRL on benchmark datasets. $t_{train}$ is the full training wall time.

| Dataset | n | P | $\Sigma_{i=1}^{P}|a_i|$ | FP-Growth + BRL | | | MCA-miner + BRL | | |
|---|---|---|---|---|---|---|---|---|---|
| | | | | Accuracy | AUC | $t_{train}$ [s] | Accuracy | AUC | $t_{train}$ [s] |
| Adult | 45,222 | 14 | 111 | 0.81 | 0.85 | 512 | 0.81 | 0.85 | 115 |
| ASD | 248 | 21 | 89 | 0.87 | 0.90 | 198 | 0.87 | 0.90 | 16 |
| Cancer | 569 | 32 | 150 | 0.92 | 0.97 | 168 | 0.92 | 0.94 | 22 |
| Heart | 303 | 13 | 49 | 0.82 | 0.86 | 117 | 0.82 | 0.86 | 15 |
| HIV | 5,840 | 8 | 160 | 0.87 | 0.88 | 449 | 0.87 | 0.88 | 36 |
| Titanic | 2,201 | 3 | 8 | 0.79 | 0.76 | 118 | 0.79 | 0.75 | 10 |

Performance Benchmark

Rather than prune the number of attributes a priori to reduce the search space for both the rule miner and BRL, the new MCA-miner described herein was employed to identify the best rules over complete search space of literal combinations. Note that this results in a challenging problem for most machine learning algorithms since this is a wide dataset with more features than samples, e.g., $\Sigma_{i=1}^{P}|a_i|>>p>>n$. Indeed, just generating all rules with three (3) literals from this dataset results in approximately 23 million rules. FIG. 3 is a graph that compares the wall execution time of the new MCA-miner against three popular associative mining methods: FP-Growth, Apriori, and Carpenter, all using the implementation in the PyFIM package. All samples in the plot were obtained training the same features from the CNP dataset on each method. Times in the plot are an average of five (5) runs. Black circles denote the last successful execution of a method. Executions were automatically canceled for wall times longer than 12 hours.

As shown in FIG. 3, while the associative mining methods are reasonably efficient on datasets with few features, they are incapable of handling more than roughly 70 features from the CNP dataset, resulting in out of memory errors or impractically long executions even for large-scale compute-optimized AWS EC2 instances. In comparison, MCA-miner empirically exhibits a grow rate compatible with datasets much larger than CNP, as it runs many orders of magnitude faster than associative mining methods. It is worth noting that while FP-Growth is shown as the fastest associative mining method, its scaling behavior vs. the number of attributes is practically the same as Apriori in some experiments.

For instance, the magnitude of the feature space grows exponentially. Expressed mathematically, given d unique features, the total number of possible rules is approximately the following:

$$R = \sum_{k=1}^{d-1}\left[\binom{d}{k} \times \sum_{j=1}^{d-k}\binom{d-k}{j}\right] = 3^d - 2^{d+1} + 1$$

The MCA process filters through this space and generates a much smaller rule space. The BRL process constructs the rule list to fit the mode. As disclosed herein, the CNP dataset includes about 578 features, which generate approximately 23 million effective rules. The disclosed MCA algorithm can process through this large set of rules, while the traditional algorithms (e.g., Apriori, FP-Growth) can only handle those with about 100 features.

In addition to the increased performance due to the new MCA-miner, the implementation of the BRL training MCMC algorithm is improved by running parallel Markov chains simultaneously in different CPU cores, as explained herein. FIG. 4 shows the BRL training time comparison, given the same rule set and both using six chains, between the new multi-core implementation against the original single-core implementation reported in. Times in the plot of FIG. 4 are an average of five (5) runs.

Figure 5:
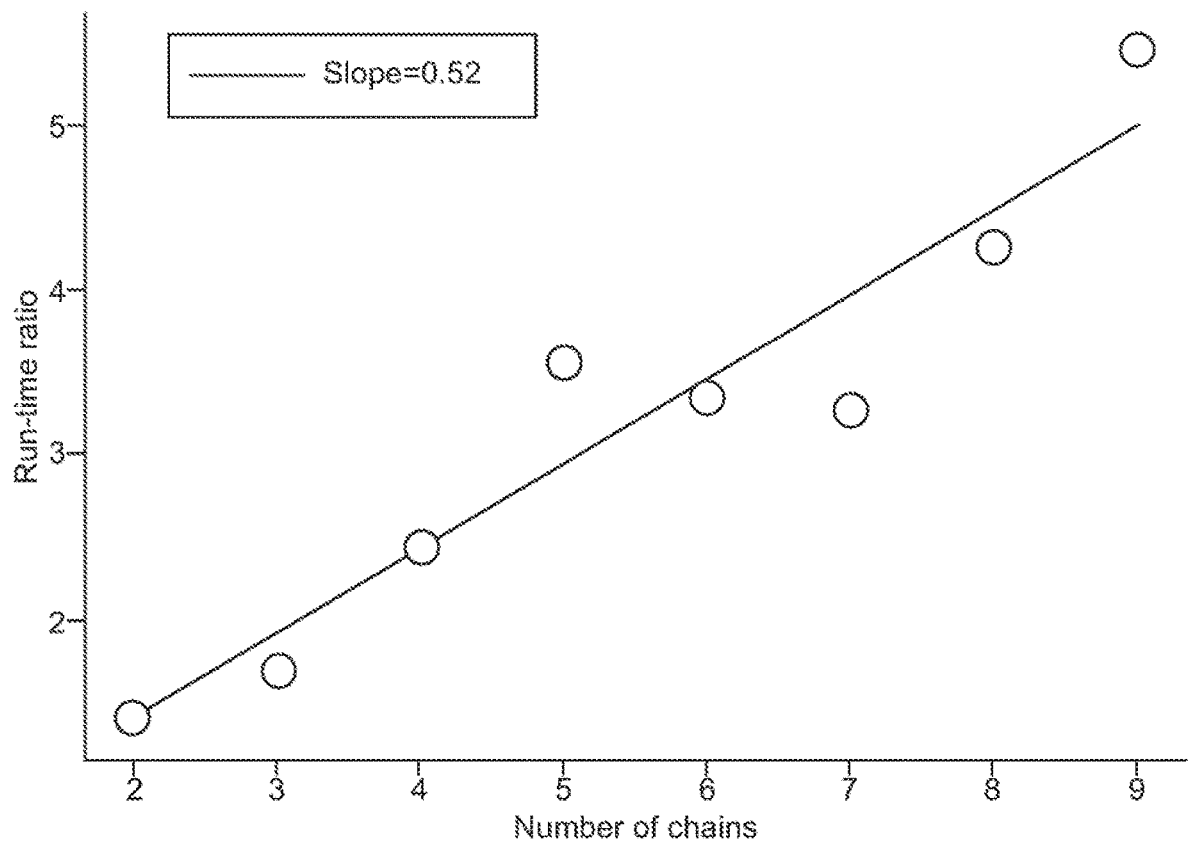
FIG. 5 depicts a graph of a ratio $t_{single-core}/t_{multi-core}$ of MCMC convergence wall execution time as a function of the number of MCMC chains, according to some implementations of the present disclosure.

Also, FIG. 5 shows that the multi-core implementation convergence wall time tmulti-core scales linearly with the number of Markov chains, with tsingle-core≈½ Nchains tmulti-core. The number of cores used in the multi-core implementation is equal to the number of MCMC chains. Times in the plot are an average of five (5) runs. While both implementations display a similar grow rate as the rule set size increases, the new multi-core implementation is roughly three (3) times faster in this experiment.

Interpretable Transdiagnostic Classifiers

In the interest of building the best possible transdiagnostic screening tool for the three types of psychiatric patients present in the CNP dataset, three different classifiers were built. First, a binary classifier is built to separate HC from the set of Patients, defined as the union of SCHZ, BD, and ADHD subjects. Second, a multi-class classifier is built to directly separate all four original categorical labels available in the dataset. Finally, the performance of the multi-class classifier is evaluated by repeating the binary classification task and comparing the results. In addition to using Accuracy and AUC as performance metrics, Cohen's κ coefficient (Cohen 1960) is reported as another indication for the effect size of the new classifier. Cohen's κ is compatible with both binary and multi-class classifiers. It ranges between −1 (complete misclassification) to 1 (perfect classification), with 0 corresponding to a chance classifier. To avoid a biased precision calculation, the dataset is sub-sampled to balance out each label, resulting in n=43 subjects for each of the four classes, with a total of n=172 samples. Finally, 5-fold cross-validation is used to ensure the robustness of the training and testing methodology.

Binary Classifier

Besides the new MCA-miner described herein together with BRL to build an interpretable rule list, its performance is benchmarked against other commonly used machine learning algorithms compatible with categorical data, which were applied using the Scikit-learn (Pedregosa et al. 2011) implementations and default parameters. As shown in Table 2, the method described herein is statistically as good, if not better, than the other methods compared against.

TABLE 2

HC vs. Patient binary prediction performance comparison for different machine learning models.

| CLASSIFIER | ACCURACY | AUC | COHEN |
|---|---|---|---|
| MCA-miner + BRL | 0.79 | 0.82 | 0.58 |
| Random Forest | 0.75 | 0.85 | 0.51 |
| Boosted Trees | 0.79 | 0.87 | 0.59 |
| Decision Tree | 0.71 | 0.71 | 0.43 |

Figure 7:
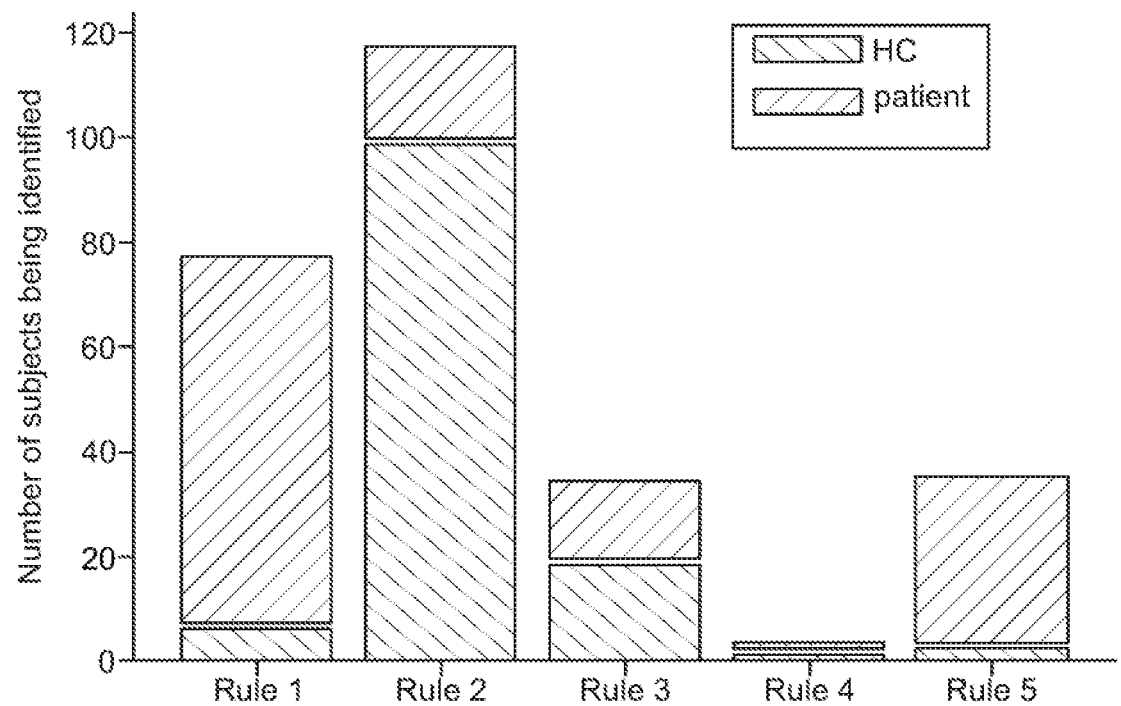
FIG. 7 depicts a bar graph of a breakdown analysis of subject classification per rule in the rule list depicted in FIG. 6, according to some implementations of the present disclosure.

The rule list generated using MCA-miner and BRL is shown in FIG. 6, which depicts a rule list for a transdiagnostic screening of psychiatric disorders, classifying between Healthy Controls vs. Patients Also, a breakdown analysis of the number of subjects being classified per rule in the list is shown in FIG. 7. The detailed description of the questions in FIG. 6 is shown in Table 3. Note that most of the subjects are classified with a high probability in the top two rules, which is a very useful feature in situations where fast clinical screening is required.

Multi-Class Classifier

FIG. 8 shows the output rule list after training a BRL model using the all four labels in the CNP dataset, as explained above. Each rule can be used to infer the diagnosis of a subject. The rule list accuracy is 0.54 and Cohen's Kappa is 0.40. Note that the rules in FIG. 8 emit the maximum likelihood estimate corresponding to the multinomial distribution generated by the same rule in the BRL model, since this is the most useful output for practical clinical use. After 5-fold cross-validation the new MCA-miner with BRL classifier has an accuracy of 0:57 and Cohen's κ of 0:38.

Figure 10:
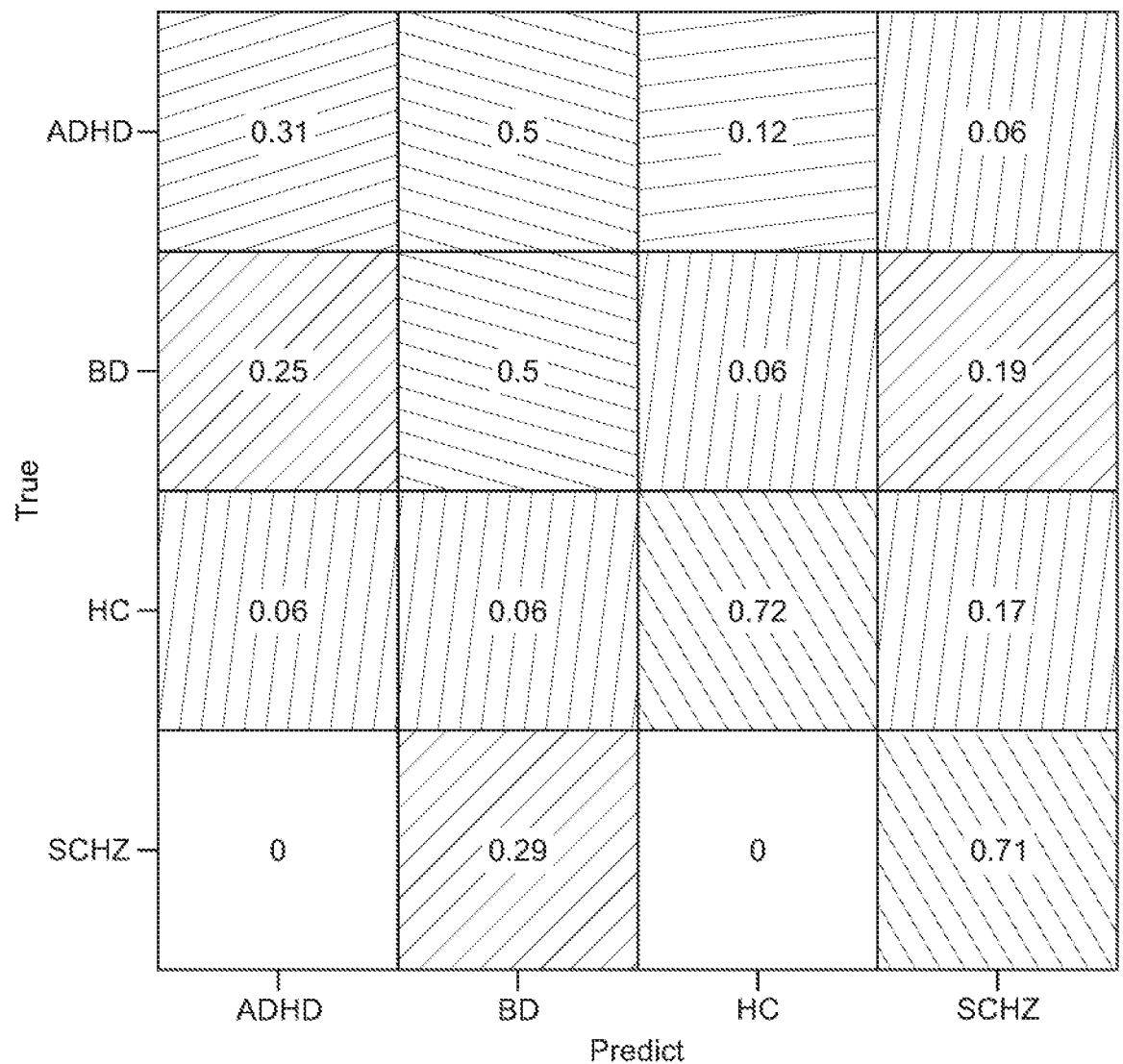
FIG. 10 depicts an average confusion matrix for a multiclass classifier evaluated on 5-fold cross-validation test cohorts, according to some implementations of the present disclosure.

FIG. 10 shows the average confusion matrix for the multi-class classifier using all five (5) cross-validation testing cohorts. The actual questions referenced in the rule list in FIG. 8 are shown in detail in Table 3.

TABLE 3

Questions from the CNP dataset singled out by rule list classifiers in FIGS. 6 and 8

| LABEL | QUESTION | ANSWER TYPE |
|---|---|---|
| Barratt#12 | I am a careful thinker | 1 (rarely) to 4 (almost always) |
| BipolarII#1 | My mood often changes, from happiness to sadness, without my knowing why | Boolean |

TABLE 3-continued

Questions from the CNP dataset singled out
by rule list classifiers in FIGS. 6 and 8

| LABEL | QUESTION | ANSWER TYPE |
|---|---|---|
| BipolarII#2 | I have frequent ups and downs in mood, with and without apparent cause | Boolean |
| ChapSoc#9 | I sometimes become deeply attached to people I spend a lot of time with | Boolean |
| ChapSoc#13 | My emotional responses seem very different from those of other people | Boolean |
| Dickman#22 | I don't like to do things quickly, even when I am doing something that is not very difficult. | Boolean |
| Dickman#28 | I often get into trouble because I don't think before I act | Boolean |
| Dickman#29 | I have more curiosity than most people | Boolean |
| Golden#1 | I have not lived the right kind of life | Boolean |
| Eyenseck#1 | Weakness in parts of your body | Boolean |
| Hopkins#39 | Heart pounding or racing | 0 (not at all) to 3 (extremely) |
| Hopkins#56 | Weakness in parts of your body | 0 (not at all) to 3 (extremely) |
| Hypomanic#1 | I consider myself to be an average kind of person | Boolean |
| Hypomanic#8 | There are often times when I am so restless that it is impossible for me to sit still | Boolean |
| TCI#231 | I usually stay away from social situations where I would have to meet strangers, even if I am assured that they will be friendly | Boolean |

Figure 9:
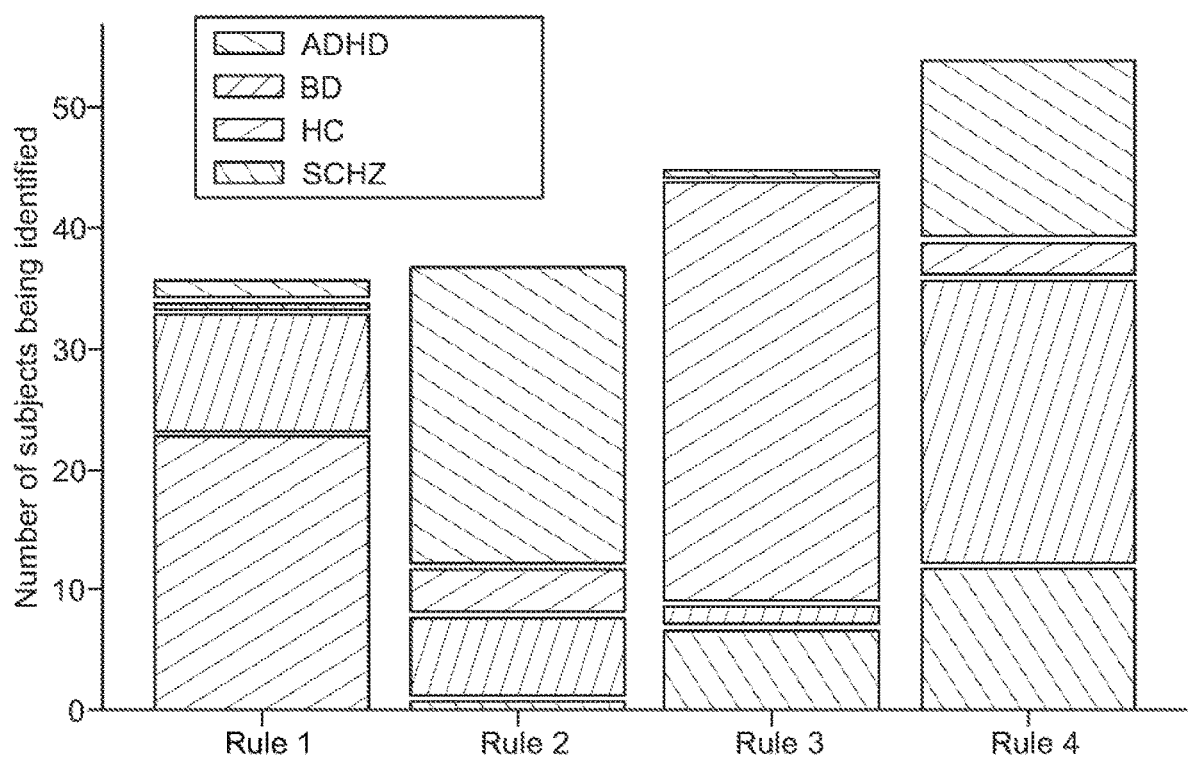
FIG. 9 depicts a bar graph of a breakdown analysis of subject classification per rule in the concise list shown in FIG. 8, according to some implementations of the present disclosure.

The interpretability and transparency of the rule list in FIG. 8 enables us to obtain further insights regarding the population in the CNP dataset. Indeed, similar to the binary classifier, FIG. 9 shows the mapping of all CNP subjects using the 4-class rule list. While the accuracy of the rule list as a multi-class classifier is not perfect, it is worth noting how just 7 questions out of a total of 578 are enough to produce a relatively balanced output among the rules, while significantly separating the label categories.

Also note that even though each of the 13 questionnaires in the dataset have been thoroughly tested in the literature as clinical instruments to detect and evaluate different traits and behaviors, the 7 questions picked by the rule list do not favor any of the questionnaires in particular. This is an indication that transdiagnostic classifiers are better obtained from different sources of data, and likely improve their performance as other modalities, such as mobile digital inputs, are included in the dataset.

Binary Classification Using Multi-Class Rule List

The performance of the multi-class classifier is further evaluated in FIG. 8 by using it as binary classifier, e.g., the ADHD, BD, and SCHZ labels are replaced with Patients. Using the same 5-fold cross-validated models obtained in the multiclass section above, their performance is computed as binary classifiers obtaining an accuracy of 0:77, AUC of 0:8, and Cohen's κ of 0:54. These values are on par with those in Table 2, showing that the method does not decrease performance by adding more categorical labels.

Example 3

Treatment Response to BTRX-246040

The disclosed systems and methods were used in a randomized, placebo controlled study to identify patients that would respond to BTRX-246040 (LY2940094)—a nociceptin receptor antagonist ("NOPA"). Details about the chemical structure and other properties, uses and indications for BTRX-246040 are disclosed in J M Witkin et al., "Therapeutic Approaches for NOP Receptor Antagonists in Neurobehavioral Disorders: Clinical Studies in Majority Depressive Disorder and Alcohol Use Disorder with BTRX-246040," the content of which is incorporated herein by reference in its entirety. Additionally, BTRX-246040, it's uses, indications, treatments, and forms are disclosed in U.S. Pat. No. 8,232,289 filed Nov. 10, 2010, titled "Spiropiperidine Compounds as ORL-1 Receptor Antagonists" and U.S. Publication NO. 2012/0214784 filed Aug. 23, 2012 titled "Spiropiperidine Compounds as ORL-1 Receptor Antagonists," both of which are incorporated by reference in their entirety herein.

During the study disclosed herein, BTRX-246040 was administered once daily in patients with major depressive disorder without anhedonia. The study included 73 patients with 38 randomized to BTRX-246040 and 35 randomized to the placebo. The BTRX group had 17 responders and the placebo had 15 responders. The study included the following methods:

28 days screening period
Eight (8(weeks of active treatment
Off-drug follow up after one to two weeks
104 MDD patients randomized
1:1 ratio stratified by SHAPS ≤4 and SHAPS >4
dosage: 40 mg first week, then 80 mg onwards when tolerated Additionally, the study included the following schedule of assessments listed in Table 4:

TABLE 4

Schedule of Assessments

| | SCREENING | BASELINE | STUDY DRUG TREATMENT | | | | END OF TREATMENT | FOLLOW-UP |
|---|---|---|---|---|---|---|---|---|
| Visit | 1 | 2 | 3 | 4 | 5 | 6 | 7 | 8 |
| Day | D − 28 to D − 7 | D 1 | D 8 | D 15 | D 29 | D 43 | D 57 | |
| Week | | W 0 | W 1 | W 2 | W 4 | W 6 | W 8 | W 9 to W 10 |
| MADRS/CGI | X | X | X | X | X | X | X | X |
| HAMA/HADS/DARS | X | X | | | X | | X | |
| SHAPS | | X | X | X | X | | X | |
| Pain Question | | X | | X | X | X | X | |
| Traumatic Events | X | | | | | | | |
| PRT/EEfRT | | X | | | X | | X | |
| FERT | | X | X | X | | | | |
| Age/Sex/Ethnicity | X | X | | | | | | |

Accordingly, the patients received various assessments during various visits in the 8 weeks of the study. Those includes:

Clinical Scales

The following are known clinical questionnaires that were utilized at the indicated time points above:
- Montgomery-Asberg Depression Scale (MADRS)
- Hamilton Anxiety Scale (HAMA)
- Hospital Anxiety and Depression Scale (HADS-A/HADS-D)
- Snaith-Hamilton Pleasure Scale (SHAPS)
- Dimensional Anhedonia Rating Scale (DARS)

Tasks

The following tasks were administered to the patients, including with mobile or tablet based versions of the tasks that gave the patient instructions and requested input from the patients though a user interface.

Probabilistic Reward Task (PRT)

Figure 11:
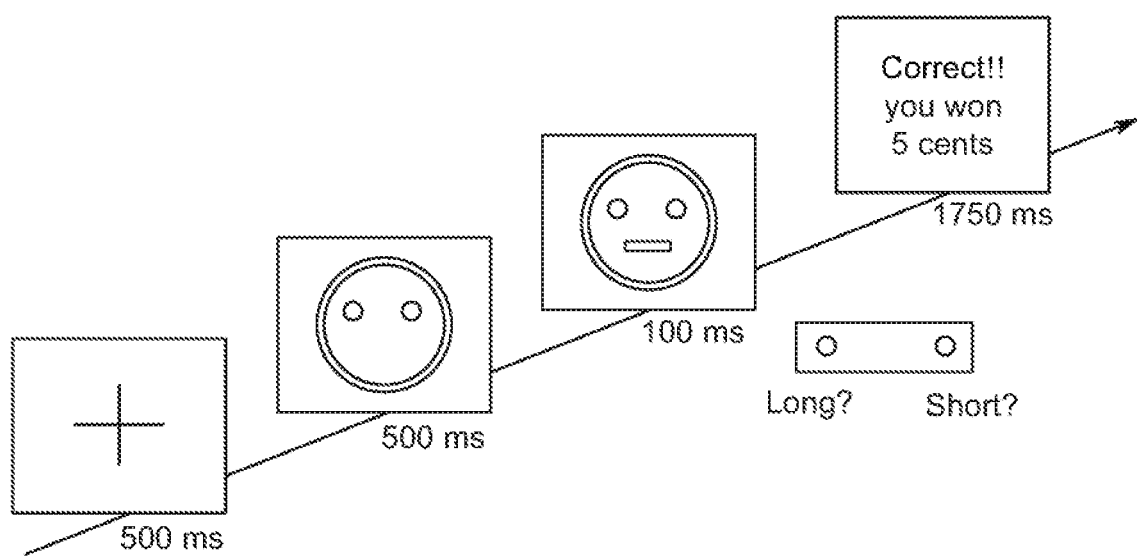
FIG. 11 depicts a schematic illustration of a task design, according to some implementations of the present disclosure.

The PRT task assesses objective measures of reward responsiveness. FIG. 11 is a schematic illustration of the task design for this study. For each trial, subjects' task was to decide whether a short (11.5 mm) or a long (13 mm) mouth was displayed on a previously mouthless cartoon face on a display by a control system by pressing either the 'z' or the '/' key of a keyboard connected to a computer processor and the display of the user interface. In other examples, the keys could have been displayed on a touch screen interface of a tablet or a mobile device. When the subject pressed the correct response, they would sometimes be rewarded with a message like ("Correct!! You won 5 Cents"). The subjects were told the goal is to win as much money as possible and that not all correct responses would be rewarded. To evaluate response bias, asymmetric reinforcement was utilized—correct identification of either the short or long mouth was reordered three times more frequently (the rich stimulus) than correct identification of the other mouth ("lean stimulus"). The reinforcement allocation and key assignments were counterbalanced across subjects. The task was administered in three (3) blocks or sessions of 50 long versus 50 short mouths. The rich/lean versus long/short associations are balanced across subjects.

Figure 12:
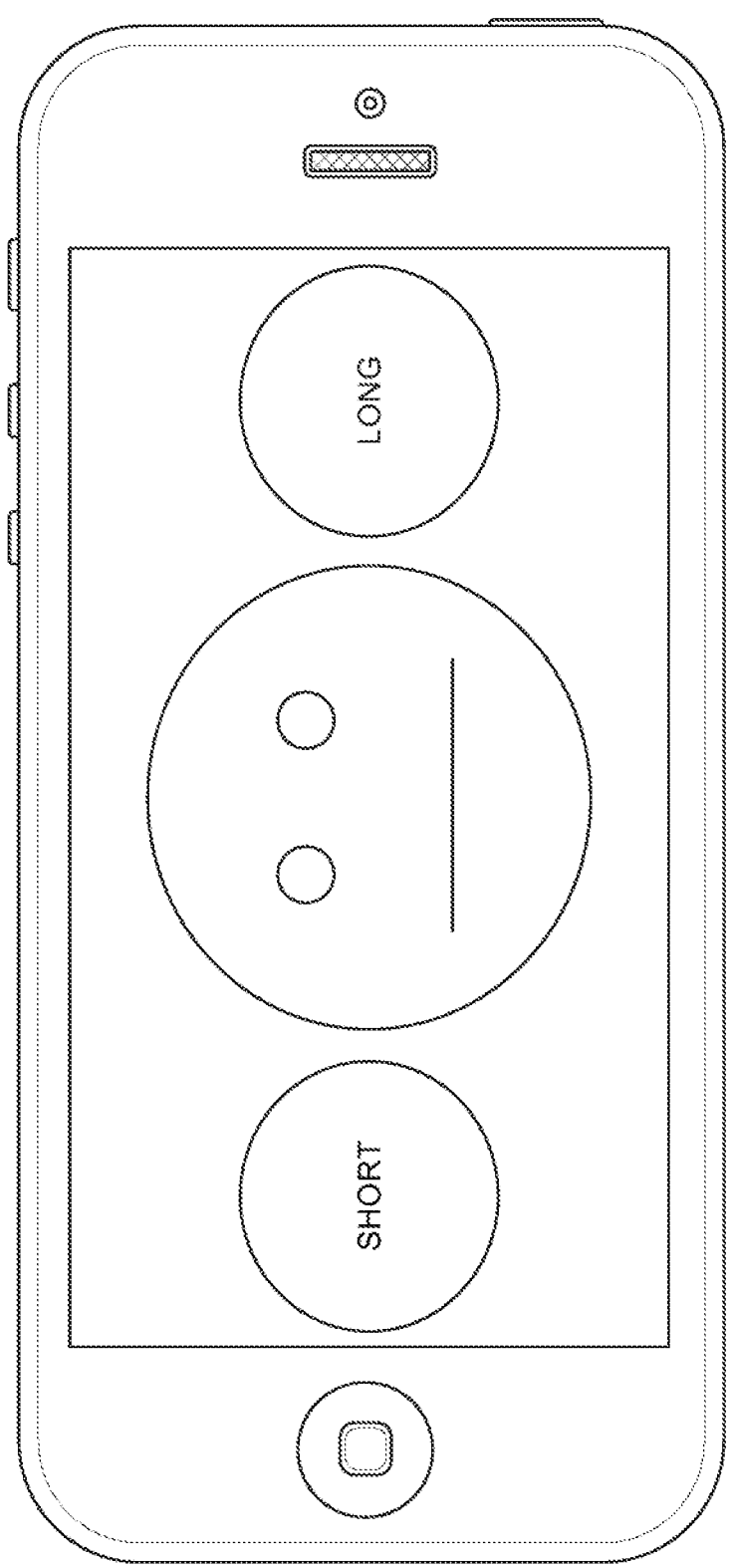
FIG. 12 depicts an overview of a system including a mobile device and an interface for implementing a task, according to some implementations of the present disclosure.

FIG. 12 illustrates an example of the task implemented in a user interface of a mobile device with a touch screen. A patient would be presented with the image shown in FIG. 12, and the patient would then select using the touchscreen user interface, the circle with the text "Short" on the left or "long" on the right. In other examples, the stimulus and response buttons may appear as illustrated in FIG. 11. The local processor would then receive the user input, time stamp, and record the information in a local memory and/or a database to accumulate the patient's responses. For instance, the control system would determine the time between when the mouth was displayed and the time stamp of receiving the patient's response to assess the patient's reaction time. Additionally, the control system would determine the PRT outcome measures described below with reference to FIG. 13, especially the response bias between the hit rates of the rich and lean stimuli. These measures may then be processed as input features to various models disclosed herein.

FIG. 13 illustrates the PRT outcome measures per Block of the PRT task. Measures used include response bias, discriminability, reaction time, hit rate (rich), and hit rate (lean).

Effort-Expenditure for Rewards Task (EEfRT)

The EEfRT task measures the objective motivation component of reward processing. The patient chooses a hard or easy task: (i) hard: the display requests the user click 100 times in 21 seconds using the non-dominant little finger and (ii) easy: the display requests the user click 30 times in 7 seconds using the dominant index finger. Once the assessment is initiated, the control system sends instructions to display instructions for the user to click a certain amount of times after the user selects hard or an easy assessment. Then, the control system sends instructions to display a reward amount and probability:
1) Amounts: $1 (easy); $1.24-$4.30 (hard)
2) Probabilities: 12% (low); 50% (medium); 88% (high)

Figure 14:
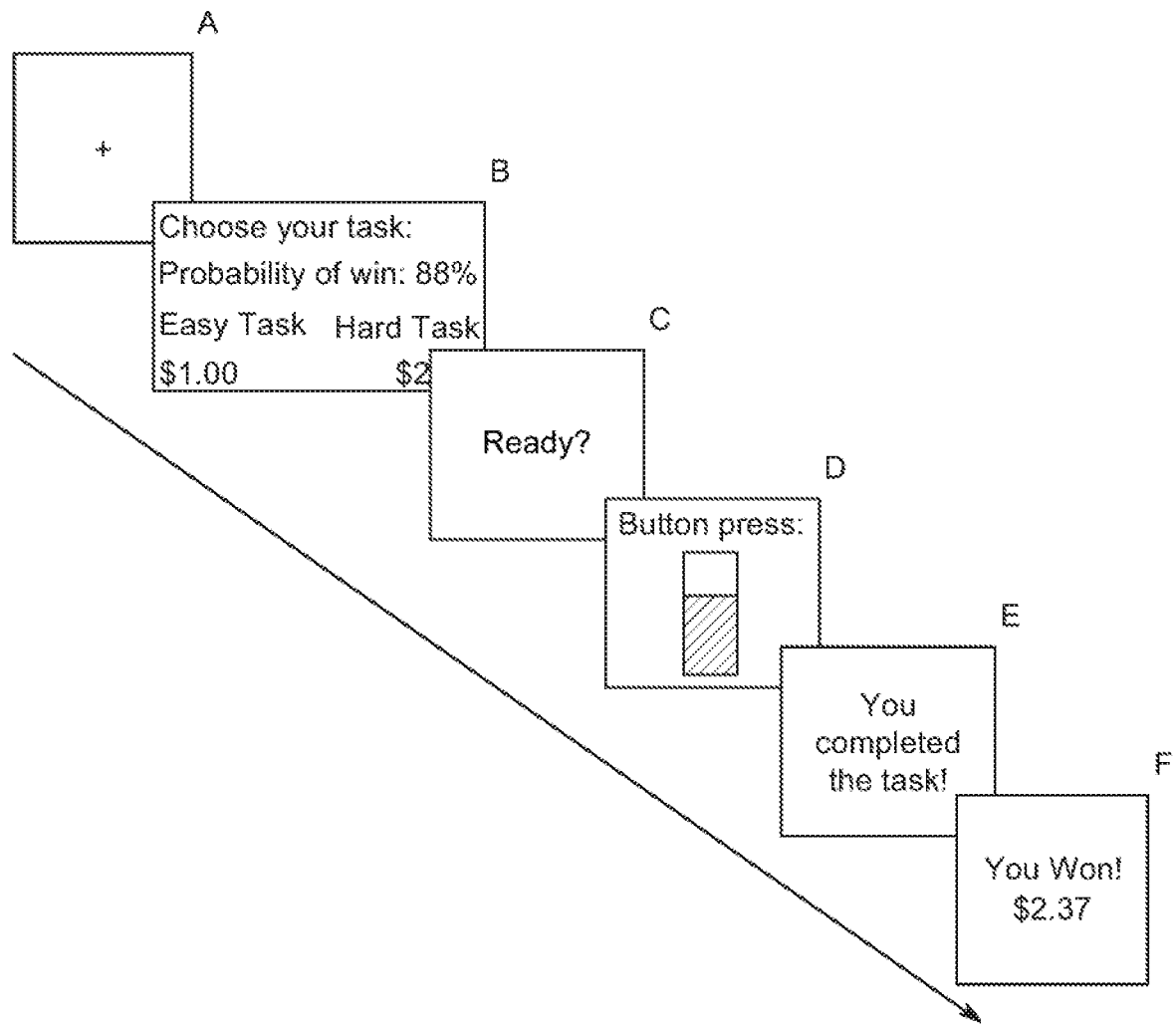
FIG. 14 depicts a schematic of a progression of one or more screens shown to a patient during a EEfRT task, according to some implementations of the present disclosure.

Then, once the control system initiates the test, the clicks from the user's mouse or screen taps are recorded and time stamped, to determine how many clicks the user finished within the time periods. FIG. 14 illustrates a schematic example of the user interface displayed items and linear progression of the task. For instance, the user starts the task, selects the probability ad easy or hard, once they are ready they select ready and presses the correct button. The control system will determine how much money the user won.

Facial Expression Recognition Task (FERT)

The FERT task measures the bias in emotion recognition and processing. The control system sends instructions to the display to display images of humans with six different basic emotions (plus neutral):
- Happiness;
- Fear;
- Anger;
- Disgust;
- Sadness;
- Surprise; and
- Neutral The subject that is displayed buttons on the interface (in some examples) that allow the patient to select the emotion the patient believes matches the emotion expressed on the face in the image. In this example, ten (10) intensity levels of the emotion were presented. The outcomes measured by the test include:
- the accuracy, overall and per each intensity level;
- misclassification;
- average reaction time;
- target sensitivity; and
- response bias.

Demographics

In some examples the interface requested the patient provide their demographic information (or it could have been retrieved from a database). In some examples, this information was used as input into the classifiers.
- Age
- Sex The primary outcome of the study utilized was the clinical scale MADRS total at week 8. Predictive models were built using the disclosed systems and methods that label a high responder as those patients with a MADRS response that decrease by 50% from their initial baseline. In some models, the features set utilized included MADRS, HADS-A, HADS-D, Age, PRT, FERT, and EEfRT, with the scales and tasks input at week 0 as features.

Biochemical Biomarkers

In one example, biochemical or biomarkers, including Tumor Necrosis Factor, were also utilized to determine whether they could be useful to stratify patients as part of the disclosed Bayesian Decision Lists. The biochemical biomarkers tested included:
- Nociceptin
- Interleukin 6
- Interleukin 1 Beta
- Interferon Gamma Interleukin 10
Interleukin 2
Tumor Necrosis Factor
C Reactive Protein As discussed herein, these biomarkers were processed by the models disclosed herein for generating a Bayesian Rule List. Accordingly, in at least one example, Tumor Necrosis Factor was output as a rule in a Bayesian Decision List as described further below.

Models to Stratify Patients

To build the models to stratify the patients from the data, first, forward selection using logistic regression with elastic net regularization was utilized as disclosed herein. This identified the top features from the full feature set that included the tasks, scales and demographics that had the greatest ability to separate patients into three groups: (i) BTRX-246040 responders, (ii) placebo responders, and (iii) non-responders.

In this example, linear regression was first utilized to separate the groups using the top features identified as inputs. This was done in part by simulating a multi-verse scenario where each patient goes through both the drug arm and the placebo arm, and then taking the difference in the predicted Week8 outcome scores across the two simulated arms (see Webb et al., 2019, paper, Personalized prediction of antidepressant v. placebo response: Evidence from the EMBARC study. Psychological Medicine, 49(7), 1118-1127) which is incorporated by reference herein in its entirety.

As illustrated in FIG. 16, the linear regression model resulted in good identification of patients that were higher responders to BTRX-246040. The cutoff between groups was determined by a compromise between maximizing the effect size and maintaining an adequate sample size within each subgroup.

In some examples, the top features derived from the forward selection model could be utilized to build predictive models that could separate new patients into the different responding groups. In those examples, the features could be pre-processed from the tasks, demographic data, and scales answers, and then input into a linear or logistic regression model to output classifications of new patients.

In other examples, a rule miner and BRL algorithm could be utilized to developed rules to separate the groups identified using forward selection. In that example, the output labels for the data used by the rule miner could be derived from the three groups separated by the linear regression model (groups and data shown in FIG. 16). Then, literal rules could be developed using a Bayesian Rule List model that would separate the patients into these categories based on the features identified in forward selection to output a Bayesian Decision List. Those rule lists, could then be utilized to separate new patients based on whether they would respond to BTRX-246040, placebo, or neither. Thus, high responders to BTRX-246040 could be identified and treated with the drug. In other examples, the disclosed systems and methods could stratify patients to identify high responders to other neuropsychiatric drugs.

The resulting algorithms could be saved on a remote database server, or locally, including on the memory of a handheld computing device that administers the scales and/or tasks disclosed herein. Accordingly, patients could be administered scales questionnaires, tasks, and submit demographic information on a mobile device or other computing device. Next, the computing device and control system may process the data to be input as features into a Bayesian Rule List, and then output whether or not the Patient is likely a high responder for BTRX-246040 or other drugs in other examples.

Results

Figure 15A:
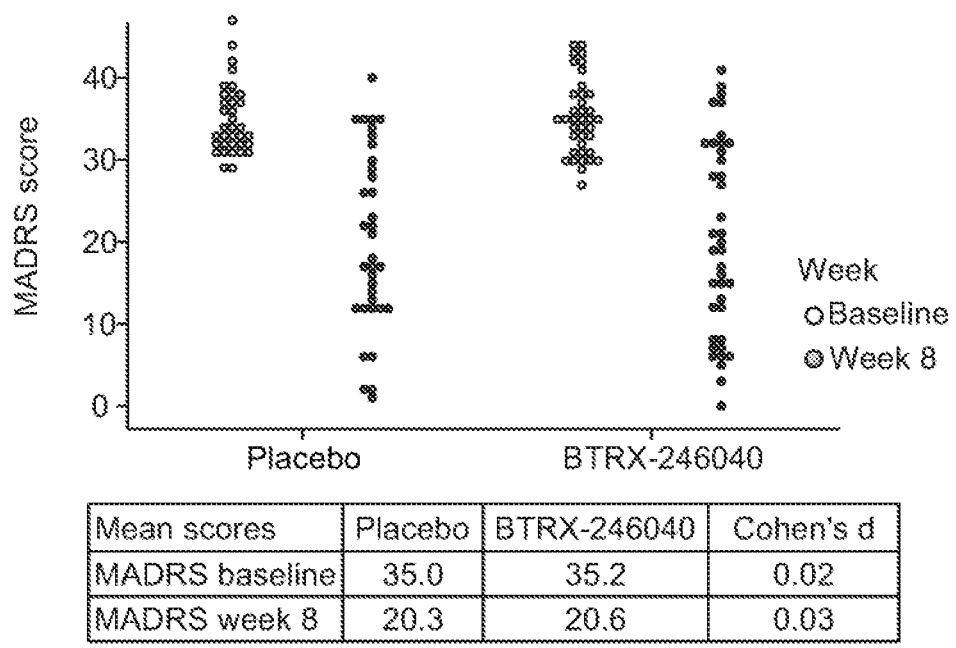
FIG. 15A depicts a graph and a corresponding table of the graph showing treatment effects of a study disclosed herein, according to some implementations of the present disclosure.
Figure 15B:
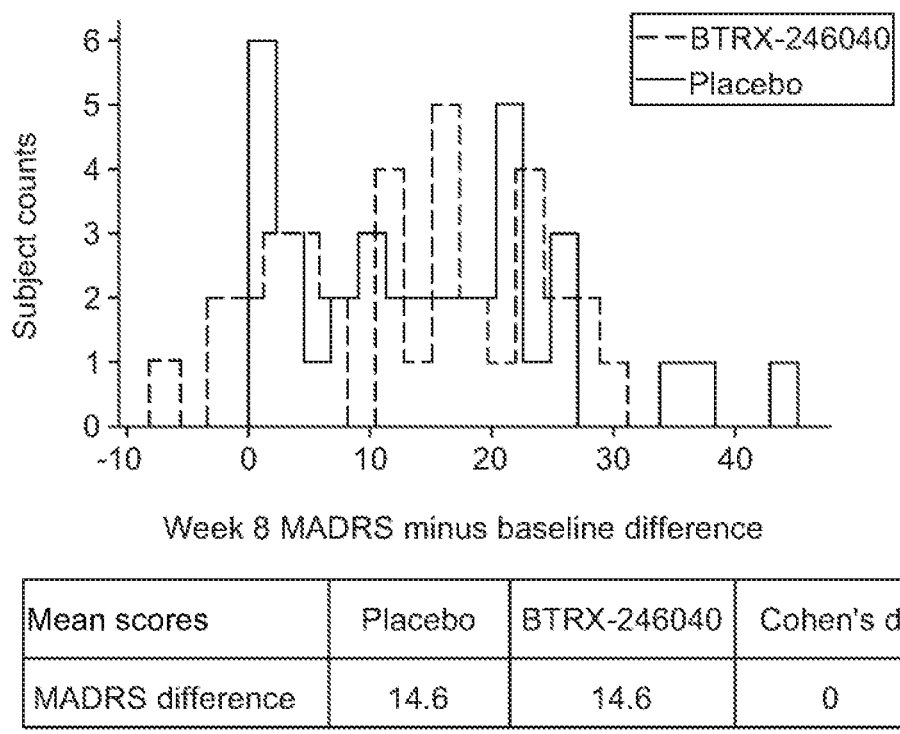
FIG. 15B depicts a graph and a corresponding table of the graph showing treatment effects of a study disclosed herein, according to some implementations of the present disclosure.

The group level treatment effects of the disclosed study were similar between the treatment and placebo groups. Accordingly, in this study, BTRX-246040 did as well as the placebo across all subjects as illustrated in FIGS. 15A-15B, which depict graphs and tables showing treatment effects.

Figure 16A:
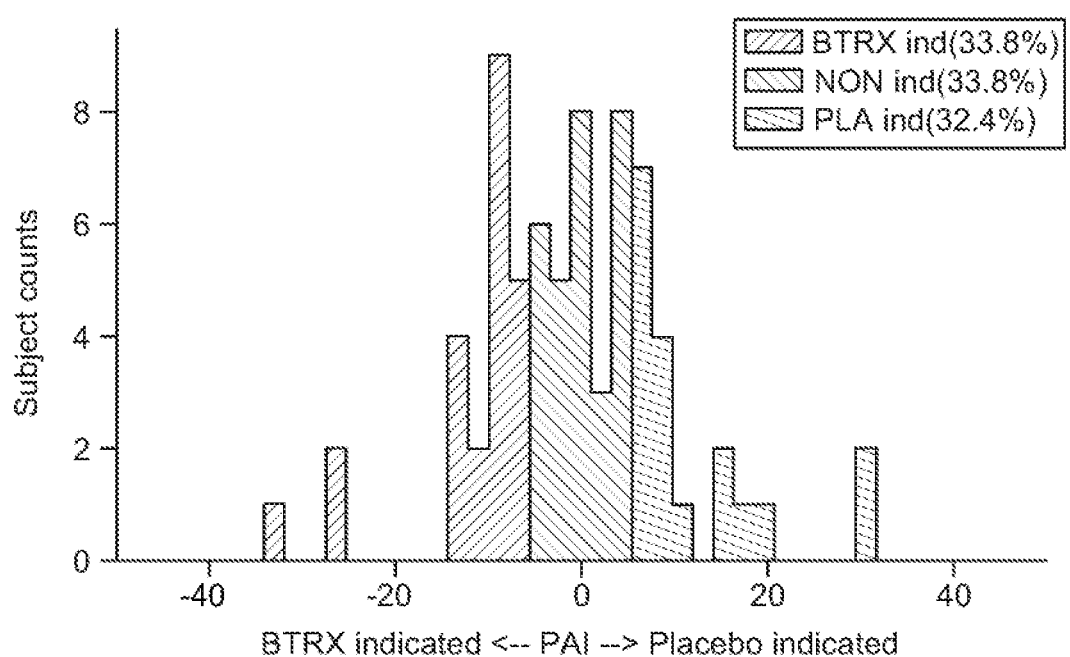
FIG. 16A depicts a graph showing treatment effects of a study disclosed herein, according to some implementations of the present disclosure.
Figure 16B:
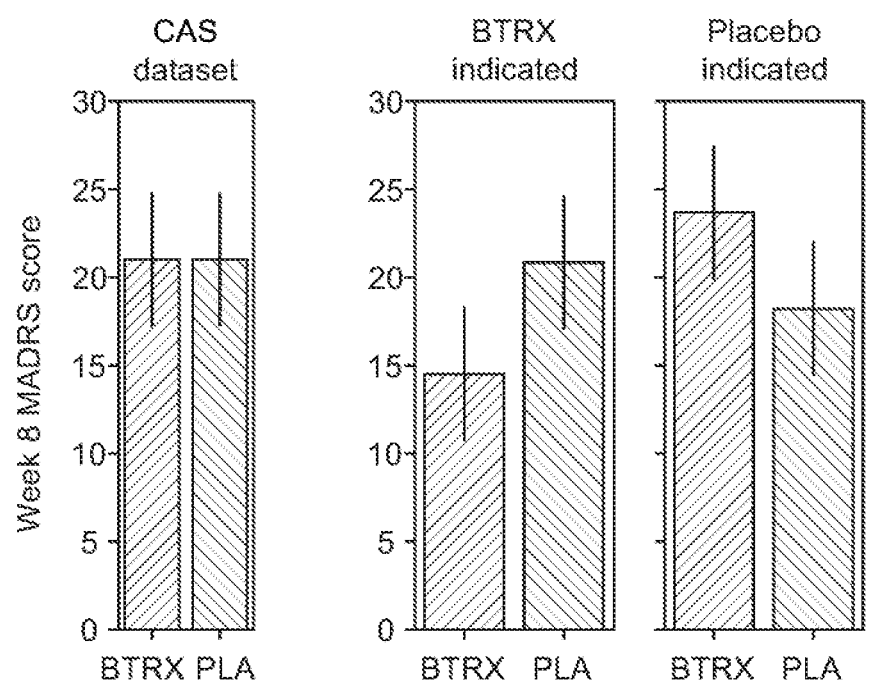
FIG. 16B depicts graphs and a corresponding table of the graphs showing treatment effects of a study disclosed herein, according to some implementations of the present disclosure.
Figure 17A:
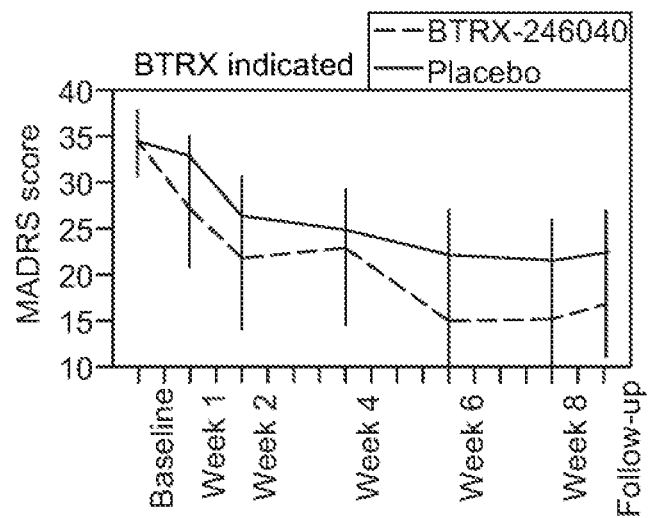
FIG. 17A depicts a graph showing treatment effects under a BTRX indicated model disclosed herein; according to some implementations of the present disclosure.
Figure 17B:
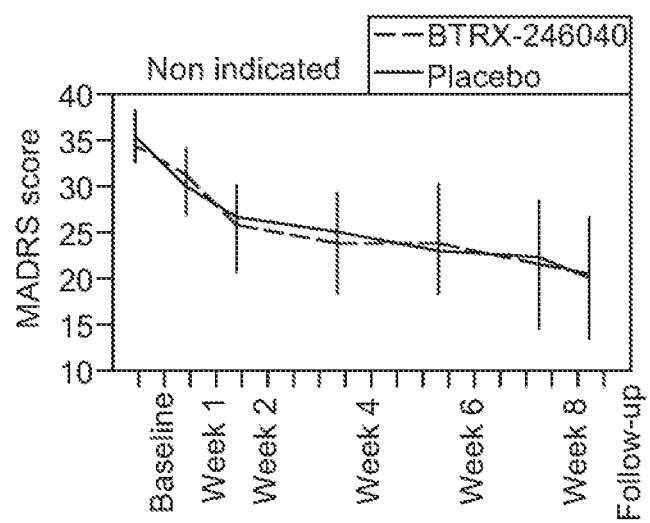
FIG. 17B depicts a graph showing treatment effects under a non-indicated model disclosed herein; according to some implementations of the present disclosure.
Figure 17C:
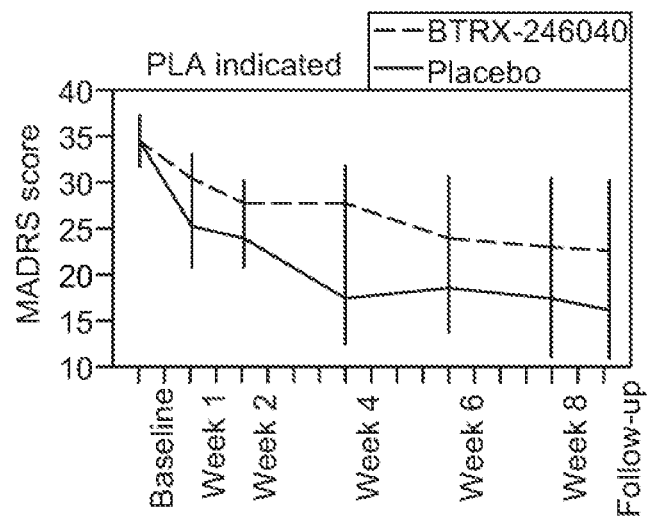
FIG. 17C depicts a graph showing treatment effects under a PLA indicated model disclosed herein; according to some implementations of the present disclosure.
Figure 17D:
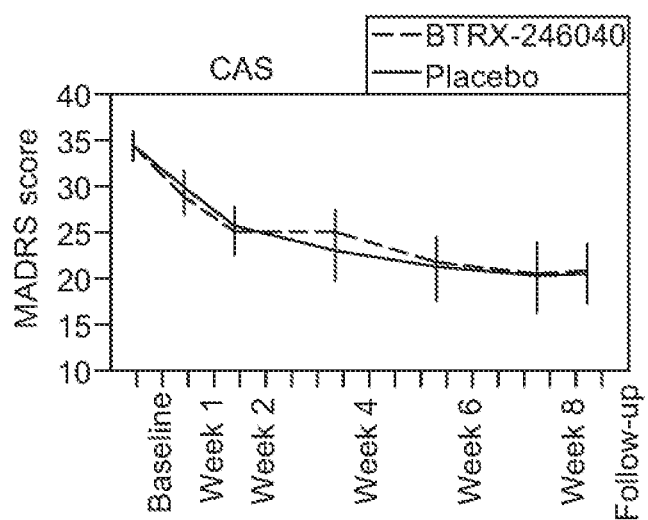
FIG. 17D depicts a graph showing treatment effects under a CAS model disclosed herein; according to some implementations of the present disclosure.

In addition, as illustrated in FIGS. 16A-16B, the disclosed classifiers were able to identify patients that would be higher responders to BTRX-246040 by a greater than 5-point change on the MADRS scale after the 8-week study. Additionally, the disclosed classifiers were able to identify patients that would be higher responders to the placebo. Furthermore, the table below illustrates the logistic regression models built with forward selection models (with elastic net regularization) had good accuracy and AUC in separating the high responding to BTRX-246040 and high responders to Placebo groups:

TABLE 5

Assessment of Models

| BTRX MODEL (ROC-AUC = 0.72, Acc = 0.63) | PLA MODEL (ROC-AUC = 0.87, Acc = 0.81) |
|---|---|
| Age | EEfRT Completion Rate - Low |
| HADS-A Total Score | PRT Response Bias - Block 2 |
| HADS-D Total Score | PRT Response Bias - Block 3 |

Additionally, FIGS. 17A-17D illustrate that the response prediction from baseline data is stable over time. Specifically, the models utilized only baseline data to make a prediction about the subjects at week 8—without access to intervening data after subjects began the study. With only baseline data, the subjects identified by the models as responders to BTRX-246040 and placebo both maintained improved MADRS scores at weeks 1, 2, 4, and 6. Thus, with only baseline data, the models were able to identify higher responders to placebo and BTRX-246040 that was very consistent over time—a surprisingly accurate and stable stratification of treatment and placebo responders.

Figure 18A:
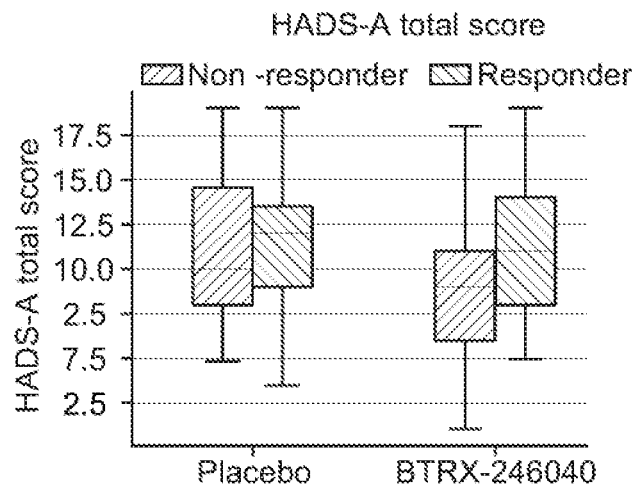
FIG. 18A depicts a graph showing a top feature of HADS-A total score for responders versus non-responders, according to some implementations of the present disclosure.
Figure 18B:
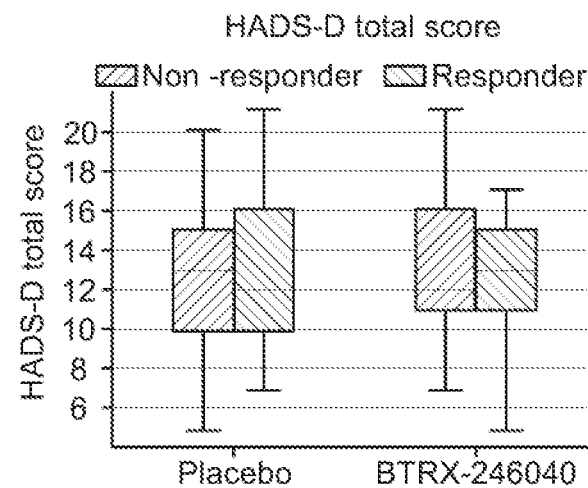
FIG. 18B depicts a graph showing a top feature of HADS-D total score for responders versus non-responders, according to some implementations of the present disclosure.
Figure 18C:
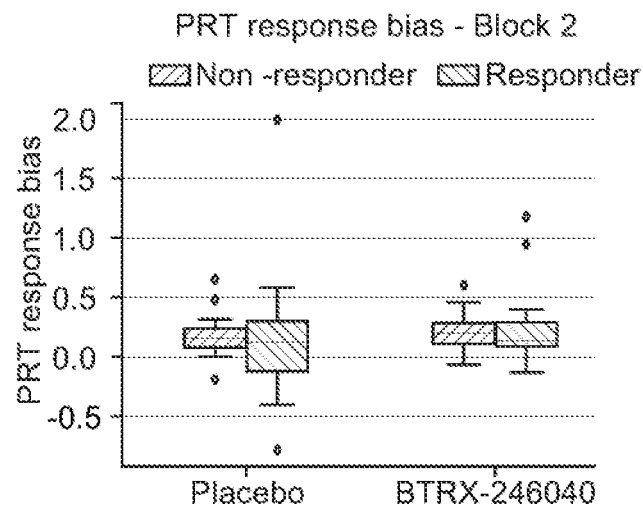
FIG. 18C depicts a graph showing a top feature of PRT response bias (Block 2) for responders versus non-responders, according to some implementations of the present disclosure.
Figure 18D:
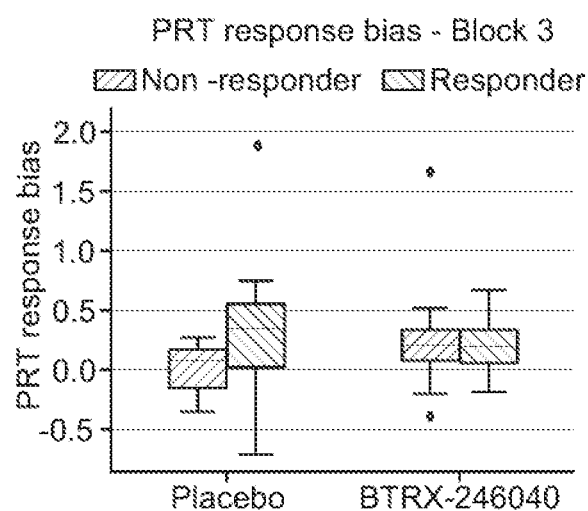
FIG. 18D depicts a graph showing a top feature of PRT response bias (Block e) for responders versus non-responders, according to some implementations of the present disclosure.
Figure 18E:
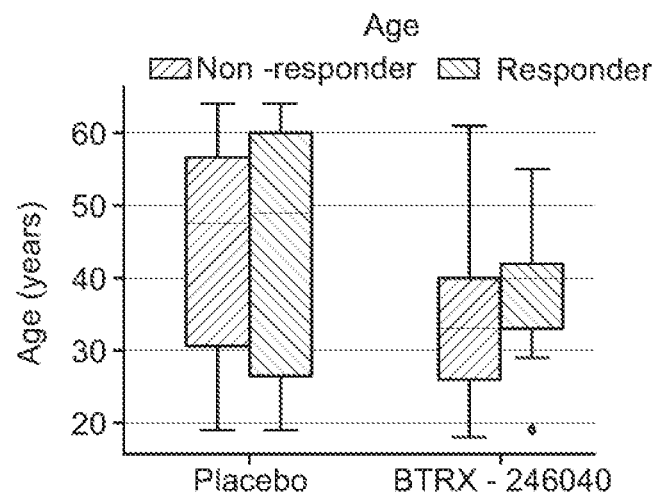
FIG. 18E depicts a graph showing a top feature of age for responders versus non-responders, according to some implementations of the present disclosure.
Figure 18F:
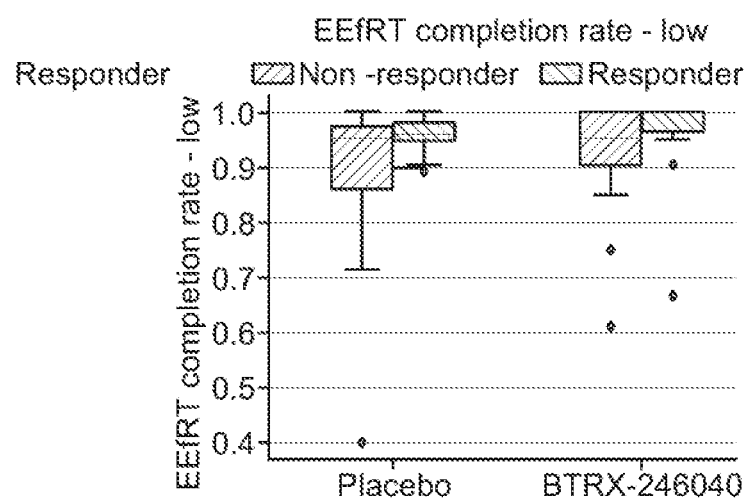
FIG. 18F depicts a graph showing a top feature of EefRT completion rate for responders versus non-responders, according to some implementations of the present disclosure.

FIGS. 18A-18F illustrate the top features that separated responders from non-responders to the placebo and BTRX-246040 treatment. For example, FIG. 18A depicts a graph showing a top feature of HADS-A total score; FIG. 18B depicts a graph showing a top feature of HADS-D total score; FIG. 18C depicts a graph showing a top feature of PRT response bias—Block 2; FIG. 18D depicts a graph showing a top feature of PRT response bias—Block 3; FIG. 18E depicts a graph showing a top feature of age; FIG. 18F depicts a graph showing a top feature of EEfRT completion rate; These features were identified with Forward Feature Selection methods disclosed herein.

Based on the results, some of the classifiers disclosed herein increased accuracy when different modalities were included in the Bayesian Rule Lists, for instance clinical scales and tasks based assessments. Accordingly, given the numerous modalities available for neuropsychiatric testing, there are a plethora of features available for input into various models. The disclosed systems and methods have an unprecedented ability to identify the most predictive features using forward feature selection, and then process those features with a rule miner to output understandable rule lists for accurately stratifying patients based on those features. In other examples, a rule miner could potentially be used on the broader list of features to output a rule list to stratify patients.

Figure 19B:
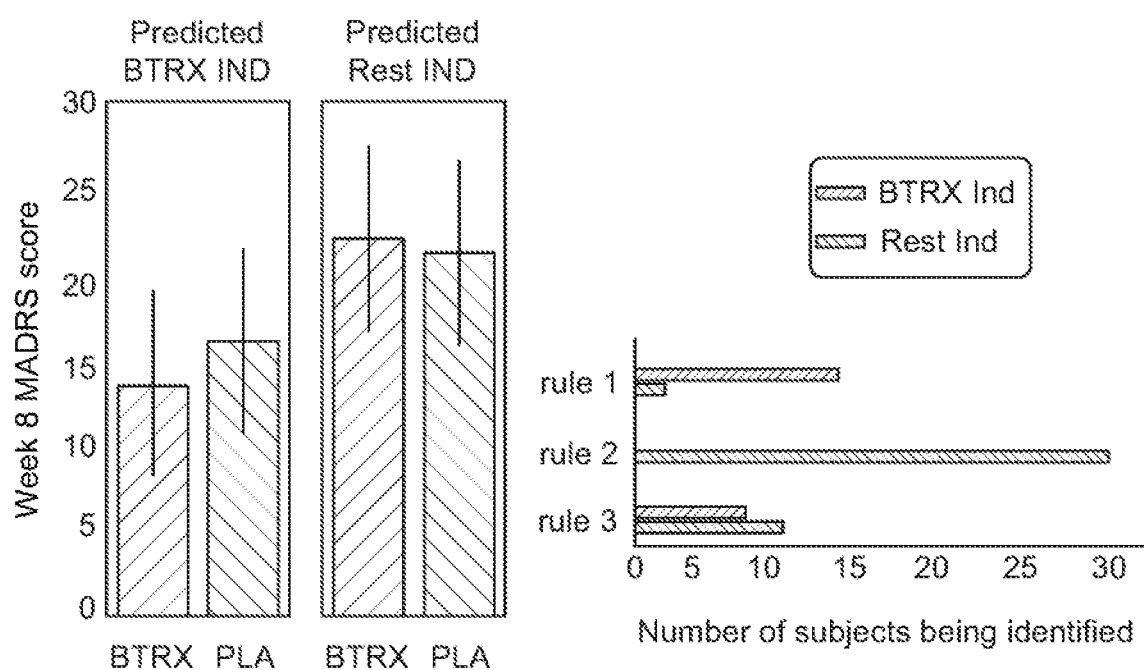
FIG. 19B depicts graphs showing treatment responses between BTRX group and Rest group, and a bar graph showing a number of subjects being identified by the rules, according to some implementations of the present disclosure.

FIGS. 19A-19B illustrate an example of this combination approach that has been found to be very advantageous. As illustrated, the bar graphs in FIG. 19B depict the patient groups that were stratified using Forward Feature Selection and linear regression. However, based on those separations alone, it is not clear what features are most important to stratify the patients for each group. For instance, in FIGS. 18E-18F, it is not known which scales, tasks, or other input features would be most important to identifying patients that are higher responders to BTRX-246040 based on the outputs of the linear regression model.

Therefore, the rule miner and BRL algorithm was applied to the results, and a set of rules were identified that specifically could identify higher responders to BTRX-246040 (see FIGS. 18A-18F). Interestingly, as illustrated in FIGS. 19A-19B, this only included the FERT task response bias to the angry expression, and a specific threshold of a HADS-A score. Accordingly, the rule miner and BRL algorithm is extraordinarily valuable in interpreting the basis for stratifying the groups which also could allow one to design more efficient screening systems for patients (only certain tasks, and scales would need to be administered in the future to screen patients instead of administering all of the questions and all of the tasks).

Figure 20B:
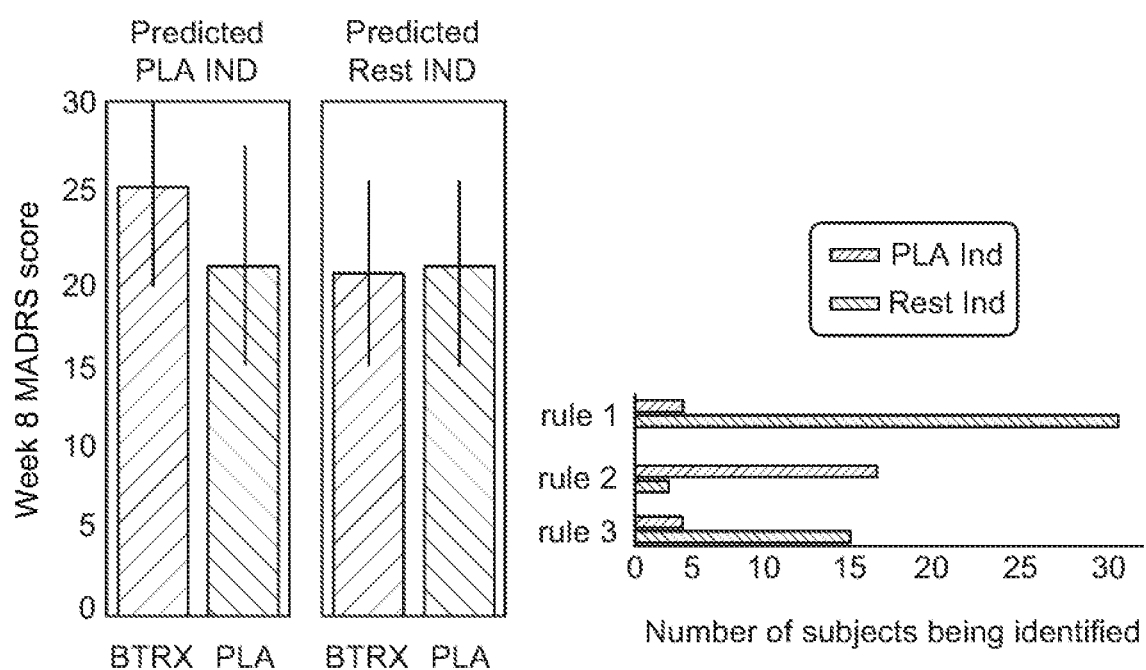
FIG. 20B depicts showing treatment responses between PLA group and Rest group, and a bar graph showing a number of subjects being identified by the rules, according to some implementations of the present disclosure.

FIGS. 20A-20B further illustrate additional Bayesian Decision Lists extracted from the data set and output by the BRL model after being assigned labels from the outputs of the Forward Features Selection and linear regression models. These include Bayesian Decision Lists to identify patients would respond to placebo. Thus, the disclosed systems and methods can generate Bayesian Rule Lists to screen out patients that are higher responders to placebo, in the design of clinical trials for instance.

Figure 25B:
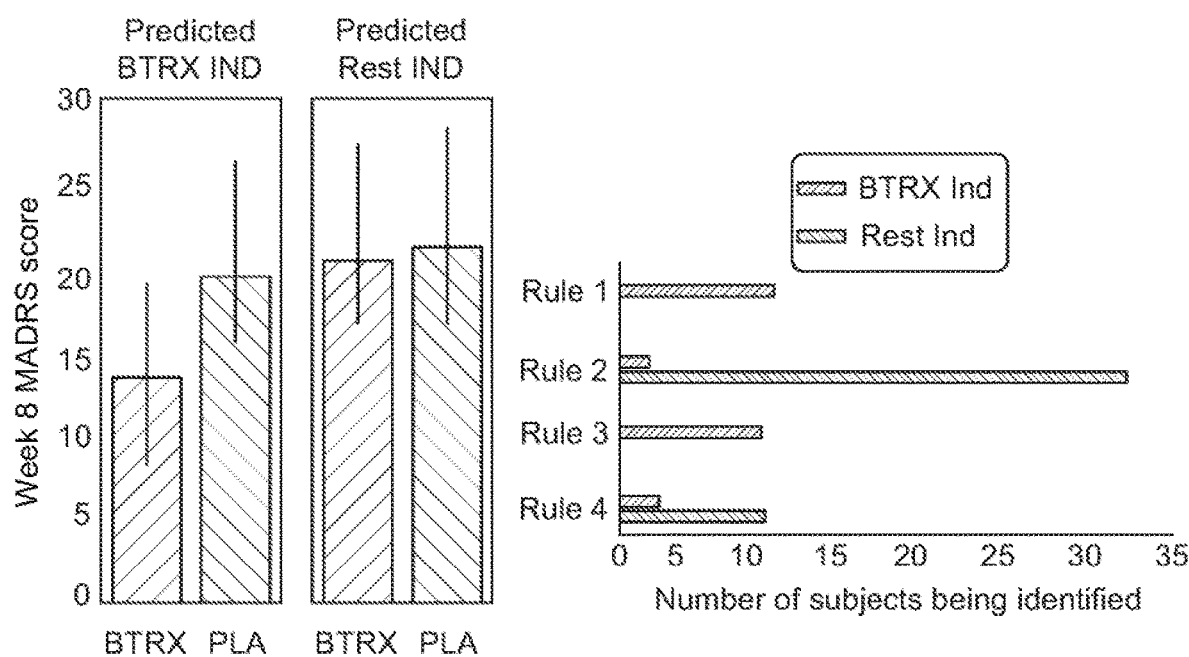
FIG. 25B depicts graphs showing treatment responses between BTRX group and Rest group, and a bar graph showing a number of subjects being identified by the rules, according to some implementations of the present disclosure.

FIGS. 25A-25B illustrate a Bayesian Decision List that incorporated Tumor Necrosis Factor, a biochemical or wet biomarker into the rule list. More specifically, FIG. 25A depicts a further pseudocode for a BRL output incorporating Tumor Necrosis Factor into the rule list, according to some implementations of the present disclosure; and FIG. 25B depicts graphs showing treatment responses between BTRX group and Rest group, and a bar graph showing a number of subjects being identified by the rules, according to some implementations of the present disclosure.

This is surprising, as this rule list combines four different and disparate types of modalities into a single, short Bayesian Decision List capable of stratifying patients: (i) demographics, (ii) clinical scales, (iii3) tasks, and (iv) biochemical markers. Additionally, the rule list reliably separates higher responders to BTRX-246040. Accordingly, this data demonstrates that the disclosed systems and methods for generating Bayesian Decision Lists may surprisingly and accurately take into account even biochemical markers in combination with a variety of other biomarker modalities.

Example 4

Treatment Response to CERC-501

In another example, during a phase 2a study known as FAST-MAS was run to evaluate the Kappa Opioid Receptor ("KOR") as a target for the treatment of mood and anxiety spectrum disorders. Additionally, CERC-501, it's uses, indications, treatments, and forms are disclosed in PCT Publication No. WO2018170492, filed Mar. 16, 2018, titled "Kappa Opioid Receptor Antagonists and Products and Methods Related Thereto" which is incorporated by reference herein in its entirety. During the trial, CERC-501 was tested to see whether it engaged key neural circuitry related to the hedonic response.

The FAST-MAS trial included a 30-day screening period, followed by 8 weeks of active treatment, follow up 12 weeks of off-drug follow up after baseline. The study included 80 patients randomized (of 163 enrolled) to include 45 on CERC-501 and 44 to the Placebo. The patients received 10 m daily for the 8 weeks of active treatment.

Patients were eligible for enrollment if they met both:

(i) DSM-IV TR criteria for at least one of:
  MDD
  Bipolar I or II Depressed
    GAD
  Social Phobia
  Panic Disorder
  PTSD; and
(ii) SHAPS score of ≥20

The diagnosis breakdown was accordingly to the following table:

TABLE 6

Primary Diagnosis Breakdown

| MINI DIAGNOSIS | TOTAL | PLACEBO | TREATMENT |
| --- | --- | --- | --- |
| MDD | 33 | 17 | 16 |
| GAD | 11 | 5 | 6 |
| BD I | 5 | 3 | 2 |
| BD II | 4 | 0 | 4 |
| Social Anxiety Disorder | 4 | 2 | 2 |
| PTSD | 2 | 2 | 0 |
| Panic Disorder | 2 | 1 | 1 |
| Total | 61 | 30 | 31 |

Furthermore, the primary outcome measures were the following measures included in Table 7 below. These include the fMRI, the SHAPS scale, and the PRT task as disclosed herein.

TABLE 7

Primary Outcome Measures

| TYPE | MEASURE | DESCRIPTION |
| --- | --- | --- |
| Primary | fMRI MID Task | Change in Ventral Striatal Activation Occurring in Anticipation of Reward During the Monetary Incentive Delay Task Measured by fMRI |
| Secondary | SHAPS | Clinical Anhedonia Measured by the Snaith-Hamilton Pleasure Scale (SHAPS; Total Score) |
| Secondary | PRT Task | Change in Behavioral Measure of Anhedonia Using the Probabilistic Reward Task |

Furthermore, the schedule of scales assessed included the following timeline:

TABLE 8

Schedule of Scales Assessed

| SCALE NAME | SCREENING | BASELINE | STUDY DRUG TREATMENT | | | END OF TREATMENT | FOLLOW-UP |
|---|---|---|---|---|---|---|---|
| Visit | 1 | 2 | 3 (Phone) | 4 | 5 | 6 | 7 | 8 |
| Day | D − 30 to D − 1 | D 0 | D 7 | D 14 +/−4 | D 28 +/−4 | D 42 +/−4 | D 56 +/−4 | D 84 +/−4 |
| Week |  | 0 | 1 | 2 | 4 | 6 | 8 | 12 |
| SHAPS/CGI/TEPS/VAS/PRISE | X | X |  | X | X | X | X | X |
| HAM-D/HAM-A/CPFQ |  | X |  |  |  |  | X |  |
| CSSRS | X | X | X | X | X | X | X | X |

Results

When applied to the whole patient cohort, CERC-501 illustrated a difference in the outcome and treatment response.

The data was first analyzed using a personalized advantage index and identifying the top features through forward feature selection. The following table indicates the top features identified using the forward feature selection process as disclosed herein.

TABLE 9

Top Features identified using Forward Features selection.

| KORA MODEL (ROC-AUC = 0.80, Acc = 0.73) | PBO MODEL (ROC-AUC = 0.90, Acc = 0.82) |
|---|---|
| HAMD 3 (−): Suicide | HAMD 4 (−): Initial Insomnia |
| TEPS 1 (−): Can't wait to see movie w/ favorite actor | HAMA 7 (−): General somatic symptoms |
| HAMD 16 (−): Weight loss | SHAPS 13 (−): Get pleasure from helping others |
| CPFQ 7 (−): Mental acuity | HAMD 16 (+): Weight loss |
| SHAPS 5 (−): Enjoy a warm bath or refreshing shower | |
| HAMA 4 (−): Insomnia | |
| HAMA 10 (−): Respiratory symptoms | |
| HAMA 11 (+): GI symptoms | |

Figure 26B:
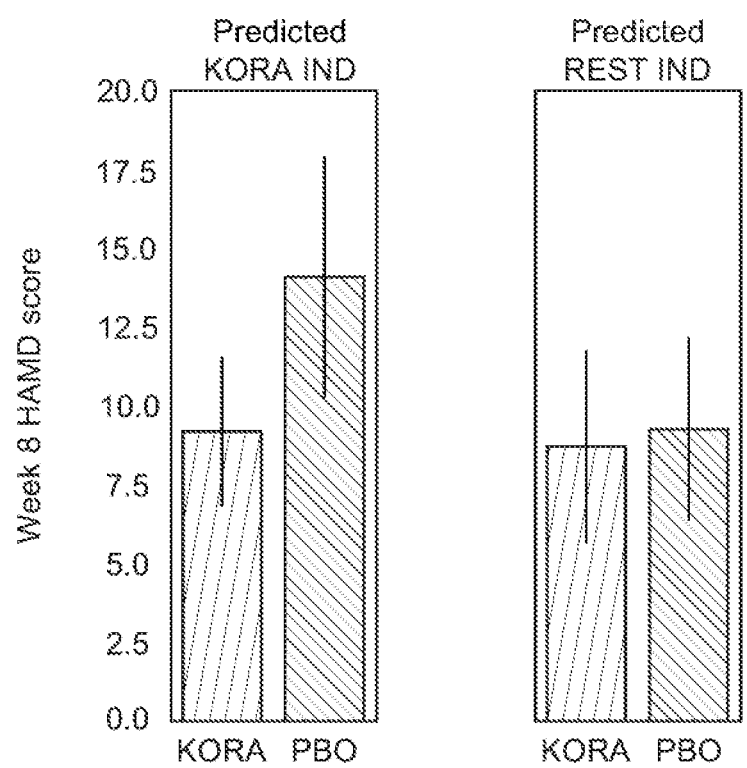
FIG. 26B depicts a graph showing treatment responses between KORA group and Rest group, according to some implementations of the present disclosure.

Interestingly, in this example the top features were all scales modality features. Next, these features were processed using the disclosed systems and methods to output a Bayesian Decision List illustrated in FIGS. 26A-26B. More specifically, FIG. 26A depicts yet another pseudocode for a BRL output using a disclosed rule mining technique and a BRL model, according to some implementations of the present disclosure; and FIG. 26B depicts a graph showing treatment responses between KORA group and Rest group, according to some implementations of the present disclosure.

For instance, a rule miner was applied to the features and outcomes to output a rule set, and a BRL model was applied to the rule set to output the decision list. This list reliable separated patients that responded to CERC-501 as illustrated by the FIGS. 26A-26B. The impact of CERC-501 was greater on the patients identified using the Bayesian Decision Lists than the impact generally on the patients that received the active treatment, confirming that the disclosed systems and methods can reliably identify higher responders, including for drugs that target KOR.

Figure 27B:
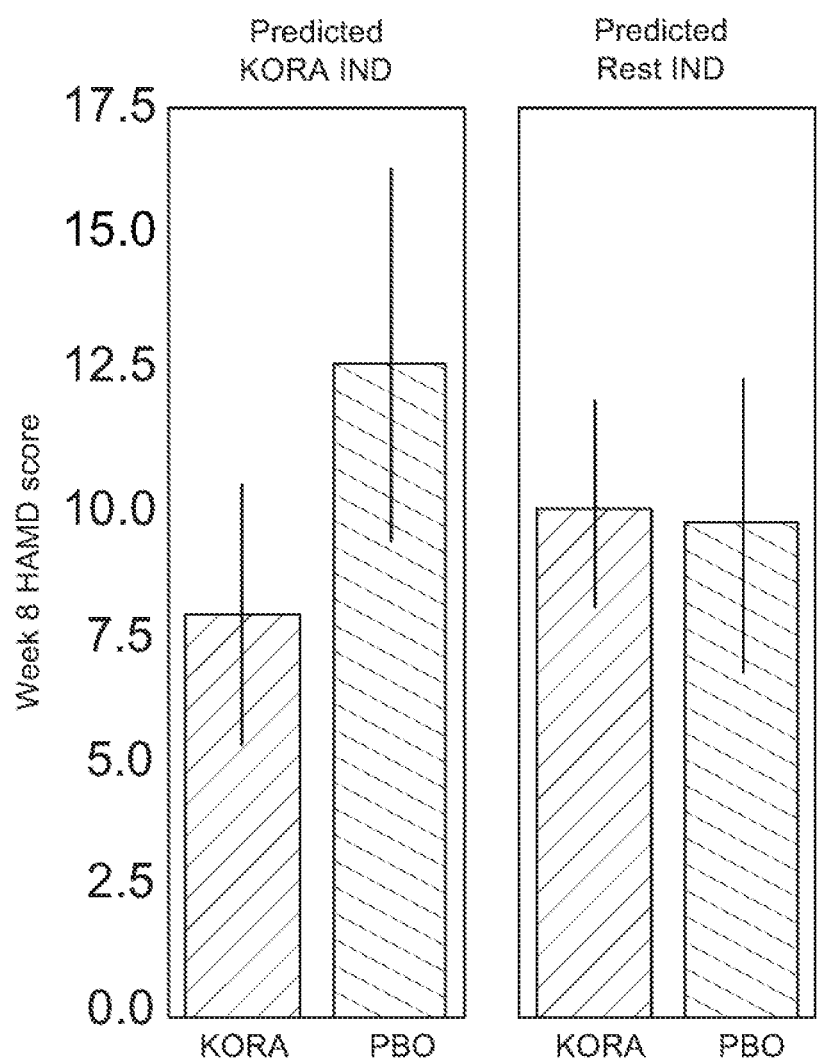
FIG. 27B depicts a graph showing treatment responses between KORA group and Rest group, according to some implementations of the present disclosure.

Furthermore, FIGS. 27A, 27B, and 28 show additional rule lists that were generated according to the disclosed systems and methods that were capable of identifying higher responders for CERC-501. More specifically, FIG. 27A depicts a pseudocode for a BRL output using a disclosed rule mining technique and a BRL model, according to some implementations of the present disclosure; FIG. 27B depicts a graph showing treatment responses between KORA group and Rest group, according to some implementations of the present disclosure; and FIG. 28 depicts an additional pseudocode for a BRL output using a disclosed rule mining technique and a BRL model, according to some implementations of the present disclosure.

In some of these rule lists, task data was included in the rules, including the PRT task disclosed herein. Accordingly, the FAST-MAS study confirms that the disclosed technology may be utilized to generate rule lists that are capable of stratifying patients to identify higher responders to drugs that target the Kappa Opioid Receptor.

Example 5

Voice and Facial Modalities

In some examples, the disclosed technology may utilize data and features from audio and video recordings of patients performing speaking tasks. For instance, in some examples, the disclosed Bayesian Decision Lists may incorporate features from these speaking tasks to stratify patients (possibly in combination with other disclosed modalities including scales). Specifically, the speaking features may include the following modalities:
  1) audio features from the patient's voice extracted from the recordings during a speaking task;
  2) text features from the words and sentences spoken by the patient during a speaking task; and
  3) video features from the facial expressions of the patient recorded during a speaking task.

Example Speaking Tasks

Accordingly, systems and methods may be utilized to record audio and video data while a patient is performing a speaking task. For instance, a patient may be asked to read aloud a passage, paragraph or other text while a microphone and video camera record the patient speaking. The system may display the instructions on a display or provide audio instructions on the speaker of an interface. This will allow the system to identify audio and visual features relating to how a patient communicates certain passages.

In other examples, a display may present questions to the patient (or questions may be asked to the patient over a speaker) and the microphone and video camera may record the answer provided by the patient. In this example, in addition to analyzing the audio and visual features of the response, the systems and methods may also analyze the answers and words chosen by the patient and they may be inputs into the models disclosed herein.

Systems and Methods for Acquiring Audio and Visual Features of Speaking Tasks

Following are example systems and methods for capturing the audio, visual, and textual features during the speaking tasks. In some examples, a mobile device application will be used to perform the test and capture the data. In other examples, a variety of other computing devices could be utilized in a system that includes a microphone, speaker, camera, display, and interface.

In some examples, only audio or only video data may be captured and/or input into the disclosed algorithms. For instance, a Bayesian Decision List may only include an audio feature or may only include a video (e.g. facial expression) feature. Therefore, to stratify patients, only audio or video data would respectively need to be recorded.

Figure 29:
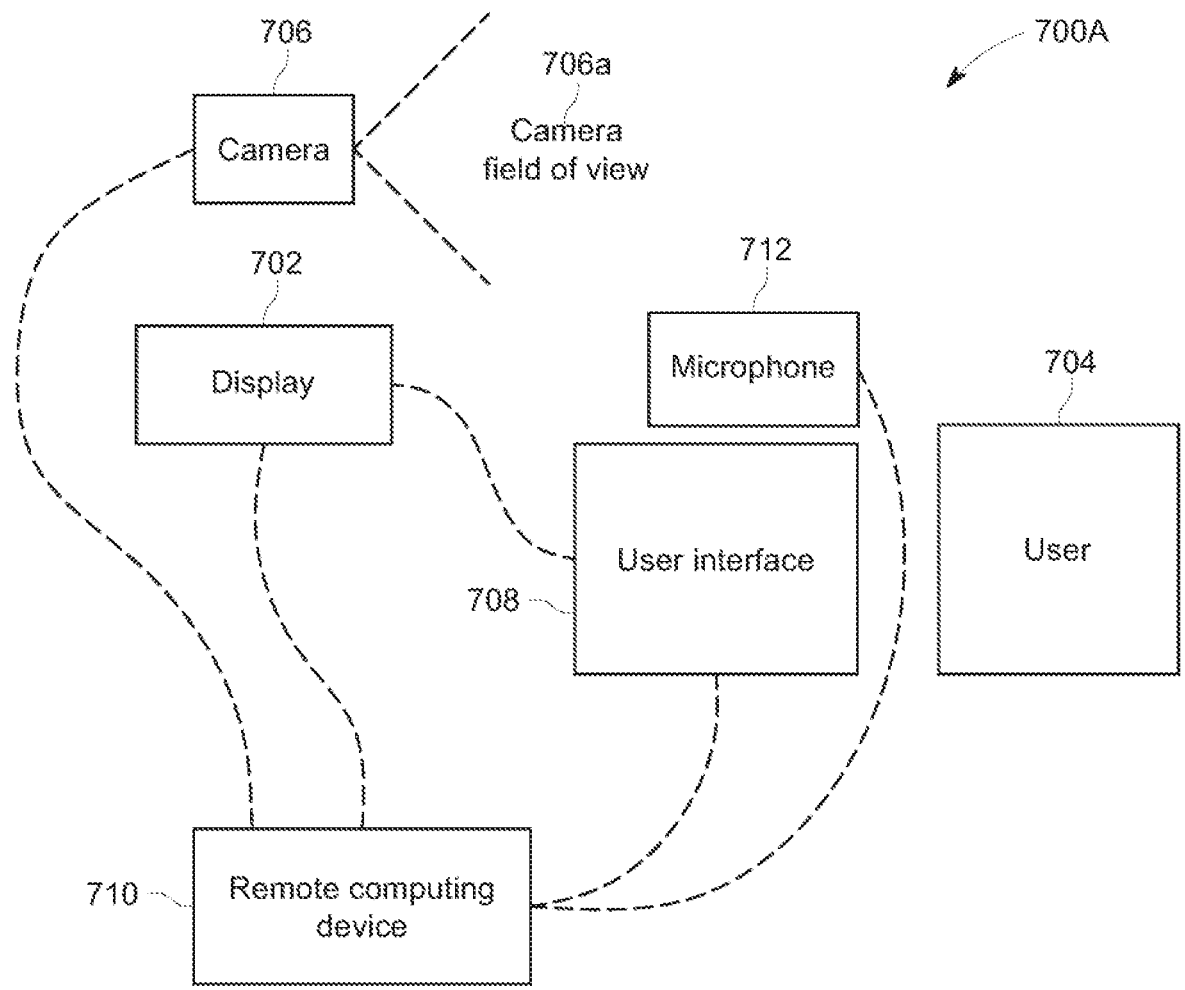
FIG. 29 depicts a system configured to perform various methods of capturing audio and visual data during various tasks disclosed herein, according to some implementations of the present disclosure.

FIG. 29 presents an example system 700A, which can be configured to perform various methods of capturing audio and visual data during various tasks disclosed herein. In particular, system 700A includes a display 702; a user 704; a camera 706; a camera field of view 706a; a user interface 708 including a speaker; a remote computing device 710; and a microphone 712.

The camera 706 captures visual data of an area in front of the camera (area 706a) and in some examples, transmits the visual data to the display 702 and the remote computing device 710. As shown in FIG. 29, a user 704 may position the camera so that their head or face is in the view of the camera 706. In such an example, the camera 706 captures footage of the face of the user 704. In some examples, the camera 706 can be configured to take live video footage, photographs, or images/videos in non-visual wavelengths. In some examples, the camera 706 is configured to start or stop recording based on instructions from the remote computing device 710 or a local processor or computing device. For instance, the application or program running the process may be performed by a remote server, computing device, or a local processor. The camera 706 is communicatively coupled to the display 702 and the remote computing device 710 or a local computing device. In some examples, a smartphone will perform each of these functions.

The user interface 708 is configured to receive input from a user 704. For example, the user interface 708 may include a keyboard, a touchscreen, a speaker, a mobile device, or any other device for receiving input, as known in the art. The user 704 enters data on the user interface 708 in response to prompts on the display 702 or may speak their answers which are recorded by the microphone 712. For example, the display 702 outputs a series of mental health questions (or the questions may be asked over the speaker), and the user 704 inputs an answer to each question on the user interface 708 through various methods. The user interface 708 is configured to directly display the input on display 702 and is configured to relay the data to the remote computing device 710.

The microphone 712 is configured to receive auditory input, for example, from the user 704. The microphone is configured to start or stop recording based on instructions from the remote computing device 710. The microphone is configured to transmit audio data to the remote computing device 710. In some examples, the microphone can be on a user's smart phone.

The display 702 is configured to receive data from the camera 706, the remote computing device 710, and the user interface 708. For example, the display 702 displays the visual data captured by the camera 706. In another example, the display 702 displays input received from the user interface. The display 702 is directly coupled to the camera 706 and the microphone 712 in some examples; in other examples, the camera 706 and the microphone 712 send their data to the remote computing device 710, which then processes the data and instructs the display 702 according to the processed data. In other examples, the display 702 displays data received from the remote computing device 710. Example data from the remote computing device 710 includes questions from a mental health questionnaire, answer boxes, answer options, answer data, a mental health indicator, or any other information. In some examples, the display 702 is on a smart phone.

The present disclosure also contemplates that more than one display 702 can be used in system 702, as would be readily contemplated by a person skilled in the art. For example, one display can be viewable by the user 704, while additional displays are visible to researchers and not to the user 704. The multiple displays can output identical or different information, according to instructions by the remote computing device 710.

A remote computing device 710 can be communicatively coupled to a display 702, a camera 706, a user interface 708, and a microphone 712. For example, the communication can be wired or wireless. The remote computing device 710 can process and/or store input from the display 702, the camera 706, the user interface 708, and the microphone 712.

In some examples, system 700 can be a user 704 with a unitary device, for example, a smart phone. The smart phone can have a display 702, a camera 706, a user interface 708, a computing device 710, and a microphone 710. For example, the user 704 can hold the smart phone in front of his or her face while reading text on the display 702 and responding to the mental health questionnaires.

Figure 30:
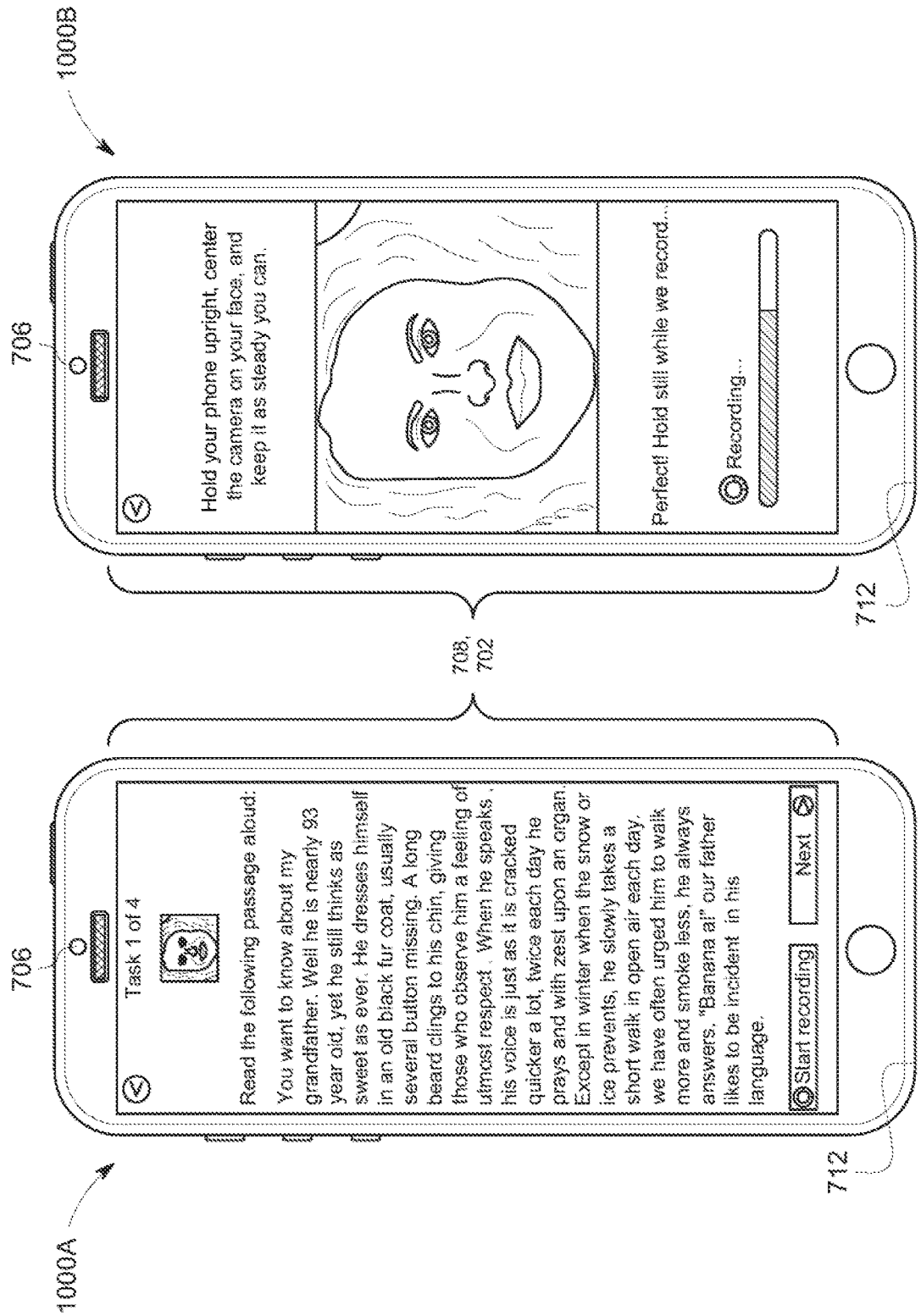
FIG. 30 depicts an interface including labels corresponding to elements of FIG. 29, according to some implementations of the present disclosure.

Referring briefly to FIG. 30, an example interface design is shown. Similar labels are used for corresponding elements to FIG. 29. A first screen 1000A of the interface design displays text for a user to read. A second screen 1000B of the interface design displays a face of the user as video data is being recorded. In some implementations, the first screen 1000A and the second screen 1000B are the same physical screen of an electronic device having the display 702 and the user interface 708. For example, the first screen 1000A and the second screen 1000B are displayed at two different points in time. FIG. 30 demonstrates how the disclosed system and methods can be performed on a local device, with ease of access for the user.

Test Application for Voice/Facial Recognition During Screening

Figure 31:
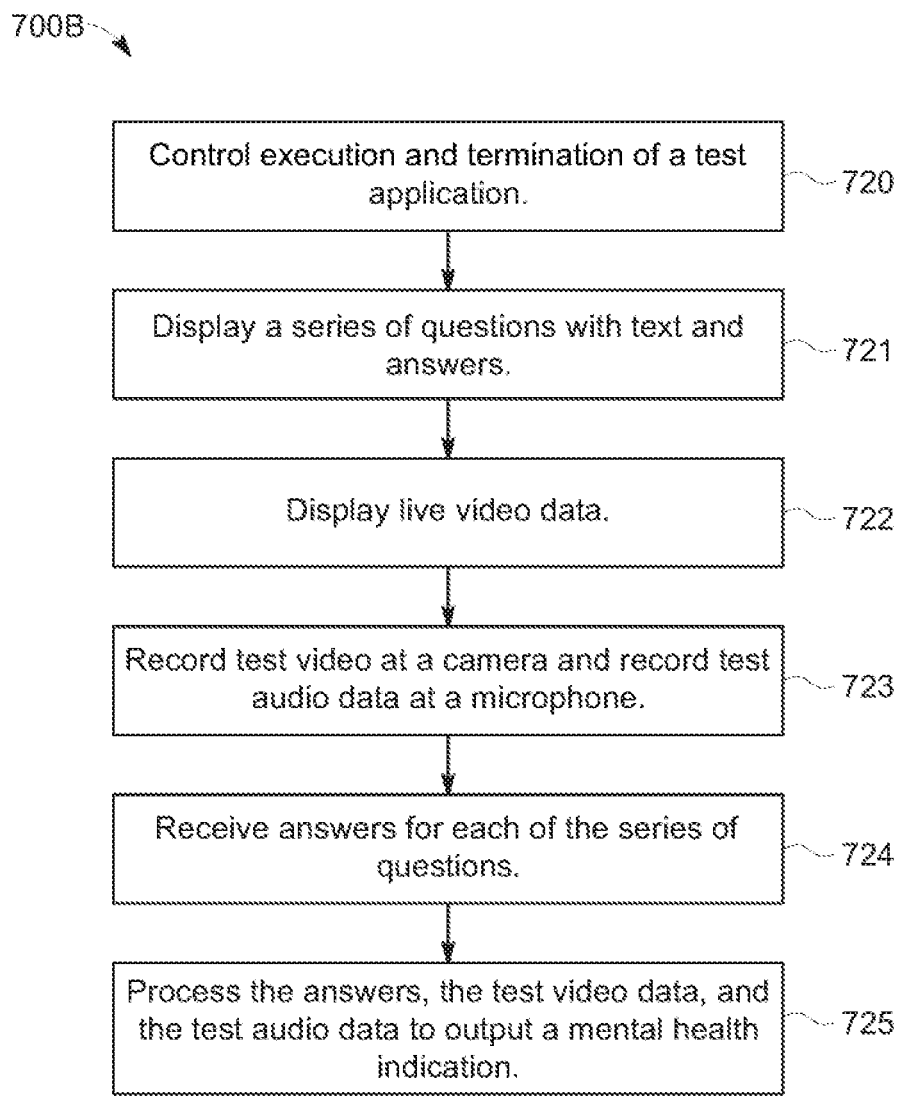
FIG. 31 depicts a flow chart of a method for executing a speaking task application on a user device, according to some implementations of the present disclosure.

FIG. 31 shows a flow chart showing an example method 700B, for executing a speaking task application on a user device and recording the audio and visual data during the test of the user's voice and facial expressions.

First, at step 720, the system may control execution and termination of a test application. The test application can be a software application stored on a computing device (e.g., the remote computing device 710 of FIG. 29). Step 720 provides for executing the test application upon receiving and indication to initiate a test. In some examples, the indication comes from a user interface (e.g., the user interface 708 of FIG. 29) communicatively coupled to the computing device.

Step 720 provides for executing the test application until the computing device receives an indication to stop the test. In some examples, this indication comes from the user interface. In some examples, the indication to stop the test includes determining, by the computing device, that the user's face is not within an image captured by a camera.

While the test is being executed according to step 720, methodology 700B proceeds to step 721. Step 721 provides for displaying a series of questions. An example series of questions includes questions from mental health questionnaires, and includes both text and answers for each question or open ended questions that will allow the patient to provide their own answers. In other examples, the system will display text for the user to read verbatim. In other examples, the system will provide questions using an audio modality over a speaker.

While the test is being executed according to step 720, methodology 700B can provide for step 722. Step 722 provides for displaying live video data. In some examples, live video data is collected from a camera positioned to capture an image in front of a display (e.g., camera 706 capturing visual data of user 704 positioned in front of the display 702, as shown in FIG. 30). In some examples, live video data is recorded and then displayed at a display; in other examples, live video data is simultaneously recorded and displayed. The display can be facing the user. This will allow the user to line up their face so that it is in the frame or field of view of the camera.

Step 723 provides for recording test video data and test audio data (e.g., from camera 706 and microphone 712 of FIG. 29). In some examples, the audio data and the video data are recorded in segments corresponding to the display of questions at step 722; in others examples, the data is collected in an un-interrupted stream while the questions or text is presented at step 722.

In some examples, a microphone (e.g., microphone 712 of FIG. 29) records audio data upon determining, by the computing device, that the user is speaking. In some examples, the microphone stops recording audio data when the computing device determines that the user is not speaking.

Step 724 provides for receiving answers for each of the series of questions (the questions provided for in step 721). The answers are received at a user interface. In some examples, the answers include selection of a multiple choice question, a textual response, or any other user input as contemplated by one skilled in the art. In other examples, the system will record the verbatim reading of the text. In some examples, answers to questions may be received through the microphone.

Step 725 provides for processing the answers and/or audio and visual data of the user reading text received at step 724 and the test video data and the test audio data recorded at step 723. In some examples, the processing is performed at a computing device using a machine learning model and results in outputting a mental health indication of the user. In some examples of the present disclosure, step 725 performs processing of the answers, the test video data, and the test audio data.

In some examples, the output mental health indication identifies a likelihood of the user having any one of several mental health disorders. The mental health disorders include a neuropsychiatric disorder, schizophrenia, and a bipolar disorder. In some examples, the mental health indication identifies whether the user is a patient or a healthy control.

This model can then be used as a diagnostic tool. For example, additional mental health questionnaire data, voice data, and/or video data can be input into the model to determine a mental health indication of a patient.

Data Separation and Feature Identification

Figure 32:
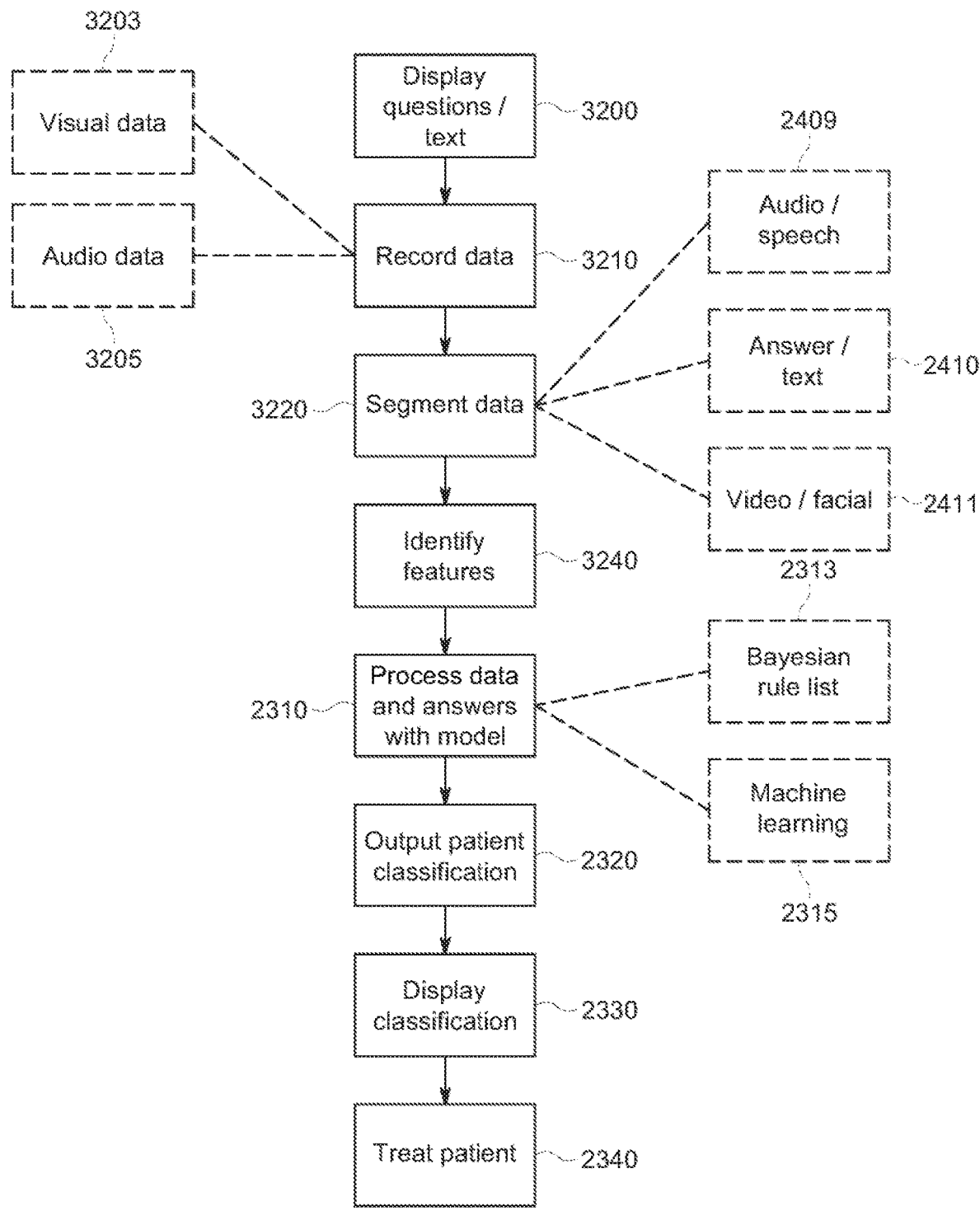
FIG. 32 depicts a flowchart of a data processing pipeline for reading task related data, according to some implementations of the present disclosure.

After the data is captured and recorded using the above systems and methods, the data may be first pre-processed to separate various modalities and features of the data. FIG. 32 illustrates a flowchart of an example data processing pipeline for reading task related data. In some examples, first questions or text will be displayed 3200 for the patient to answer or reach aloud. Next, the data will be recorded 3210 while the user is speaking as disclosed herein through the microphone and for instance a front facing camera on a smart phone or tablet in some examples. In some implementations, the data recorded at step 3210 includes visual data 3203 and audio data 3205.

Then the data will be segmented 3220 so that it can be pre-processed to identify features 3240. For instance, the audio data 3205 may be segmented into audio and/or speech data 2409 of the user speaking, and this data may be processed using language processing algorithms to identify the textual information or answers 2410. Additionally, the video data may be processed to identify the face and facial features 2411. The data may be time stamped so that audio, facial, and textual features may be linked in time, to have higher level features.

Next, the features in each of the modalities must be identified 3240. Various algorithms for each of the modalities may be utilized to identify the features 2310. In some implementations, the data and the answers are processed at step 2310 using one or more models, such as the Bayesian rule list 2313 and/or any suitable machine learning method 2314. The output from processing the data and the answers can include patient classification 2320. At step 2330, the output patient classification can be displayed on any suitable display device. Finally, the patient may be treated at step 2340 as described herein.

Following are some low level and high level features that may identified, however this is just example and not comprehensive.

Audio/Speech Features

The audio features identified may include local features, some global waveform level features, phoneme rate, demographic (gender, etc.), duration, speaking ratio, voice ratio, prosodic features, glottal and spectral features, or other suitable features. Some high level features may include statistical functionals, regression functions, and local maxima/minima related functionals. Additionally, dimensionality reduction may be performed on these features using a various of methods, which may include Brute-force methods and principal component analysis ("PCA").

Text Features

The audio features identified may include number of sentences, number of words, word embeddings, dictionary based methods, and session level features, for instance those discussed by Pampouchidou in "Depression Assessment by Fusing High and low Level Features from Audio, Video, and Text" AVEC 2016, the content of which is incorporated herein by reference in its entirety.

Video/Facial Features

The audio features identified may include facial action units, facial landmarks, or gaze direction as described by Valstar et al. in "AVEC 2016: Depression, Mood, and Emotional Recognition Workshop and Challenge", the content of which is incorporated herein by referenced in its entirety. Additional high level features may include geometric features described by Syed Mohammed's dissertation for the University of Auburn, Alabama in 2017 titled "The Application of Data Mining and Machine Learning in the Diagnosis of Mental Disorders" the content of which is incorporated herein by reference in its entirety. Additional high level features may include correlation and covariance matrices. Additionally, dimensionality reduction may be performed on these features using a various of methods, which may include Brute-force methods and PCA.

Processing Features with Model

After features have been identified they may be processed with a model 2310 as described herein, for instance a Bayesian Rule Decision List 2313. Accordingly, prior to processing these features, a Bayesian Rule List model and other processing models would be applied to generate a Bayesian Decision List that utilized rules with these features.

After processing with the list, the technology may output the patient classification 2320 and display it on a display 2330 as previously described herein. Finally, the patient may be treated 2340 as described herein.

Additional Implementations of Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present disclosure, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, e.g., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSION

While various examples of the present disclosure have been described above, it should be understood that they have been presented by way of example only, and not limitation. Numerous changes to the disclosed examples can be made in accordance with the disclosure herein without departing from the spirit or scope of the disclosure. Thus, the breadth and scope of the present disclosure should not be limited by any of the above described examples. Rather, the scope of the disclosure should be defined in accordance with the following claims and their equivalents.

Although the disclosure has been illustrated and described with respect to one or more implementations, equivalent alterations and modifications will occur to others skilled in the art upon the reading and understanding of this specification and the annexed drawings. In addition, while a particular feature of the disclosure may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the disclosure. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this disclosure belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

The invention claimed is:

1. A system for evaluating a patient for mental health issues, the system comprising:
   a memory containing machine readable medium comprising machine executable code having stored thereon instructions for performing a method; and
   a control system coupled to the memory comprising one or more processors, the control system configured to execute the machine executable code to cause the control system to:
   receive a plurality of input features, at least a portion of the plurality of input features being associated with clinical scales scores from a plurality of clinical questionnaires;
   process, using a Bayesian Decision List, the received plurality of input features, the Bayesian Decision List including a series of if then statements applied to the plurality of input features such that:
      in response to at least (i) a first input feature not exceeding a first threshold and (ii) a second input feature associated with a first clinical scales score from a first clinical questionnaire exceeding a second threshold, assigning a first probability to a potential indication of mental health of the patient; and
      else in response to at least (i) a third input feature not exceeding a third threshold and (ii) a fourth input feature associated with a second clinical scales score from a second clinical questionnaire exceeding a fourth threshold, assigning a second probability to the potential indication of mental health of the patient;
   based at least in part on the assigned probability of the potential indication, output an indication of mental health of the patient irrespective of a mental health condition, the indication of mental health identifying a drug to which the patient would likely be a higher responder; and
   in response to the outputted indication of mental health of the patient, recommend an effective amount of the identified drug to be administered to the patient,
   wherein the Bayesian Decision List was generated by:
      receiving labeled training data comprising data for a plurality of individuals, the labeled training data including category labels indicative of (i) whether each of the plurality of individuals has one or more mental health disorders and (ii) at least one drug to which each of the plurality of individuals would likely be a higher responder, the labeled training data comprising a plurality of attributes;

based at least in part on the received labeled training data, generating a plurality of rules predicting a category label associated with a set of attributes of the plurality of attributes, the set of attributes being associated with one or more clinical scales scores from one or more clinical questionnaires of the plurality of clinical questionnaires;

calculating a confidence score for each of the generated plurality of rules, the confidence score being representative of a capacity to predict the category label;

eliminating one or more rules of the generated plurality of rules based at in part on a threshold capacity to predict the category label; and generating the Bayesian Decision List designed to predict the category label using the rules that are not eliminated from the plurality of rules.

2. The system of claim 1, wherein the control system is further configured to output the mental health condition such as whether the patient has bi-polar disorder, ADHD, schizophrenia, OCD, PTSD, autism, or any combination thereof.

3. The system of claim 1, wherein the control system is further configured to determine whether the patient has the mental health condition.

4. The system of claim 1, wherein the received plurality of input features further includes one or more outcome measures from a probabilistic reward task, and wherein the first input feature processed using the Bayesian Decision List includes the outcome measure from the probabilistic reward task.

5. The system of claim 4, wherein the outcome measure from the probabilistic reward task includes a response bias, a discriminability, a reaction time, a rich hit rate, and a lean hit rate.

6. The system of claim 1, wherein the plurality of clinical questionnaires includes Montgomery-Asberg Depression Scale, Hamilton Anxiety Scale, Hospital Anxiety and Depression Scale, Snaith-Hamilton Pleasure Scale, and Dimensional Anhedonia Rating Scale.

7. The system of claim 1, wherein the received plurality of input features includes a score from a Temporal Experience of Pleasure Scale, and wherein the assigning the first probability to the potential indication of mental health of the patient is in response to at least the score from the Temporal Experience of Pleasure Scale exceeding a predetermined TEPS score.

8. The system of claim 7, wherein the score from the Temporal Experience of Pleasure Scale is associated TEPS9, and wherein the assigning the first probability to the potential indication of mental health of the patient is in response to at least the score from the Temporal Experience of Pleasure Scale exceeding 3.

9. The system of claim 7, wherein the score from the Temporal Experience of Pleasure Scale is associated TEPS-Total, and wherein the assigning the first probability to the potential indication of metal mental health of the patient is in response to at least the score from the Temporal Experience of Pleasure Scale exceeding 56.

10. The system of claim 1, wherein the category label is indicative of whether each of the plurality of individuals has one or more mental health disorders.

11. The system of claim 1, wherein the identified drug is a kappa opioid receptor antagonist (KORA).

12. The system of claim 1, further comprising based at least in part on the assigned probability of the potential indication, outputting the Bayesian Decision List.

13. A method for evaluating a patient for mental health issues, the method comprising:

receiving a plurality of input features, at least a portion of the plurality of input features being associated with clinical scales scores from a plurality of clinical questionnaires;

processing, using a Bayesian Decision List, the received plurality of input features, the Bayesian Decision List including a series of if then statements applied to the plurality of input features such that:

in response to at least (i) a first input feature not exceeding a first threshold and (ii) a second input feature associated with a first clinical scales score from a first clinical questionnaire exceeding a second threshold, assigning a first probability to a potential indication of mental health of the patient; and else in response to at least (i) a third input feature not exceeding a third threshold and (ii) a fourth input feature associated with a second clinical scales score from a second clinical questionnaire exceeding a fourth threshold, assigning a second probability to the potential indication of mental health of the patient;

based at least in part on the assigned probability of the potential indication, outputting an indication of mental health of the patient irrespective of a mental health condition, the indication of mental health identifying a drug to which the patient would likely be a higher responder; and in response to the outputted indication of mental health of the patient, recommending an effective amount of the identified drug to be administered to the patient, wherein the Bayesian Decision List was generated by:

receiving labeled training data comprising data for a plurality of individuals, the labeled training data including category labels indicative of (i) whether each of the plurality of individuals has one or more mental health disorders and (ii) at least one drug to which each of the plurality of individuals would likely be a higher responder, the labeled training data comprising a plurality of attributes;

based at least in part on the received labeled training data, generating a plurality of rules predicting a category label associated with a set of attributes of the plurality of attributes, the set of attributes being associated with one or more clinical scales scores from one or more clinical questionnaires of the plurality of clinical questionnaires;

calculating a confidence score for each of the generated plurality of rules, the confidence score being representative of a capacity to predict the category label;

eliminating one or more rules of the generated plurality of rules based at in part on a threshold capacity to predict the category label; and generating the Bayesian Decision List designed to predict the category label using the rules that are not eliminated from the plurality of rules.

14. A system for evaluating a patient for mental health issues, the system comprising a control system configured to implement the method of claim 13.

15. A computer program product comprising instructions which, when executed by a computer, cause the computer to carry out the method of claim 13.

16. The computer program product of claim 15, wherein the computer program product is a non-transitory computer readable medium.

* * * * *